(12) United States Patent
Fuwa et al.

(10) Patent No.: US 8,957,228 B2
(45) Date of Patent: Feb. 17, 2015

(54) MACROLIDE COMPOUND HAVING ANTICANCER EFFECT

(75) Inventors: Haruhiko Fuwa, Miyagi (JP); Makoto Sasaki, Miyagi (JP); Hiroshi Kubo, Miyagi (JP); Takaya Suzuki, Miyagi (JP)

(73) Assignee: Tohoku University, Sendai-shi (JP)

( * ) Notice: Subject to any disclaimer, the term of this patent is extended or adjusted under 35 U.S.C. 154(b) by 0 days.

(21) Appl. No.: 13/995,519

(22) PCT Filed: Oct. 28, 2011

(86) PCT No.: PCT/JP2011/006057
§ 371 (c)(1),
(2), (4) Date: Jun. 19, 2013

(87) PCT Pub. No.: WO2012/086114
PCT Pub. Date: Jun. 28, 2012

(65) Prior Publication Data
US 2013/0281714 A1    Oct. 24, 2013

(30) Foreign Application Priority Data
Dec. 24, 2010  (JP) .................. 2010-286945

(51) Int. Cl.
*C07D 321/00* (2006.01)
*C07D 493/16* (2006.01)
*C07D 493/18* (2006.01)

(52) U.S. Cl.
CPC ............ *C07D 493/16* (2013.01); *C07D 493/18* (2013.01)
USPC ........................................................ 549/267

(58) Field of Classification Search
USPC ....................................................... 549/267
See application file for complete search history.

(56) References Cited

U.S. PATENT DOCUMENTS

| 5,306,716 A | 4/1994 | Holt et al. |
| 5,324,720 A | 6/1994 | Holt et al. |
| 5,385,909 A | 1/1995 | Nelson et al. |
| 5,985,595 A | 11/1999 | Krider et al. |
| 2007/0270357 A1 | 11/2007 | Farmer et al. |
| 2009/0124562 A1 | 5/2009 | Shinya |

FOREIGN PATENT DOCUMENTS

| JP | 4 352783 | 12/1992 |
| JP | 7 504913 | 6/1995 |
| JP | 7 504914 | 6/1995 |
| JP | 9 505596 | 6/1997 |
| JP | 2004 210648 | 7/2004 |
| JP | 2007 512256 | 5/2007 |
| WO | 96 40869 | 12/1996 |
| WO | 2007 004621 | 1/2007 |

OTHER PUBLICATIONS

Ohta et al. Tetrahedron Letters, 2006, 47, 1957-1969.*
Dorwald F. A. Side Reactions in Organic Synthesis, 2005, Wiley: VCH, Weinheim p. IX of Preface p. 1-15.*
Venkatesh et al., Role of the Development Scientist in Compound Lead Selection and Optimization J. Pharm. Sci. 89, 145-54 (2000).*
Vougioukalakis Chem. Rev. 2010, 110, 1746-1787.*
Cook et al. Organic Letters, 2010, 12(4), 744-747.*
Takeda et al. Journal of Organic Chemistry, 104, 79, 2354-2367, Year 2014.*
Cook, C. et al., "Total Synthesis of (−)-Exiguolide", Organic Letters, vol. 12, No. 4, pp. 744-747, (Feb. 2010).
Fuwa, H. et al., "Total Synthesis of (−)-Exiguolide", Organic Letters, vol. 12, No. 3, pp. 584-587, (Feb. 2010).
Ohta, S. et al., "Exiguolide, a new macrolide form the marine sponge", Tetrahedeon Letters, vol. 47, No. 12, pp. 1957-1960, (2006).
Kwon, M., et al., "Total Synthesis of (+)-Exiguolide", Angewandte Chemie International Edition, vol. 47, No. 9, pp. 1733-1735, (2008).
Cossy, J. et al., "Exiguolide, a simplified analogue of the bryostatins by Nature?" Comptes Rendus Chimie, vol. 11, No. 11-12, pp. 1477-1482, (2008).
International Search Report Issued Nov. 11, 2011 in PCT/JP11/006057 Filed Oct. 28, 2011.

* cited by examiner

*Primary Examiner* — Nizal Chandrakumar
(74) *Attorney, Agent, or Firm* — Oblon, Spivak, McClelland, Maier & Neustadt, L.L.P.

(57) ABSTRACT

The present invention relates to a macrolide compound expected to have a cell growth-inhibiting activity and a novel anticancer drug utilizing the compound. Specifically, the invention relates to a compound represented by Formula (I) or (II) or a pharmaceutically acceptable salt thereof and relates to a cell growth inhibitor and an anticancer drug each containing the compound or the salt as an active ingredient.

3 Claims, 11 Drawing Sheets

FIG.1A
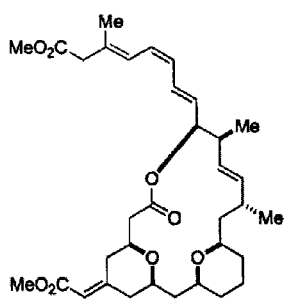
Exiguolide
(HF26074)
2.1 mg
Chemical Formula: C₃₄H₄₈O₈
Exact Mass: 584.3349
Molecular Weight: 584.7401
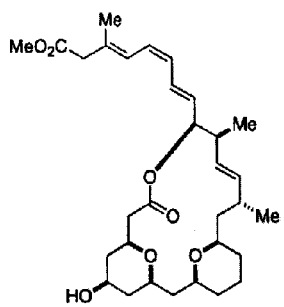
Analog 1
(HF27155)
2.3 mg
Chemical Formula: C₃₁H₄₆O₇
Exact Mass: 530.3244
Molecular Weight: 530.6927
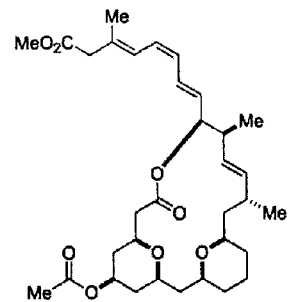
Analog 2
(HF27156)
2.4 mg
Chemical Formula: C₃₃H₄₈O₈
Exact Mass: 572.3349
Molecular Weight: 572.7294
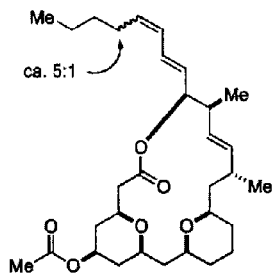
Analog 3
(HF27162)
2.2 mg
Chemical Formula: C₃₁H₄₈O₆
Exact Mass: 516.3451
Molecular Weight: 516.7092
| Abbreviation |
|---|
| Me = CH₃ |

FIG.1B
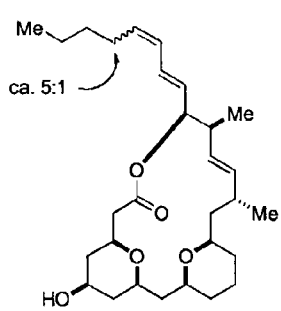
Analog 4
(HF27164)
1.4 mg
Chemical Formula: $C_{29}H_{46}O_5$
Exact Mass: 474.3345
Molecular Weight: 474.6725
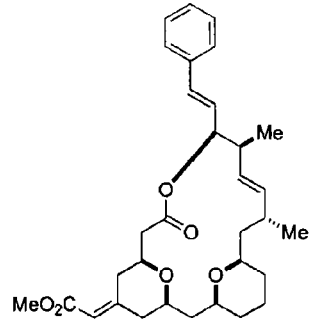
Analog 5
(HF27189)
1.4 mg
Chemical Formula: $C_{32}H_{42}O_6$
Exact Mass: 522.2981
Molecular Weight: 522.6723
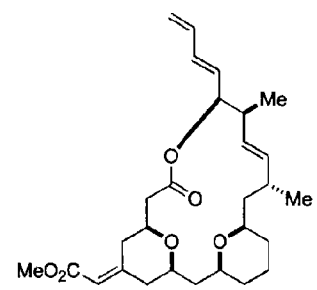
Analog 6
(HF27192)
1.1 mg
Chemical Formula: $C_{28}H_{40}O_6$
Exact Mass: 472.2825
Molecular Weight: 472.6136
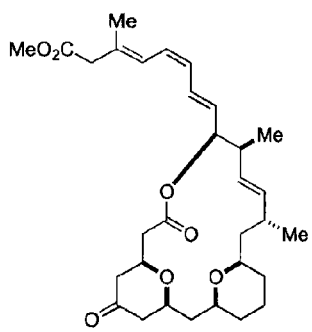
Analog 7
(HF27187)
2.2 mg
Chemical Formula: $C_{31}H_{44}O_7$
Exact Mass: 528.3087
Molecular Weight: 528.6769
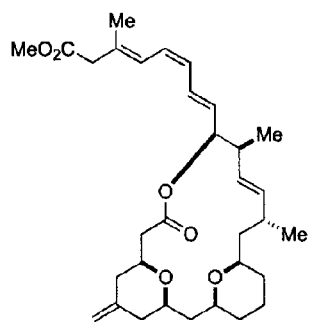
Analog 8
(HF27191)
0.9 mg
Chemical Formula: $C_{32}H_{46}O_6$
Exact Mass: 526.3294
Molecular Weight: 526.7040

FIG.2

| | Japanese Foundation for Cancer Research | | | | | | | | | | | Report Date:April 9,2010 | | |
|---|---|---|---|---|---|---|---|---|---|---|---|---|---|---|
| In-Vitro Testing Results | | | | | | | | | | | | | | |
| JCI:20915 exiguolide | | | | | | | | Exp.-IDR04701(High-Conc:-4) | | | | | | |

| Panel/Cel | Time Zero | Ctrl | Mean Optical Densities | | | | | Percent Growth | | | | | GI50 | TgI | LC50 |
|---|---|---|---|---|---|---|---|---|---|---|---|---|---|---|---|
| | | | -8 | -7 | -6 | -5 | -4 | -8 | -7 | -6 | -5 | -4 | | | |
| Br | * | | | | | | | | | | | | | | |
| HBC-4 | 0.59 | 2.06 | 2.25 | 2.24 | 2.02 | 1.25 | 1.28 | 113 | 113 | 98 | 45 | 47 | 8.1E-06 > | 1.0E-04 > | 1.0E-04 |
| BSY-1 | 0.47 | 0.69 | 0.78 | 0.76 | 0.69 | 0.51 | 0.53 | 140 | 130 | 100 | 17 | 27 | 4.0E-06 > | 1.0E-04 > | 1.0E-04 |
| HBC-5 | 0.49 | 0.90 | 0.97 | 0.94 | 0.93 | 0.72 | 0.73 | 117 | 110 | 107 | 56 | 59 > | 1.0E-04 > | 1.0E-04 > | 1.0E-04 |
| MCF-7 | 0.75 | 2.60 | 2.71 | 2.62 | 2.60 | 1.78 | 1.19 | 106 | 102 | 100 | 56 | 23 | 1.5E-05 > | 1.0E-04 > | 1.0E-04 |
| MDA-MB-23 | 0.66 | 1.42 | 1.58 | 1.52 | 1.29 | 1.03 | 0.92 | 122 | 113 | 83 | 49 | 35 | 9.5E-06 > | 1.0E-04 > | 1.0E-04 |
| CNS | * | | | | | | | | | | | | | | |
| U251 | 0.55 | 2.25 | 2.15 | 2.25 | 2.11 | 1.47 | 1.22 | 94 | 100 | 92 | 54 | 40 | 1.9E-05 > | 1.0E-04 > | 1.0E-04 |
| SF-268 | 0.51 | 1.49 | 1.45 | 1.46 | 1.36 | 0.98 | 0.94 | 95 | 96 | 86 | 47 | 44 | 8.5E-06 > | 1.0E-04 > | 1.0E-04 |
| SF-295 | 0.55 | 1.39 | 1.32 | 1.44 | 1.31 | 0.96 | 0.81 | 91 | 105 | 91 | 48 | 30 | 9.0E-06 > | 1.0E-04 > | 1.0E-04 |
| SF-539 | 0.40 | 1.15 | 1.22 | 1.12 | 1.12 | 0.74 | 0.69 | 109 | 96 | 97 | 45 | 38 | 8.0E-06 > | 1.0E-04 > | 1.0E-04 |
| SNB-75 | 0.72 | 1.07 | 1.03 | 1.01 | 1.03 | 0.92 | 0.85 | 87 | 81 | 88 | 56 | 37 | 2.0E-05 > | 1.0E-04 > | 1.0E-04 |
| SNB-78 | 1.02 | 1.68 | 1.59 | 1.58 | 1.46 | 1.28 | 1.25 | 87 | 86 | 67 | 39 | 35 | 4.1E-06 > | 1.0E-04 > | 1.0E-04 |
| Co | * | | | | | | | | | | | | | | |
| HCC2998 | 0.68 | 1.90 | 1.86 | 1.74 | 1.64 | 1.34 | 1.08 | 97 | 87 | 79 | 54 | 32 | 1.5E-05 > | 1.0E-04 > | 1.0E-04 |
| KM-12 | 1.05 | 2.81 | 2.83 | 2.81 | 2.77 | 2.22 | 1.77 | 101 | 100 | 98 | 67 | 41 | 4.5E-05 > | 1.0E-04 > | 1.0E-04 |
| HT-29 | 0.58 | 2.57 | 2.55 | 2.46 | 2.35 | 1.81 | 1.37 | 99 | 94 | 89 | 62 | 40 | 3.5E-05 > | 1.0E-04 > | 1.0E-04 |
| HCT-15 | 0.49 | 2.47 | 2.47 | 2.54 | 2.47 | 1.80 | 1.21 | 100 | 104 | 100 | 66 | 36 | 3.5E-05 > | 1.0E-04 > | 1.0E-04 |
| HCT-116 | 0.38 | 2.32 | 2.39 | 2.49 | 2.30 | 1.32 | 1.01 | 104 | 109 | 99 | 48 | 32 | 9.2E-06 > | 1.0E-04 > | 1.0E-04 |
| Lu | * | | | | | | | | | | | | | | |
| NCI-H23 | 0.58 | 1.56 | 1.60 | 1.54 | 1.38 | 1.04 | 1.06 | 104 | 98 | 82 | 47 | 49 | 8.3E-06 > | 1.0E-04 > | 1.0E-04 |
| NCI-H226 | 0.47 | 0.83 | 0.82 | 0.79 | 0.67 | 0.54 | 0.56 | 97 | 89 | 57 | 21 | 26 | 1.6E-06 > | 1.0E-04 > | 1.0E-04 |
| NCI-H522 | 0.60 | 1.24 | 1.25 | 1.18 | 1.14 | 1.04 | 0.89 | 101 | 91 | 84 | 69 | 45 | 6.2E-05 > | 1.0E-04 > | 1.0E-04 |
| NCI-H460 | 0.33 | 2.07 | 0.75 | 0.55 | 0.51 | 0.54 | 0.47 | 24 | 13 | 10 | 12 | 8 < | 1.0E-08 > | 1.0E-04 > | 1.0E-04 |
| A549 | 0.58 | 2.51 | 2.39 | 2.00 | 1.44 | 1.11 | 1.09 | 94 | 74 | 45 | 27 | 27 | 6.5E-07 > | 1.0E-04 > | 1.0E-04 |
| DMS273 | 0.26 | 1.43 | 1.52 | 1.36 | 1.31 | 0.60 | 0.57 | 108 | 94 | 89 | 29 | 26 | 4.5E-06 > | 1.0E-04 > | 1.0E-04 |
| DMS114 | 0.65 | 1.64 | 1.65 | 1.76 | 1.83 | 1.38 | 1.08 | 101 | 113 | 119 | 74 | 44 | 6.3E-05 > | 1.0E-04 > | 1.0E-04 |
| Me | * | | | | | | | | | | | | | | |
| LOX-IMVI | 0.34 | 1.00 | 1.16 | 1.15 | 1.12 | 0.84 | 0.56 | 125 | 123 | 117 | 75 | 34 | 4.1E-05 > | 1.0E-04 > | 1.0E-04 |
| Ov | * | | | | | | | | | | | | | | |
| OVCAR-3 | 0.47 | 1.19 | 1.26 | 1.23 | 1.18 | 0.90 | 0.81 | 110 | 106 | 99 | 60 | 47 | 6.2E-05 > | 1.0E-04 > | 1.0E-04 |
| OVCAR-4 | 0.35 | 0.80 | 0.79 | 0.81 | 0.75 | 0.67 | 0.57 | 98 | 103 | 90 | 72 | 49 | 9.3E-05 > | 1.0E-04 > | 1.0E-04 |
| OVCAR-5 | 0.42 | 1.09 | 1.09 | 1.09 | 1.00 | 0.85 | 0.78 | 99 | 100 | 86 | 64 | 54 > | 1.0E-04 > | 1.0E-04 > | 1.0E-04 |
| OVCAR-8 | 0.36 | 1.61 | 1.59 | 1.53 | 1.46 | 1.14 | 0.85 | 99 | 93 | 88 | 63 | 40 | 3.5E-05 > | 1.0E-04 > | 1.0E-04 |
| SK-OV-3 | 0.64 | 1.43 | 1.30 | 1.17 | 1.01 | 0.88 | 0.88 | 84 | 68 | 47 | 30 | 30 | 7.0E-07 > | 1.0E-04 > | 1.0E-04 |
| Re | * | | | | | | | | | | | | | | |
| RXF-631L | 1.16 | 2.61 | 2.57 | 2.45 | 2.14 | 1.69 | 1.66 | 97 | 89 | 68 | 37 | 35 | 3.7E-06 > | 1.0E-04 > | 1.0E-04 |
| ACHN | 0.68 | 2.44 | 2.40 | 2.17 | 1.83 | 1.27 | 1.11 | 98 | 85 | 65 | 34 | 25 | 3.1E-06 > | 1.0E-04 > | 1.0E-04 |
| St | * | | | | | | | | | | | | | | |
| St-4 | 0.72 | 2.19 | 2.01 | 2.07 | 1.98 | 1.60 | 1.38 | 88 | 92 | 86 | 60 | 45 | 4.7E-05 > | 1.0E-04 > | 1.0E-04 |
| MKN1 | 0.53 | 1.36 | 1.29 | 1.17 | 1.05 | 0.93 | 0.97 | 91 | 76 | 63 | 48 | 53 > | 1.0E-04 > | 1.0E-04 > | 1.0E-04 |
| MKN7 | 0.52 | 1.32 | 1.22 | 1.29 | 1.16 | 0.85 | 0.74 | 89 | 97 | 80 | 42 | 28 | 6.2E-06 > | 1.0E-04 > | 1.0E-04 |
| MKN28 | 0.29 | 1.04 | 1.00 | 0.99 | 0.89 | 0.64 | 0.52 | 95 | 93 | 79 | 46 | 30 | 7.7E-06 > | 1.0E-04 > | 1.0E-04 |
| MKN45 | 0.51 | 1.43 | 1.46 | 1.54 | 1.35 | 0.88 | 0.74 | 103 | 112 | 91 | 40 | 25 | 6.5E-06 > | 1.0E-04 > | 1.0E-04 |
| MKN74 | 0.39 | 0.90 | 0.89 | 0.86 | 0.60 | 0.58 | 0.53 | 98 | 92 | 42 | 38 | 27 | 6.9E-07 > | 1.0E-04 > | 1.0E-04 |
| xPg | * | | | | | | | | | | | | | | |
| DU-145 | 0.75 | 2.16 | 2.21 | 2.22 | 1.94 | 1.43 | 1.30 | 103 | 104 | 84 | 48 | 39 | 9.1E-06 > | 1.0E-04 > | 1.0E-04 |
| PC-3 | 1.47 | 2.62 | 2.65 | 2.62 | 2.41 | 1.91 | 1.56 | 103 | 100 | 82 | 39 | 8 | 5.4E-06 > | 1.0E-04 > | 1.0E-04 |

FIG.6
| | H460 | A549 | A172 | HUVEC |
|---|---|---|---|---|
| | 50% GROWTH INHIBITION CONCENTRATION (IC50) | | | |
| EXIGUOLIDE | 0.2803 | 0.5914 | 0.4656 | 1.211 |
| ANALOG 1 | 3.55 | 2.854 | 1.939 | 3.203 |
| ANALOG 2 | 3 | >100 | >100 | |
| ANALOG 3 | >100 | >100 | >100 | |
| ANALOG 4 | 5.608 | 2.38 | 1.83 | |
| ANALOG 5 | 51.47 | >100 | >100 | |
| ANALOG 6 | 15.96 | >100 | 2.116 | |
| ANALOG 7 | 99.75 | 44.42 | 51.92 | |
| ANALOG 8 | >100 | >100 | >100 | (IC50: μM) |
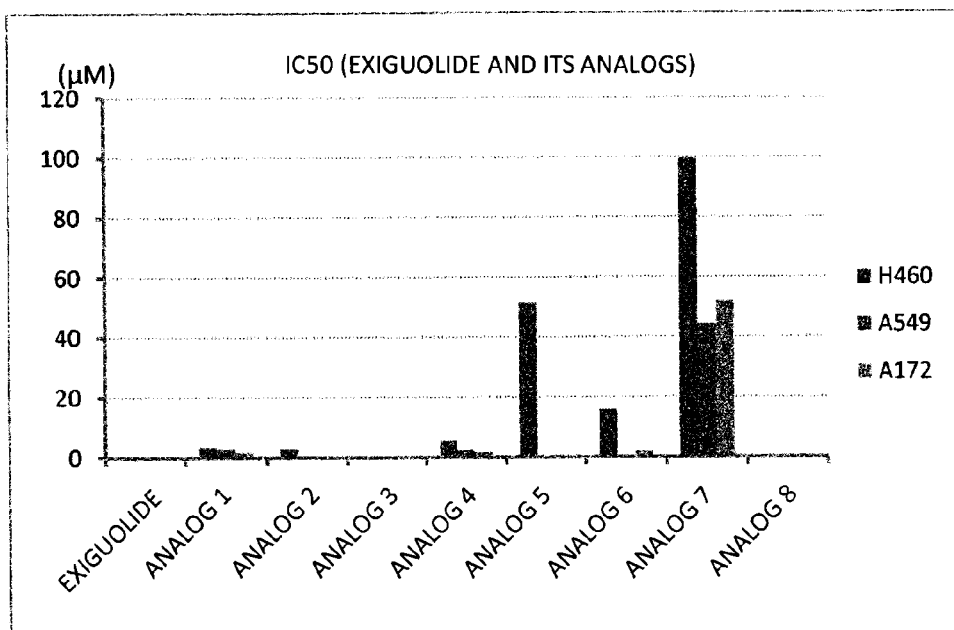
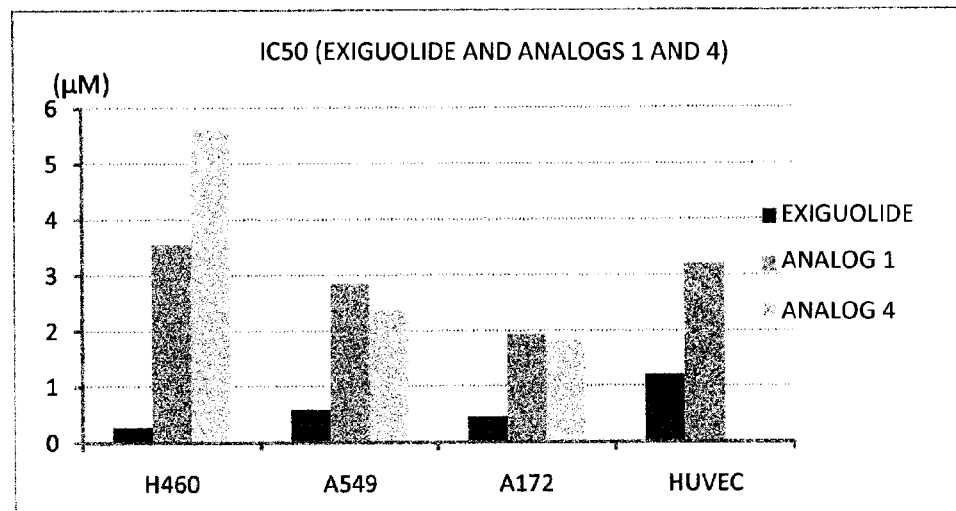

RATIO OF EACH CELL CYCLE
(EXIGUOLIDE 1 μM)

PHOSPHORYLATION STATE OF G1 PHASE REGULATORY PROTEIN Rb

| EXIGUOLIDE CONCENTRATION (μM) | 5 | 1 | 0.5 | 0.1 | 0.05 | 0.01 | 0 |

MACROLIDE COMPOUND HAVING ANTICANCER EFFECT

TECHNICAL FIELD

The present invention relates to a novel macrolide compound having a cell growth-inhibiting activity. More specifically, the invention relates to an anticancer drug containing, as an active ingredient, a novel macrolide compound having a cell growth-inhibiting activity or a pharmaceutically acceptable salt thereof.

BACKGROUND ART

Exiguolide is one of macrocyclic lactones isolated from sponges and is known to have an activity of inhibiting maturation of ova and spermatozoa of *Hemicentrotus pulcherrimus* (Non Patent Literature 1). Exiguolide has a 20-membered cyclic macrolide structure including a partial structure similar to bryostatins. Regarding chemical synthesis of exiguolide, total synthesis of (+)exiguolide has been published by a group of Seoul National University in 2008 (Non Patent Literature 2), and total synthesis of (−)exiguolide has been published by the present inventors in 2010 (Non Patent Literature 3).

Various macrolide compounds naturally exist, and macrolide compounds having various bioactivities, such as antibacterial agents, antifungal agents, and immunosuppressive agents, are known. Among these compounds, macrolide antibiotics are particularly useful. For example, erythromycin discovered from *Streptomyces* and its analogs such as clarithromycin are known.

It is also known that the macrolide compounds include many compounds showing anticancer activities through cytotoxicity or immune activity (Patent Literatures 1 to 7). Bryostatins are one example thereof. Bryostatins are natural macrolide compounds isolated from marine organisms, and not less than twenty analogs are known. At present, bryostatins are under many clinical tests for, for example, leukemia or Alzheimer dementia and are expected to show advantageous effects in combination with other anticancer drugs or effects of overcoming multiple drug resistance. The structure of exiguolides can be recognized as a simplified analog of the bryostatins (Non Patent Literature 4), and exiguolides are expected to have various bioactivities. However, any bioactivity, such as a cell growth-inhibiting activity or anticancer activity, has not been verified in the exiguolide.

CITATION LIST

Patent Literature

Patent Literature 1: JP1992-352783T
Patent Literature 2: JP1995-504913T
Patent Literature 3: JP1995-504914T
Patent Literature 4: JP1997-505596T
Patent Literature 5: WO2007/004621
Patent Literature 6: JP2004-210648A
Patent Literature 7: JP2007-512256T

Non Patent Literature

Non Patent Literature 1: Ohta S. et al., Tetrahedron Letters 47(12), 2006, pp. 1957-1960
Non Patent Literature 2: Kwon et al., Angewandte Chemie International Edition, 47(9), 2008, pp. 1733-1735
Non Patent Literature 3: Fuwa H. et al., Organic Letters, 12(3), 2010, pp. 584-587
Non Patent Literature 4: Cossy J., Comptes Rendus Chimie, 11(11-12), 2008, pp. 1477-1482

SUMMARY OF INVENTION

Technical Problem

It is an object of the present invention to provide a novel macrolide compound that can be expected to have cell growth-inhibiting activity and a pharmaceutical composition containing the compound for treating cancer.

Solution to Problem

The present inventors have examined the anticancer activity of (−)exiguolide by a drug sensitivity test using a panel of 39 human cultured cancer cell lines and analyzed the growth-inhibiting effects on various cancer cells and characteristics thereof. Furthermore, the inventors have synthesized various analogs of (−) exiguolide and have investigated the cell growth-inhibiting effect thereof.

As a result, it was found that (−)exiguolide and its analogs show significant cell growth-inhibiting effects on specific cancer cells and that the effects are remarkably higher than those of known bryostatins (bryostatin 1) that are similar in structure to (−) exiguolide. Furthermore, it was found that the mechanism and the phase (cell cycle) of the activity are likely different from those of known anticancer drugs.

That is, the present invention relates to a compound represented by Formula (I) or (II):

[Formula 1]

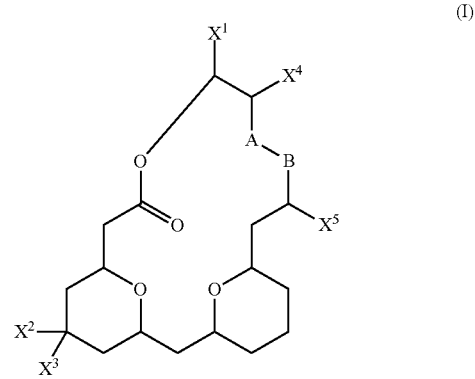

(I)

wherein, $X^1$ represents any one of the following formulae:

[Formula 2]

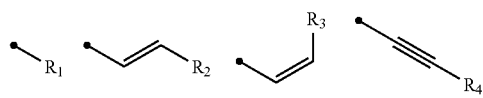

(wherein, $R_1$ represents H, alkyl, aryl, heteroaryl, heterocyclyl, —CONRi-, —NRiCO—, —C(O)—, —S—, —S(O)—, or —S(O)$_2$—; and $R_2$, $R_3$, and $R_4$ each independently represent H, alkyl, alkenyl, alkynyl, aryl, heteroaryl, heterocyclyl, —CONRi-, —NRiCO—, —C(O)—, —S—, —S(O)—, or —S(O)$_2$—);

$X^2$ and $X^3$ each independently represent H, alkyl, alkenyl, alkynyl, aryl, heteroaryl, heterocyclyl, —O—, —OC(O)—, —CONRi-, —C(O)—, —S—, —S(O)—, —S(O)$_2$—, —NRi-, or —NRiCO—;

$X^4$ and $X^5$ each independently represent H, alkyl, alkenyl, alkynyl, aryl, heteroaryl, or heterocyclyl;

A-B represents CH$_2$—CH$_2$, CH=CH, CH$_2$—O, or O—CH$_2$; and each Ri and each Rii independently represent H, alkyl, alkenyl, alkynyl, aryl, heteroaryl, or heterocyclyl,

[Formula 3]

(II)

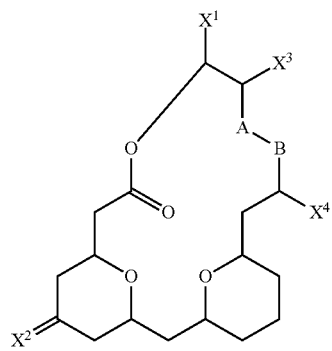

wherein, $X^1$ represents any one of the following formulae:

[Formula 4]

(wherein, R$_1$ represents H, alkyl, aryl, heteroaryl, heterocyclyl, —CONRi-, —NRiCO—, —C(O)—, —S—, —S(O)—, or —S(O)$_2$—; and R$_2$, R$_3$, and R$_4$ each independently represent H, alkyl, alkenyl, alkynyl, aryl, heteroaryl, heterocyclyl, —CONRi-, —NRiCO—, —C(O)—, —S—, —S(O)—, or —S(O)$_2$—);

$X^2$ represents =O, =NC(O)—, =NS(O)$_2$—, =CRi-, =CRiC(O)—, =CRiC(O)O—, =CRiC(O)NRii-, =CRiC(O)S—, =C(C(O)—)$_2$, =C(C(O)O—)$_2$, =C(C(O)Ri)(C(O)Rii), or =C(C(O)ORi)(C(O)ORii);

$X^3$ and $X^4$ each independently represent H, alkyl, alkenyl, alkynyl, aryl, heteroaryl, or heterocyclyl;

A-B represents CH$_2$—CH$_2$, CH=CH, CH$_2$—O, or O—CH$_2$; and each Ri and each Rii independently represent H, alkyl, alkenyl, alkynyl, aryl, heteroaryl, or heterocyclyl, or a pharmaceutically acceptable salt of the compound.

The present invention also provides a cell growth inhibitor containing the above-mentioned compound or a pharmaceutically acceptable salt thereof.

Examples of the cells as a subject on which the inhibitor acts include cancer cells.

The present invention also provides an anticancer drug containing the above-mentioned compound or a pharmaceutically acceptable salt thereof.

Examples of the cancer as a target on which the anticancer drug or the cell growth inhibitor of the present invention acts include pancreatic cancer, colon cancer, liver cancer, brain cancer, lung cancer, squamous cell carcinoma, bladder cancer, gastric cancer, pancreatic cancer, prostatic cancer, kidney cancer, colorectal cancer, breast cancer, head cancer, neck cancer, esophageal cancer, gynecological cancer, thyroid cancer, lymphoma, chronic leukemia, and acute leukemia.

In particular, the anticancer drug and the cell growth inhibitor of the present invention are expected to be effective on lung cancer and lung cancer cells.

Advantageous Effects of Invention

The present invention provides a novel macrolide compound having a cell growth-inhibiting activity. The macrolide compound of the present invention exhibits remarkable cell growth-inhibiting effects on specific cancer cells, while showing low activities on normal cells. In addition, the macrolide compound may have a mechanism of action different from those of conventionally known anticancer drugs with a high probability and is therefore expected to show advantageous effects in combination with other anticancer drugs or effects of overcoming multiple drug resistance.

BRIEF DESCRIPTION OF DRAWINGS

FIG. 1A shows the structures of (−) exiguolide and its analogs 1 to 3.

FIG. 1B shows the structures of (−) exiguolide and its analogs 4 to 8.

FIG. 2 shows the results (each parameter) of a drug sensitivity test of (−)exiguolide using a panel of human cultured cancer cell lines.

FIG. 6 shows 50% growth inhibition concentration (IC$_{50}$) levels of (−)exiguolide and its analogs 1 to 8 on H460, A549, A172, and HUVEC cell lines, where the graph at the center shows comparison of IC$_{50}$ levels of exiguolide and analogs 1 to 8 for each cell line (the bars in the graph represent IC$_{50}$ levels for H460, A549, and A172 cell lines from the left); and the lower graph shows comparison of IC$_{50}$ levels of exiguolide and analogs 1 and 4 for each cell line (the bars in the graph represent exiguolide, analog 1, and analog 4 from the left).

Figure 3:
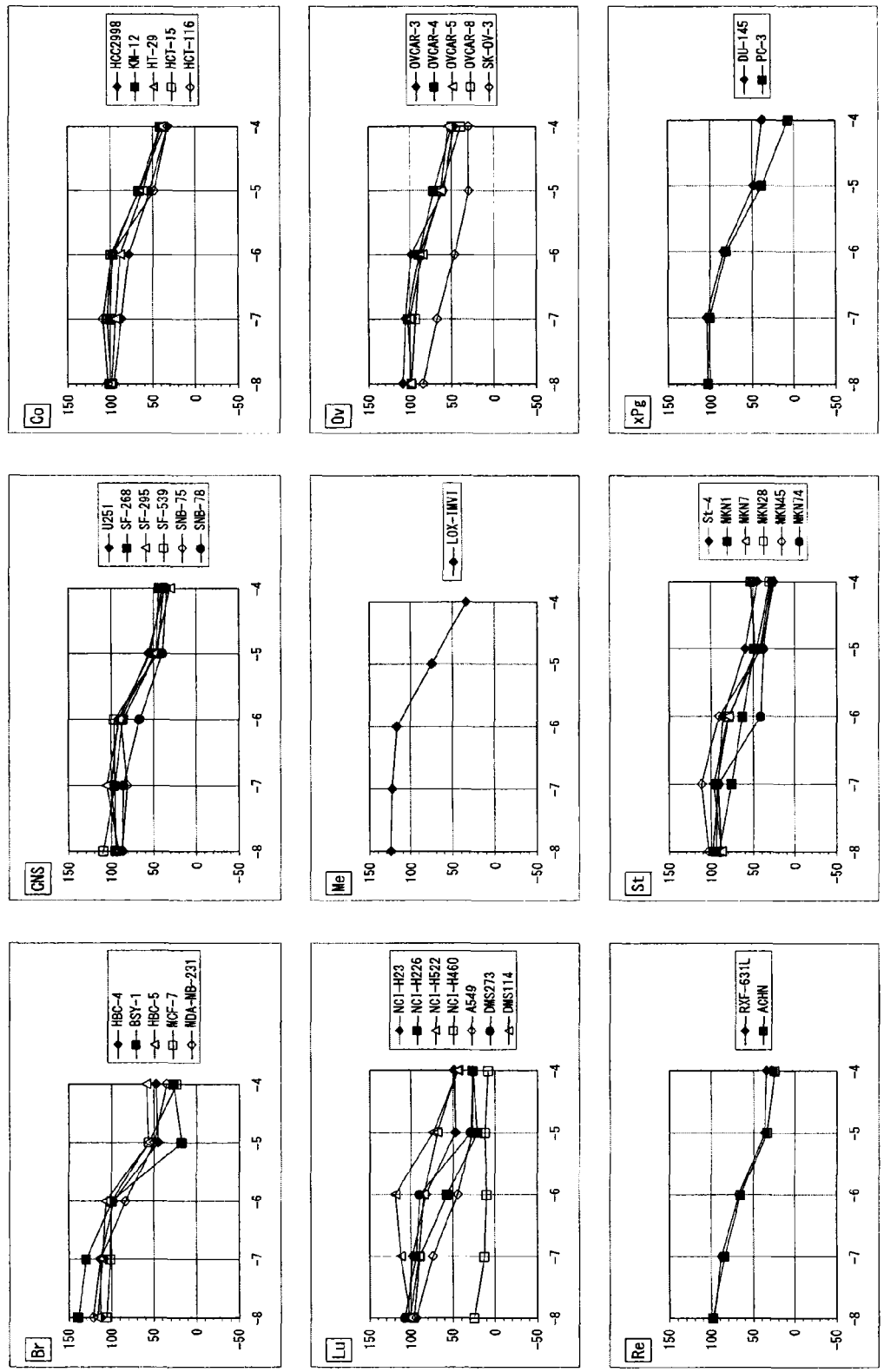
FIG. 3 shows the results (dose-response curves of cell growth rate) of a drug sensitivity test of (−)exiguolide using a panel of human cultured cancer cell lines, where in each graph, the vertical axis represents the cell growth rate (%); and the horizontal axis represents the drug concentration (M).

This description includes the contents as disclosed in the description of Japanese Patent Application No. 2010-286945, which is a priority document of the present application.

DESCRIPTION OF EMBODIMENTS

1. Definition

Throughout the description, the term "alkyl" means a saturated straight-chain (unbranched) or branched, noncyclic hydrocarbon having 1 to 10, preferably 1 to 5, carbon atoms. Typical examples of the saturated straight-chain (unbranched) alkyl include -methyl, -ethyl, -n-propyl, -n-butyl, -n-pentyl, -n-hexyl, -n-heptyl, -n-octyl, -n-nonyl, and n-decyl; and typical examples of saturated branched alkyl include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, and 3,3-diethylhexyl.

Throughout the description, the term "alkenyl" means a straight-chain or branched, noncyclic hydrocarbon having 2 to 10, preferably 1 to 5, carbon atoms and having at least one carbon-carbon double bond. Typical examples of the straight-chain or branched ($C_2$ to $C_{10}$) alkenyl include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, and -3-decenyl. The alkenyl group may be substituted or not substituted.

Throughout the description, the term "alkynyl" means a straight-chain or branched, noncyclic hydrocarbon having 2 to 10, preferably 2 to 5, carbon atoms and having at least one carbon-carbon triple bond. Typical examples of the straight-chain or branched ($C_2$ to $C_{10}$) alkynyl include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, and -9-decynyl. The alkynyl group may be substituted or not substituted.

Throughout the description, the term "aryl" means a carbocyclic aromatic group having 5 to 10 ring atoms. Typical examples thereof include, but not limited to, phenyl, tolyl, anthracenyl, fluorenyl, indenyl, azulenyl, pyridinyl, and naphthyl, and also include benzo-fused carbocyclic moieties such as 5,6,7,8-tetrahydronaphthyl. The carbocyclic aromatic group may be substituted or not substituted. In one embodiment, the carbocyclic aromatic group is a phenyl group.

Throughout the description, the term "heteroaryl" means a 5 to 10-membered aromatic heterocycle having at least one hetero atom selected from nitrogen, oxygen, and sulfur atoms and having at least one carbon atom and includes both monocycle and bicycle. Typical examples of the heteroaryl include triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzoimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thiethanyl, and oxazolyl.

Throughout the description, the term "heterocyclyl" means saturated or unsaturated 5 to 7-membered monocyclic or 7 to 10-membered bicyclic heterocycle having 1 to 4 hetero atoms independently selected from nitrogen, oxygen, and sulfur atoms, wherein the nitrogen and sulfur hetero atoms are optionally oxidized, and the nitrogen hetero atom is optionally quaternized, and includes a bicycle formed by condensation of any of these heterocyclyls to a benzene ring. The heterocyclyl can bond via an appropriate hetero atom or carbon atom. The heteroaryls defined above are included in the heterocyclyl. Typical examples of the heterocyclyl include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, and tetrahydrothiopyranyl.

Throughout the description, the term "pharmaceutically acceptable salt" means a salt prepared from a pharmaceutically acceptable non-toxic acid or base, of which examples include inorganic acids and bases and organic acids and bases. Examples of the pharmaceutically acceptable base addition salt suitable for the compound of the present invention include, but not limited to, metal salts formed from aluminum, calcium, lithium, magnesium, potassium, sodium, and zinc; and organic salts formed from lysine, N,N'-dibenzylethylenediamine, chloroprocaine, choline, diethanolamine, ethylenediamine, meglumine (N-methylglucamine), and procaine. Examples of the suitable non-toxic acid include, but not limited to, inorganic and organic acids, such as acetic acid, alginic acid, anthranilic acid, benzenesulfonic acid, benzoic acid, camphorsulfonic acid, citric acid, ethenesulfonic acid, formic acid, fumaric acid, furoic acid, galacturonic acid, gluconic acid, glucuronic acid, glutamic acid, glycolic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phenylacetic acid, phosphoric acid, propionic acid, salicylic acid, stearic acid, succinic acid, sulfanilic acid, sulfuric acid, tartaric acid, and p-toluenesulfonic acid. Specific examples of the non-toxic acid include hydrochloric acid, hydrobromic acid, phosphoric acid, sulfuric acid, and methanesulfonic acid. Accordingly, specific examples of the salt include hydrochlorides and mesylates. Other salts are known in the art and are described in, for example, Remington's Pharmaceutical Sciences, 18th Eds.

The compound or a pharmaceutically acceptable salt thereof of the present invention may be in a solvate, hydrate, clathrate, or prodrug form.

Herein, the term "solvate" means the compound or a salt thereof of the present invention further including a stoichiometric or non-stoichiometric amount of solvent bound by non-covalent intermolecular forces. The solvent is preferably volatile, non-toxic, and/or compatible with administration to human in a very small amount.

The term "hydrate" means the compound or a salt thereof of the present invention further including a stoichiometric or non-stoichiometric amount of water bound by non-covalent intermolecular forces.

The term "clathrate" means the compound or a salt thereof of the present invention in a crystal lattice form having spaces (e.g., channels) including guest molecules (e.g., solvent or water) trapped therein.

The term "prodrug" means the compound of the present invention that can provide an active compound (in particular, a compound of the present invention) through hydrolysis, oxidation, or another reaction under biological conditions (in vitro or in vivo). Examples of the prodrug include, but not limited to, metabolites of the compound of the present invention containing biohydrolyzable moieties such as biohydrolyzable amide, biohydrolyzable ester, biohydrolyzable carbamate, biohydrolyzable carbonate, biohydrolyzable ureide, and biohydrolyzable phosphate analogs. The prodrug of a compound having a carboxyl functional group is preferably a lower alkyl ester of carboxylic acid. The carboxylate ester can be more conveniently prepared by esterifying any of carboxylic acid moieties existing on the molecule. The prodrug can be typically prepared by a known method such as a method described in, for example, Burger's Medicinal Chemistry and Drug Discovery 6th Ed.

Throughout the description, the term "cell growth inhibitor" is a drug that inhibits growth of cells. The type of cells is not limited, but it is preferable that the inhibitor less act on normal cells and show the growth-inhibiting effect on specific cancer cells only, in light of using as an anticancer drug described below.

Throughout the description, the term "anticancer drug" is a pharmaceutical composition that is used for treatment or prevention of cancer. The term "treatment" includes eradication, removal, remedy, or inhibition of primary, local, or metastatic cancer tissue and also includes minimization or delay of the progress of cancer. The term "prevention" includes prevention of recurrence, progress, or occurrence of cancer in a patient.

2. Macrolide Compound of the Present Invention

The macrolide compounds according to the present invention are (−)exiguolide and its analogs and exhibit growth-inhibiting activities on cells showing abnormal growth, such as cancer cells.

Exiguolide is, as described above, one of macrocyclic lactones isolated from sponges and is known to have an activity of inhibiting maturation of ova and spermatozoa of *Hemicentrotus pulcherrimus*. Exiguolide has a 20-membered cyclic macrolide structure including a partial structure similar to bryostatins.

In one embodiment, the macrolide compound of the present invention is represented by Formula (I):

[Formula 5]

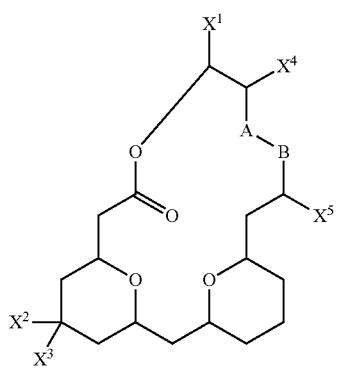

(I)

In the formula, $X^1$ represents any one of the following formulae:

[Formula 6]

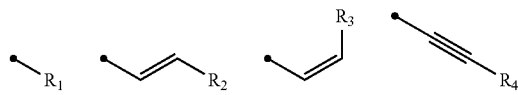

wherein, $R_1$ represents H, alkyl, aryl, heteroaryl, heterocyclyl, —CONRi-, —NRiCO—, —C(O)—, —S—, —S(O)—, or —S(O)$_2$—; and $R_2$, $R_3$, and $R_4$ each independently represent H, alkyl, alkenyl, alkynyl, aryl, heteroaryl, heterocyclyl, —CONRi-, —NRiCO—, —C(O)—, —S—, —S(O)—, or —S(O)$_2$—.

$X^2$ and $X^3$ each independently represent H, alkyl, alkenyl, alkynyl, aryl, heteroaryl, heterocyclyl, —O—, —OC(O)—, —CONRi-, —C(O)—, —S—, —S(O)—, —S(O)$_2$—, —NRi-, or —NRiCO—.

$X^4$ and $X^5$ each independently represent H, alkyl, alkenyl, alkynyl, aryl, heteroaryl, or heterocyclyl.

A-B represents CH$_2$—CH$_2$, CH═CH, CH$_2$—O, or O—CH$_2$.

Each Ri and each Rii independently represent H, alkyl, alkenyl, alkynyl, aryl, heteroaryl, or heterocyclyl.

In another embodiment, the macrolide compound of the present invention is represented by Formula (II):

[Formula 7]

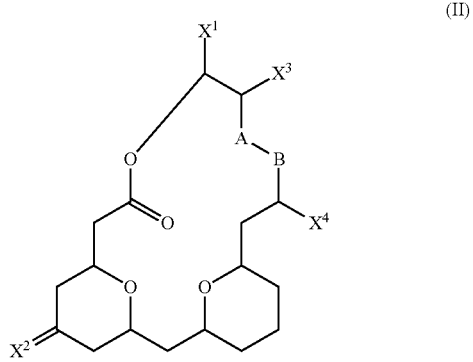

(II)

In the formula, $X^1$ represents any one of the following formulae:

[Formula 8]

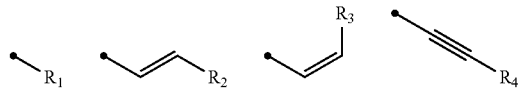

wherein, $R_1$ represents H, alkyl, aryl, heteroaryl, heterocyclyl, —CONRi-, —NRiCO—, —C(O)—, —S—, —S(O)—, or —S(O)$_2$—; and $R_2$, $R_3$, and $R_4$ each independently represent H, alkyl, alkenyl, alkynyl, aryl, heteroaryl, heterocyclyl, —CONRi-, —NRiCO—, —C(O)—, —S—, —S(O)—, or —S(O)$_2$—.

$X^2$ represents ═O, ═NC(O)—, ═NS(O)$_2$—, ═CRi-, ═CRiC(O)—, ═CRiC(O)O—, ═CRiC(O)NRii-, ═CRiC(O)S—, ═C(C(O)—)$_2$, ═C(C(O)O—)$_2$, ═C(C(O)Ri)(C(O)Rii), or ═C(C(O)ORi)(C(O)ORii).

$X^3$ and $X^4$ each independently represent H, alkyl, alkenyl, alkynyl, aryl, heteroaryl, or heterocyclyl.

A-B represents CH$_2$—CH$_2$, CH=CH, CH$_2$—O, or O—CH$_2$.
Each Ri and each Rii independently represent H, alkyl, alkenyl, alkynyl, aryl, heteroaryl, or heterocyclyl.
Analogs 1 to 8 shown in FIGS. 1A and 1B are examples of the macrolide compound of the present invention. Other examples of the macrolide compound of the present invention are shown below:
[Formula 9]
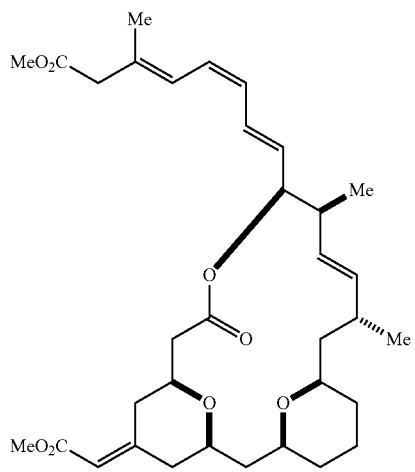
(−)-exigualide
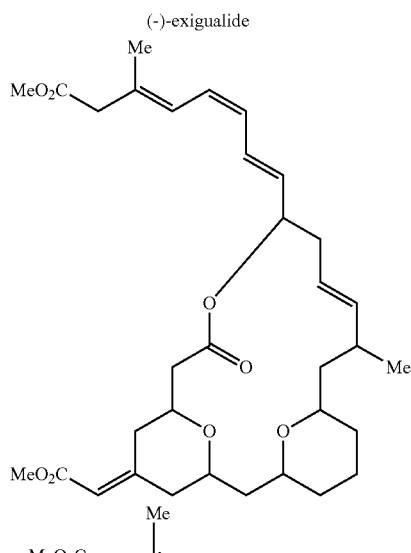
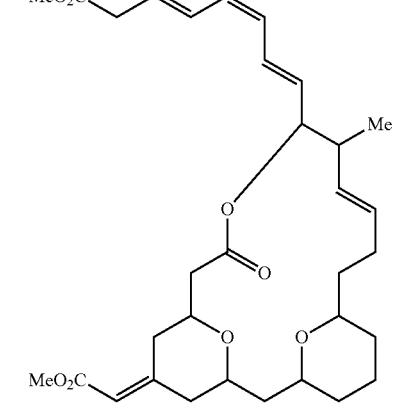
-continued
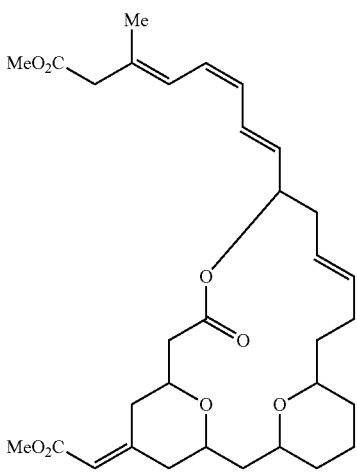
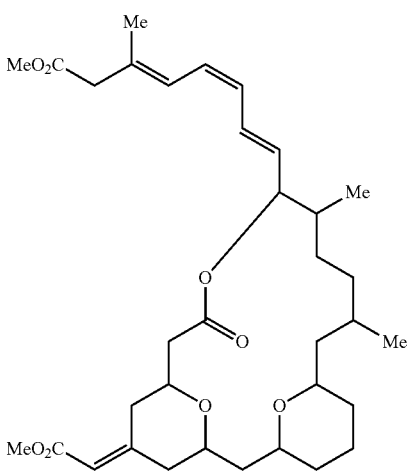
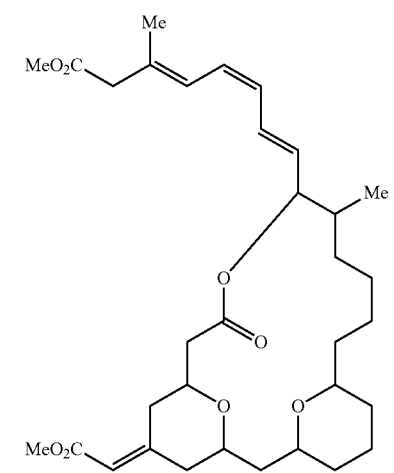

11
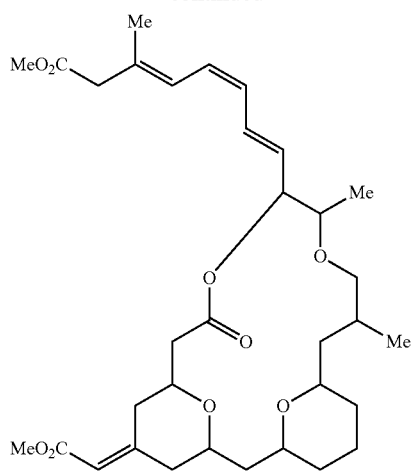
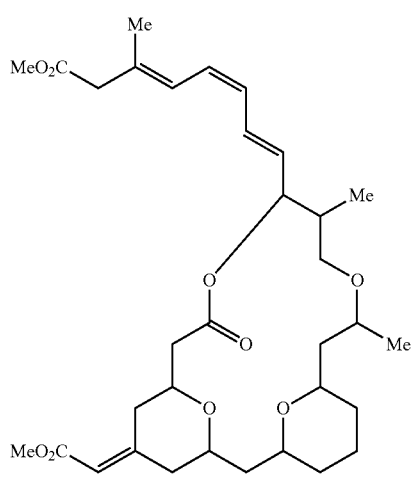
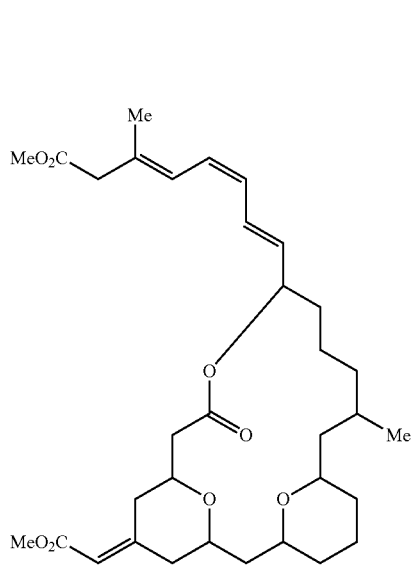
12
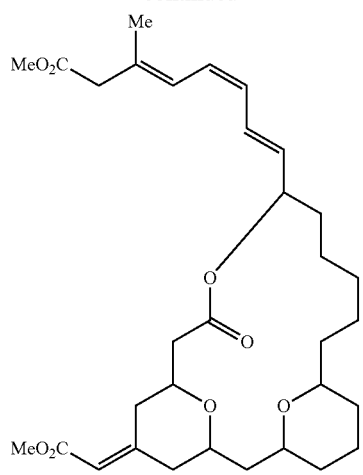
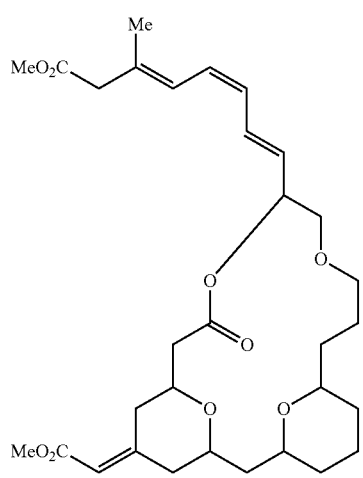
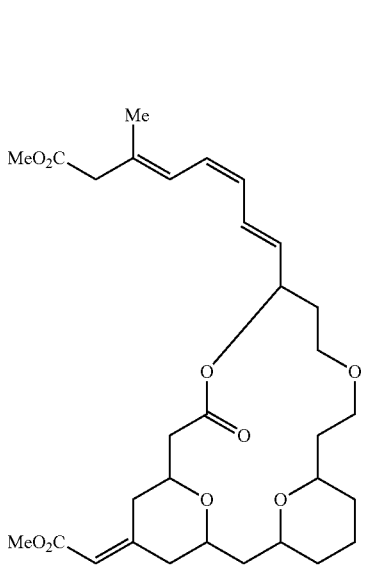

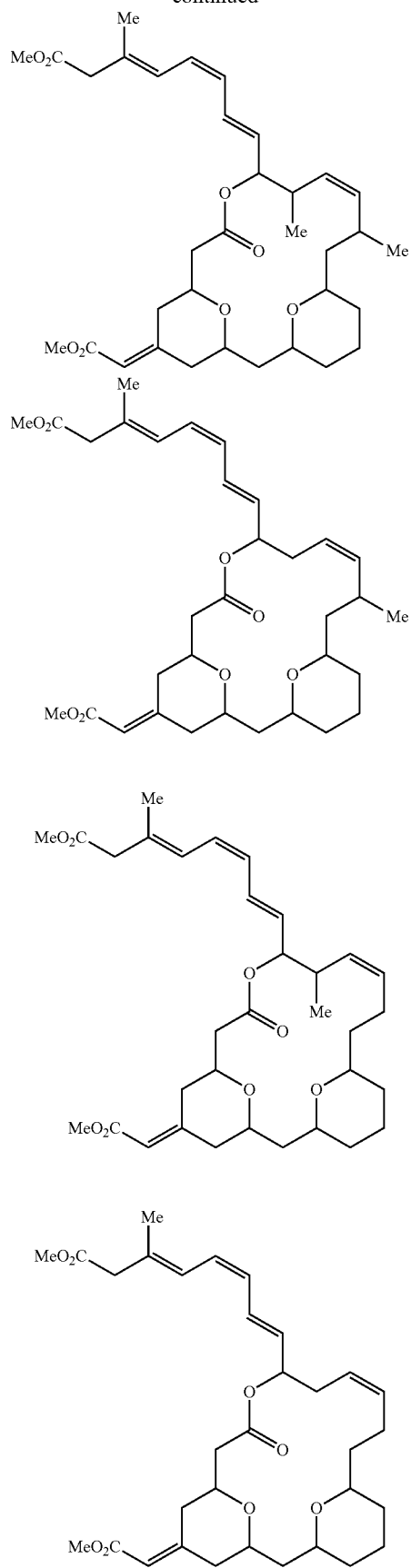
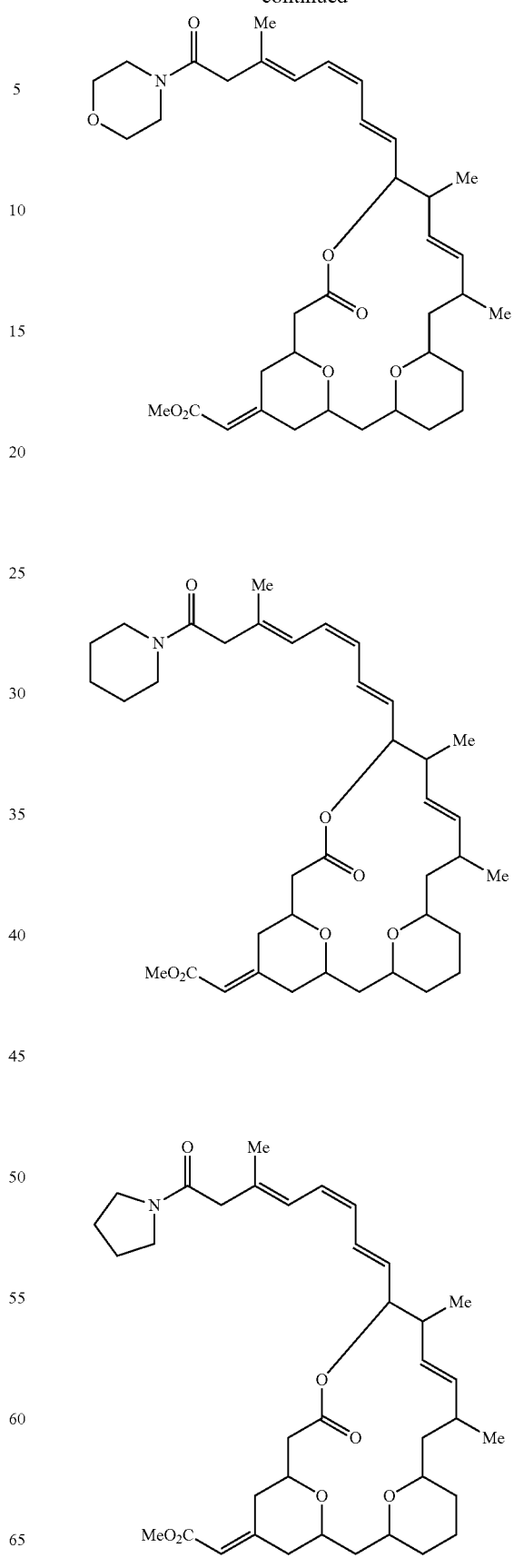

15
-continued
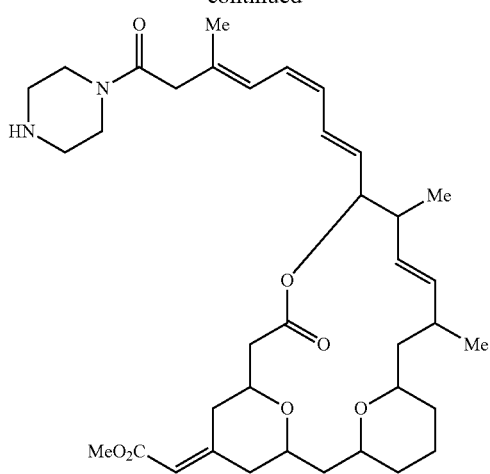
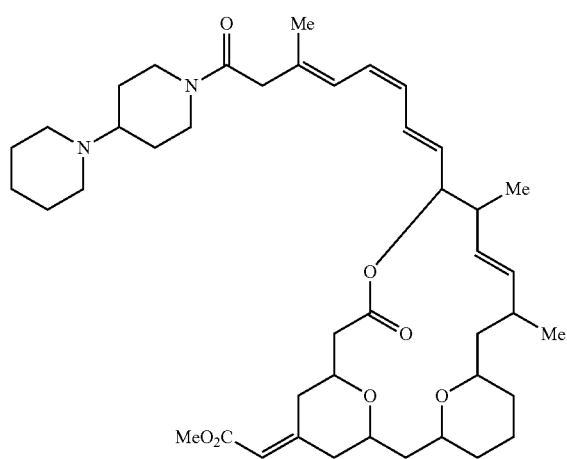
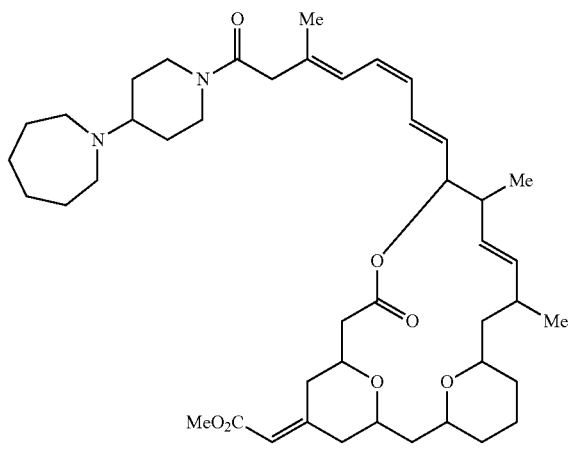
16
-continued
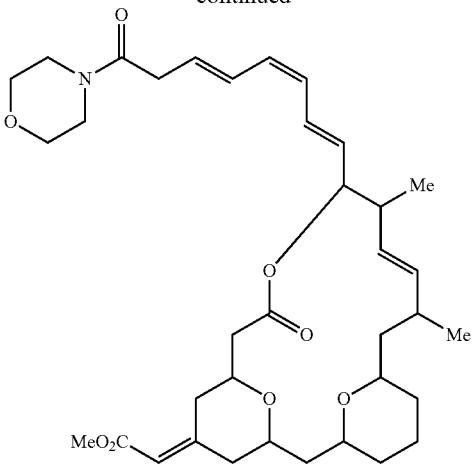
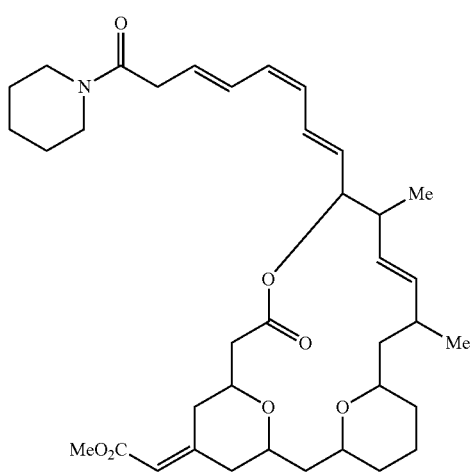
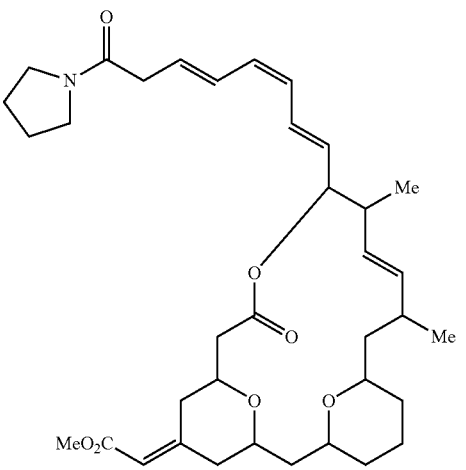

17
-continued
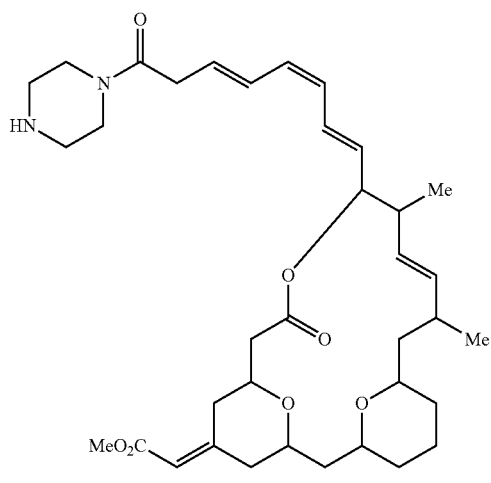
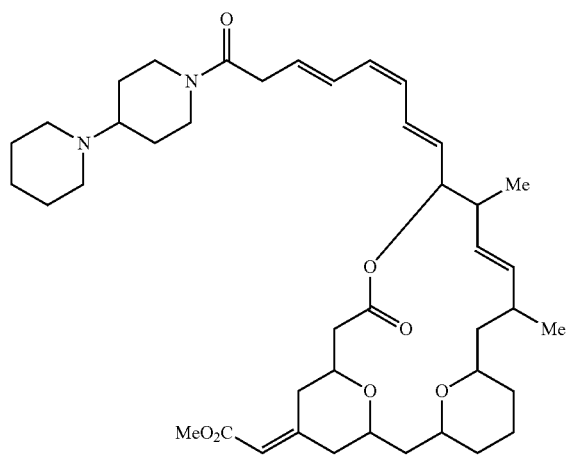
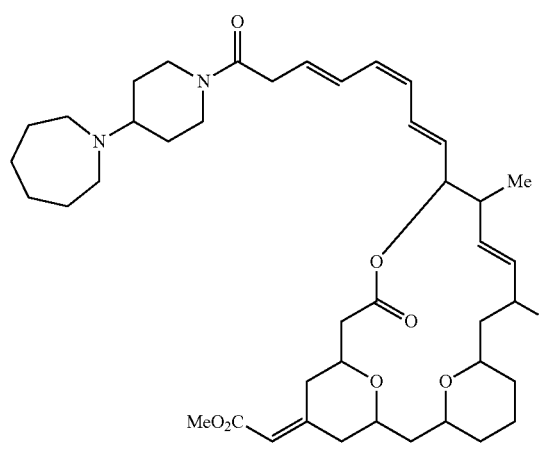
18
-continued
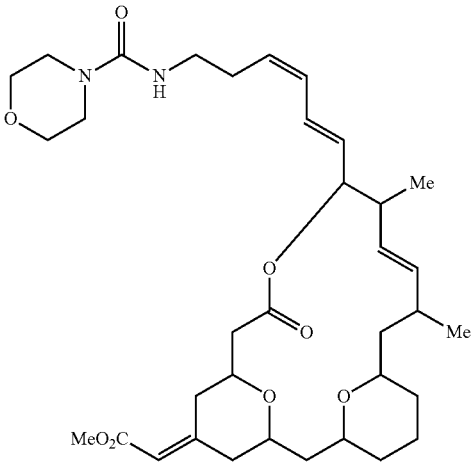
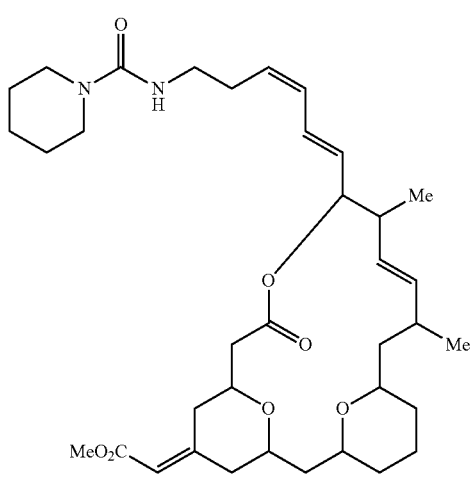
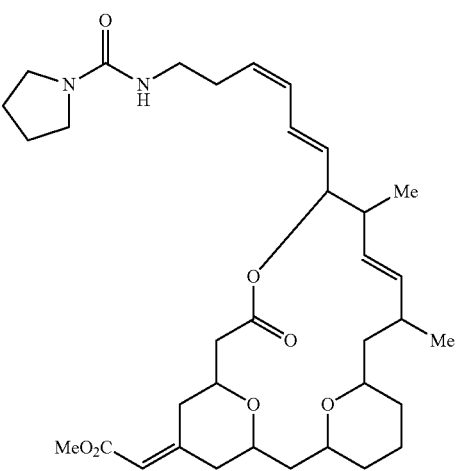

19
-continued
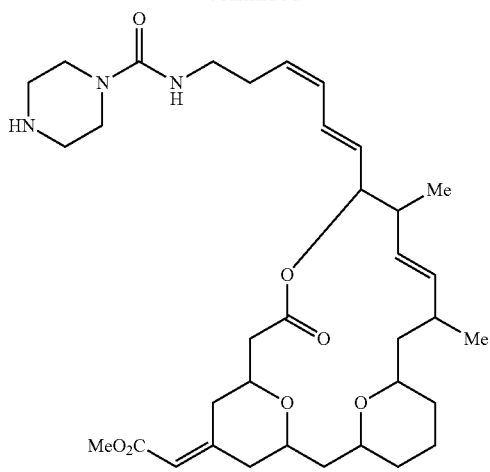
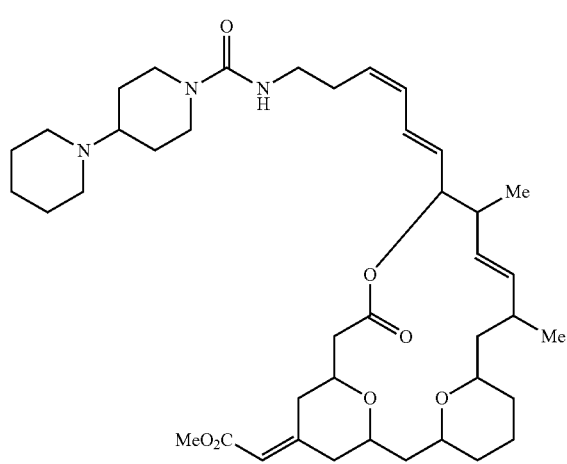
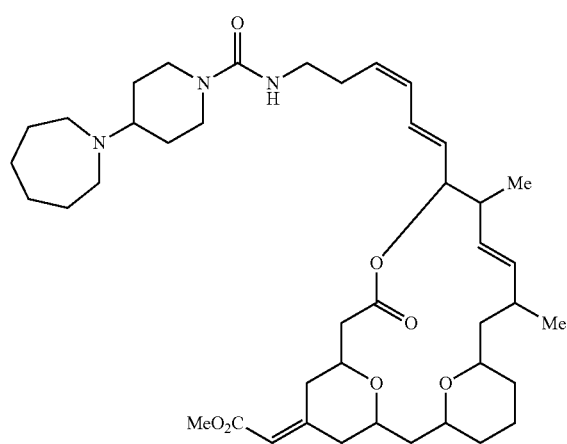
20
-continued
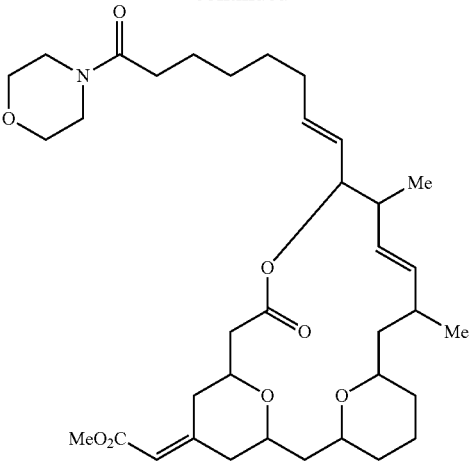
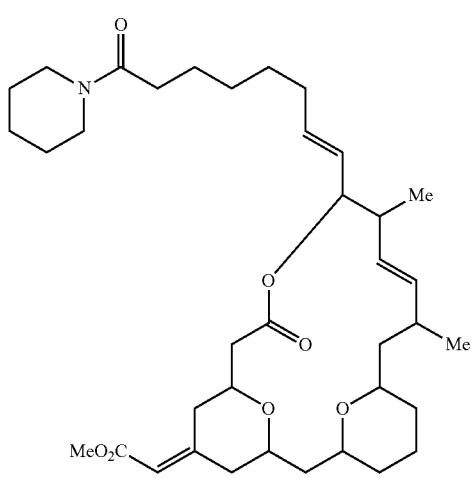
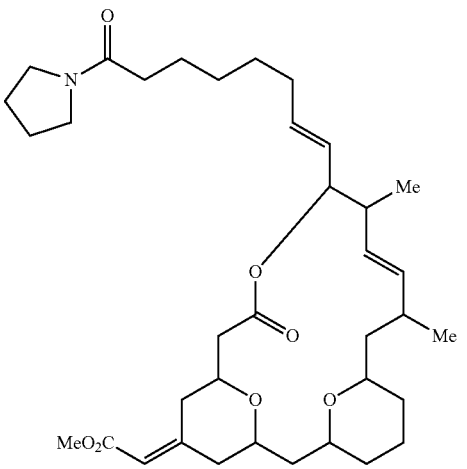

21
-continued
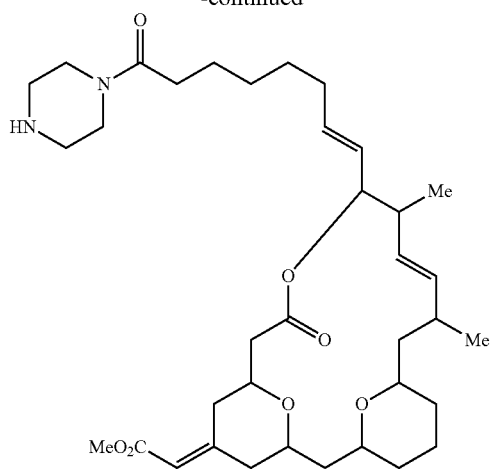
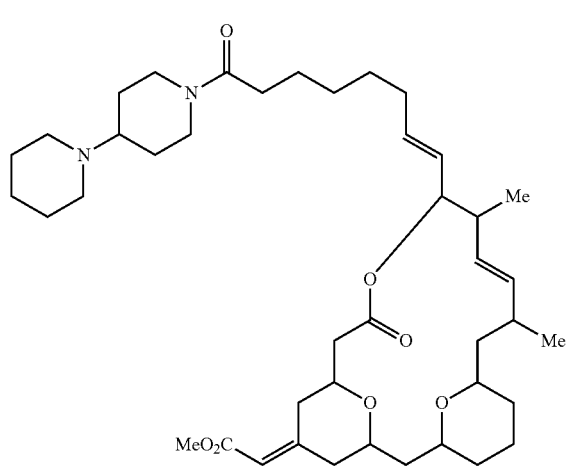
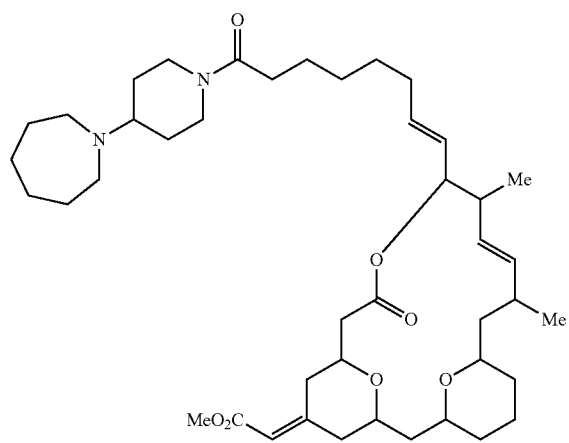
22
-continued
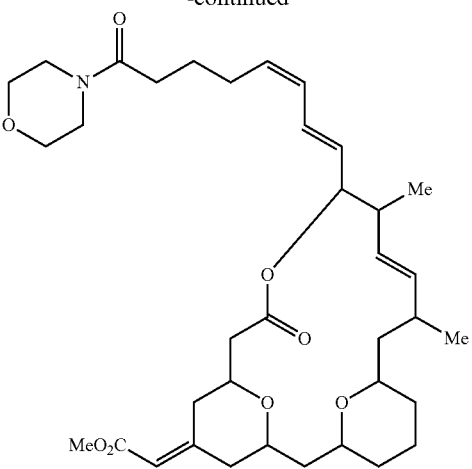
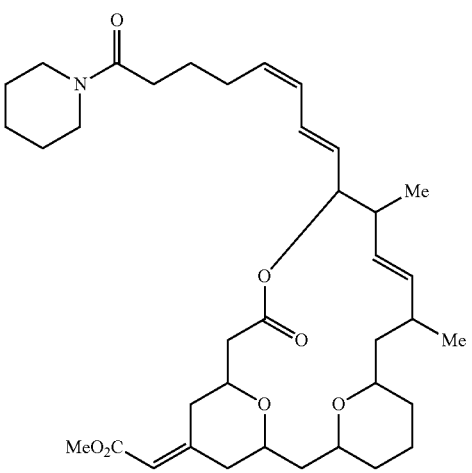

23
-continued
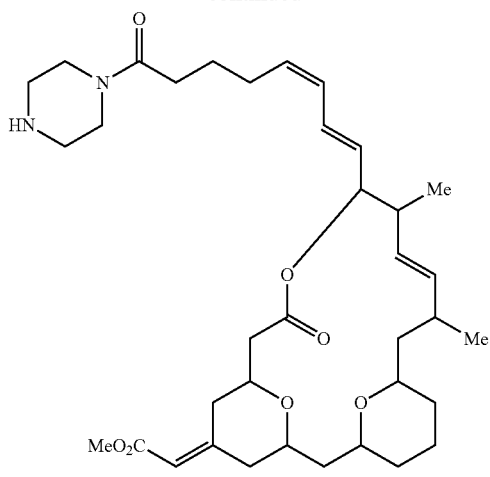
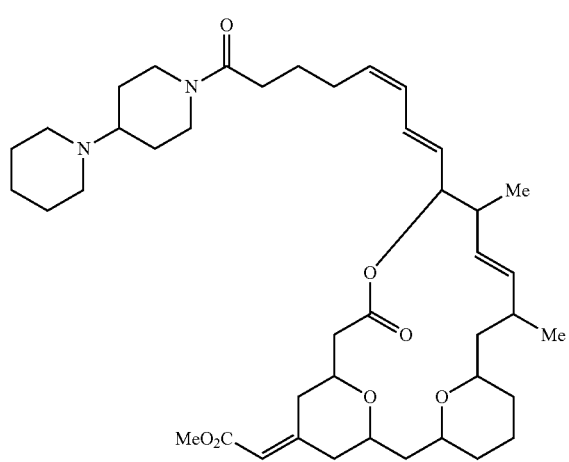
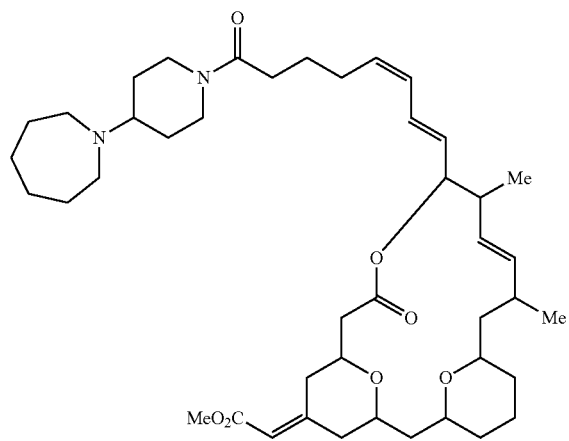
24
-continued
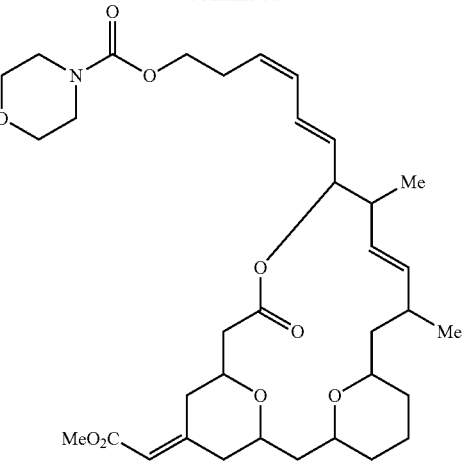
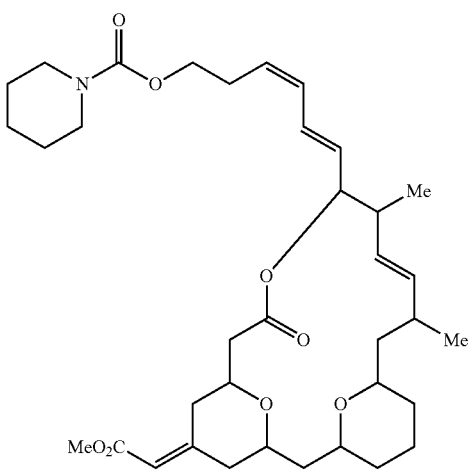
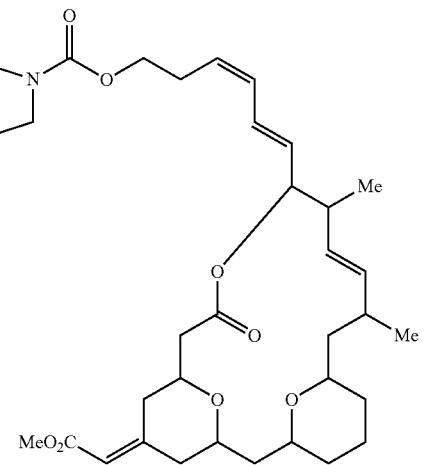

25
-continued
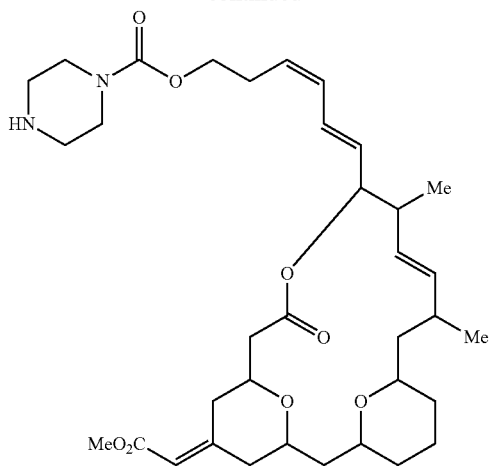
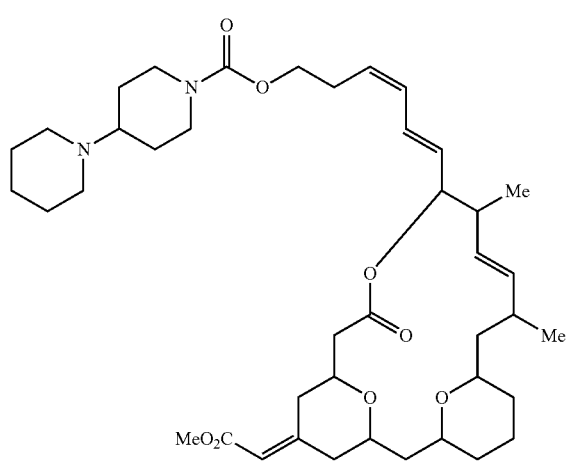
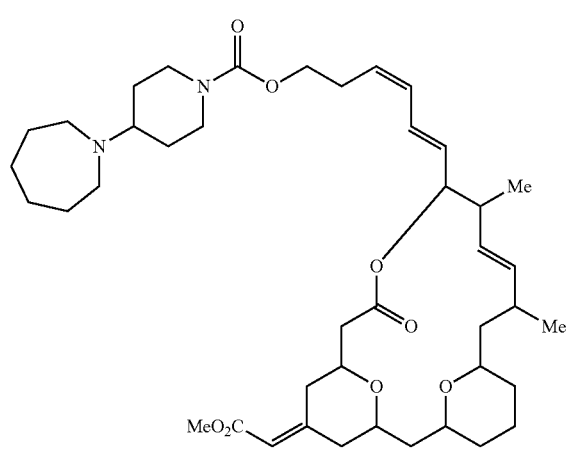
26
-continued
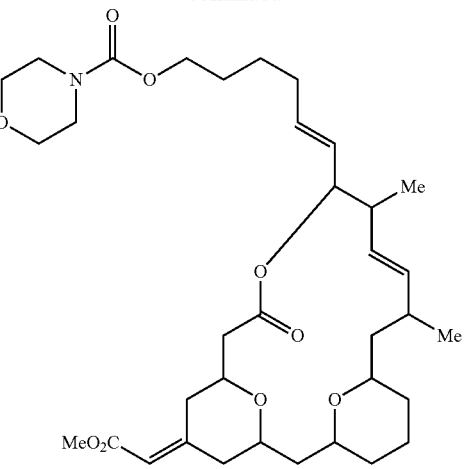
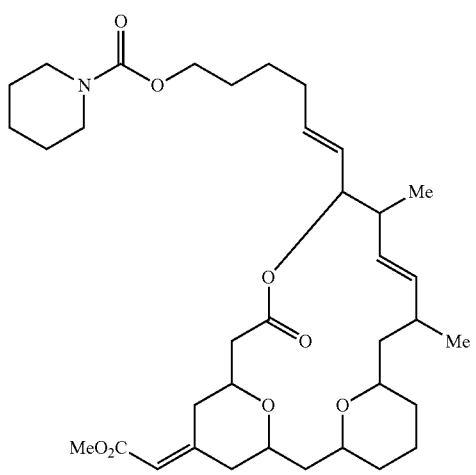
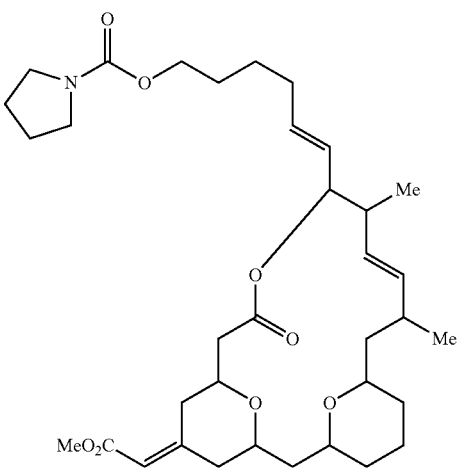

27
-continued
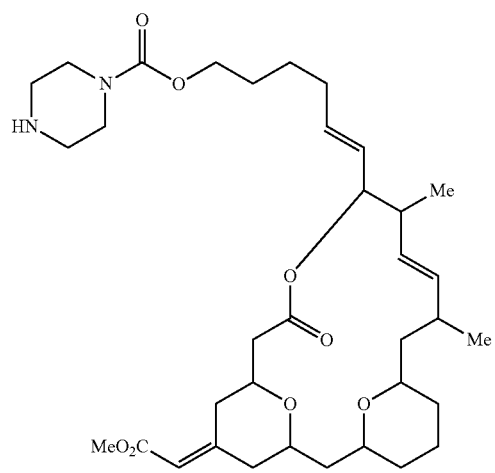
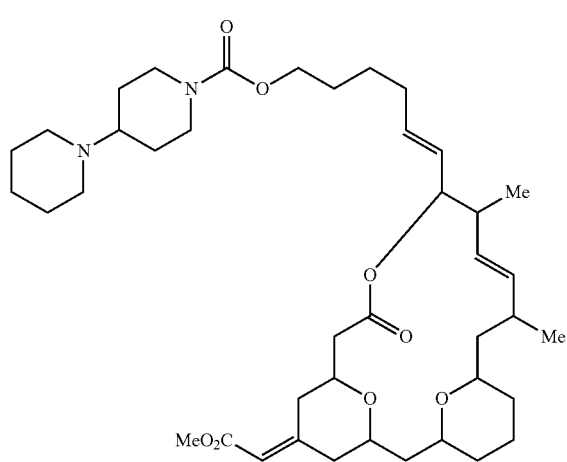
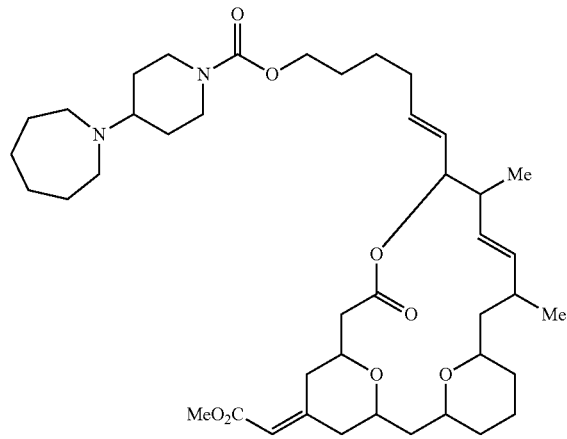
28
-continued
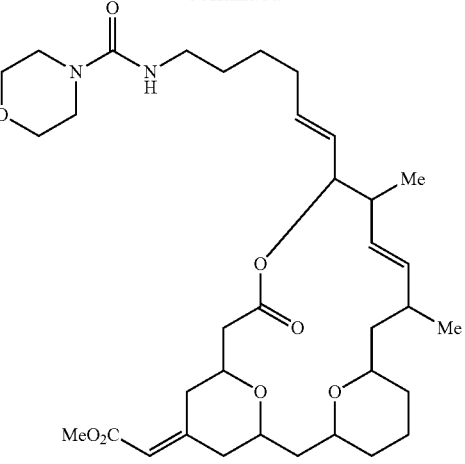
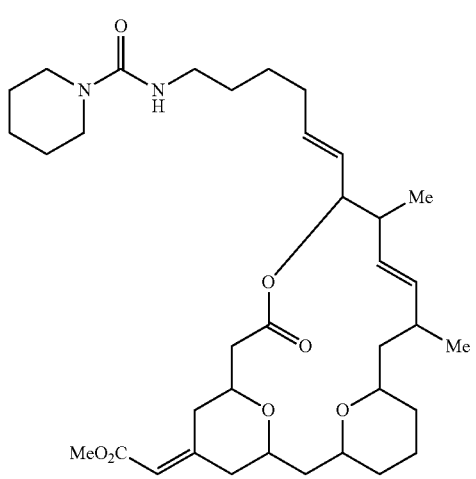
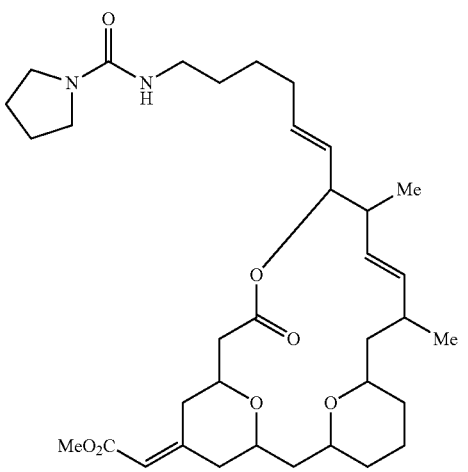

29
-continued
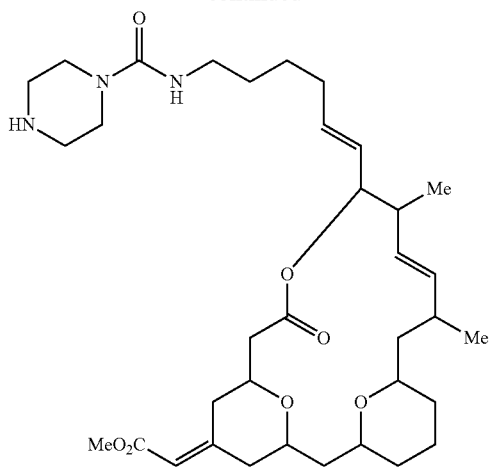
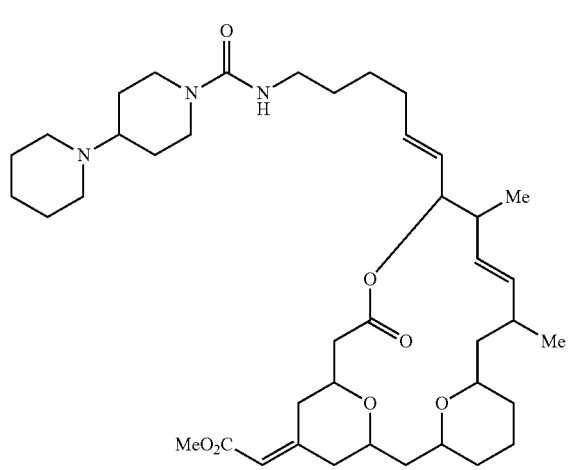
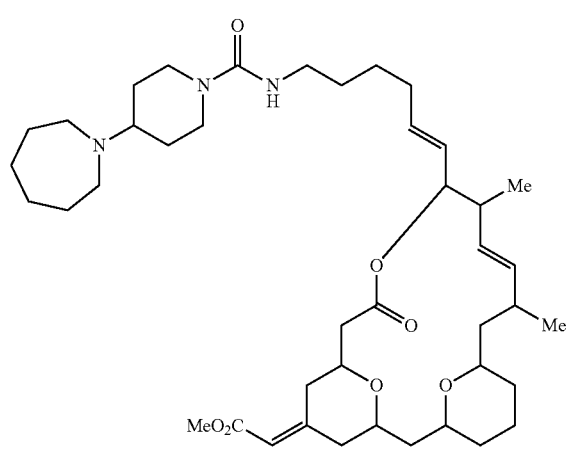
30
-continued
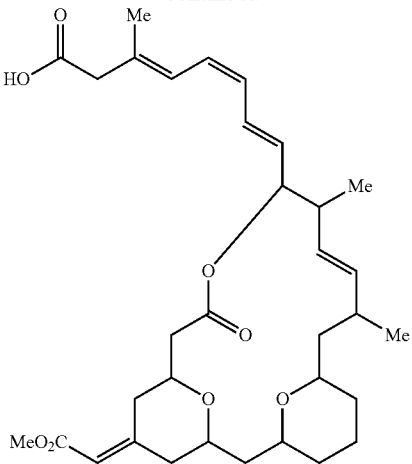
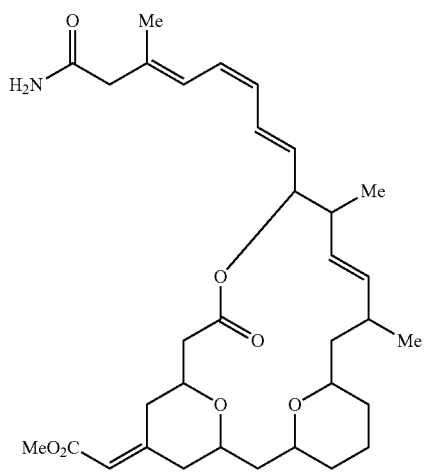
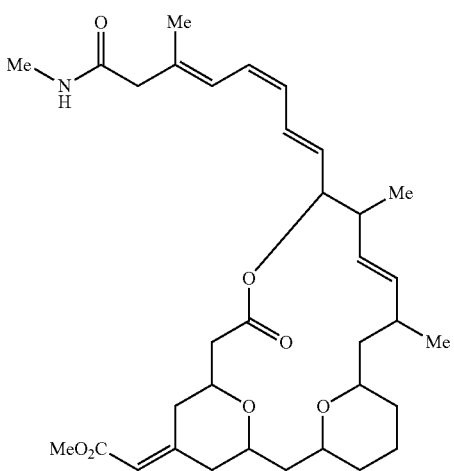

31
-continued
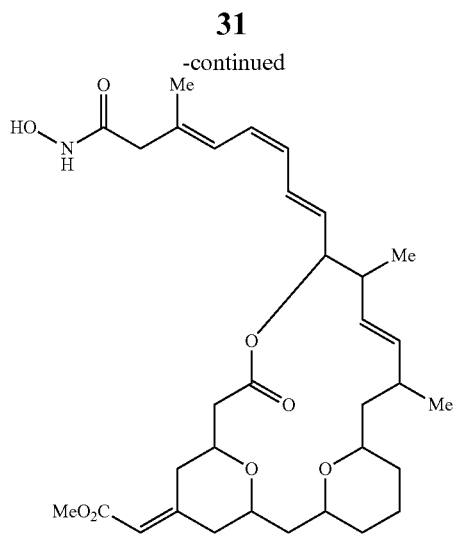
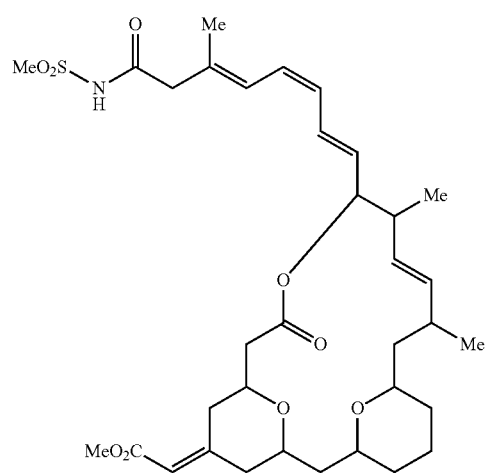
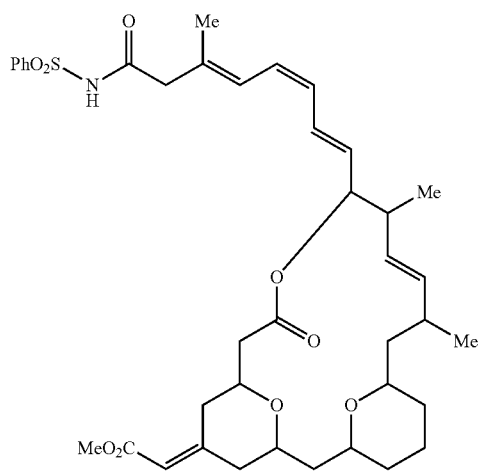
32
-continued
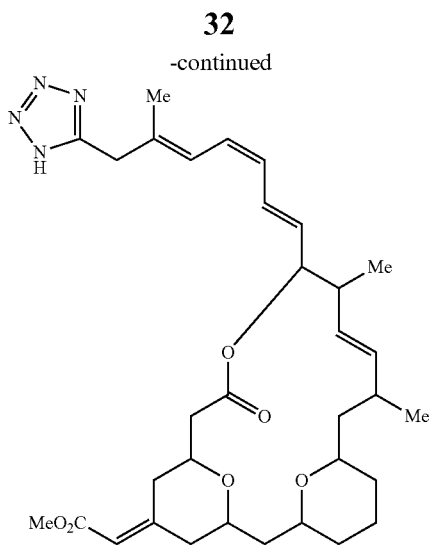
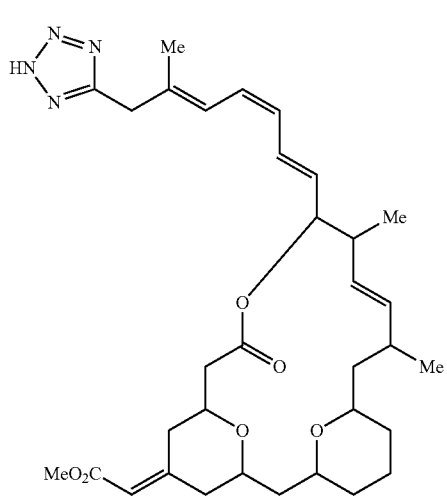
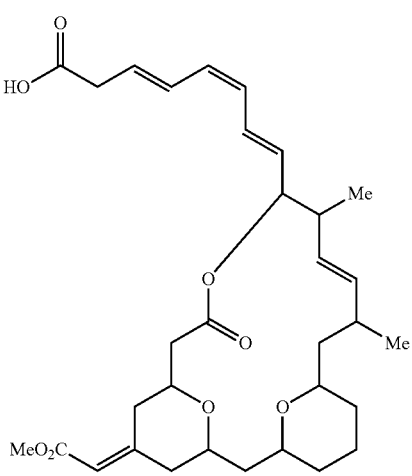

33
-continued
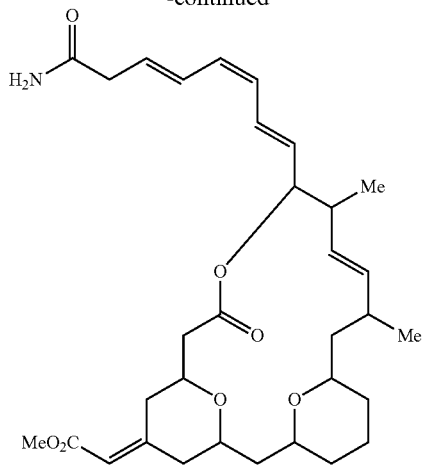
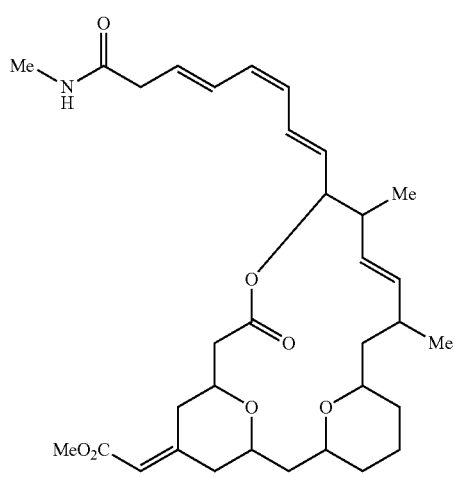
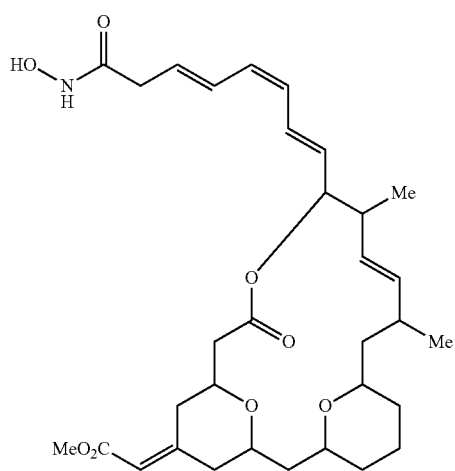
34
-continued
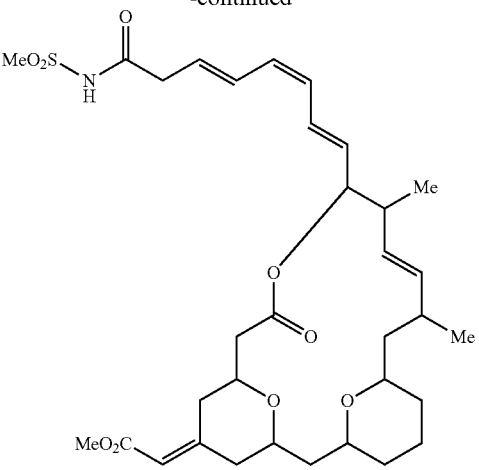
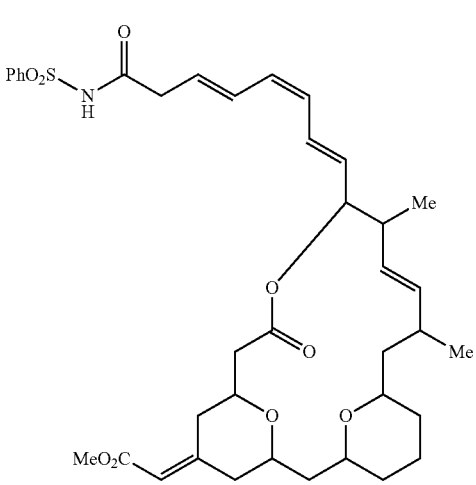
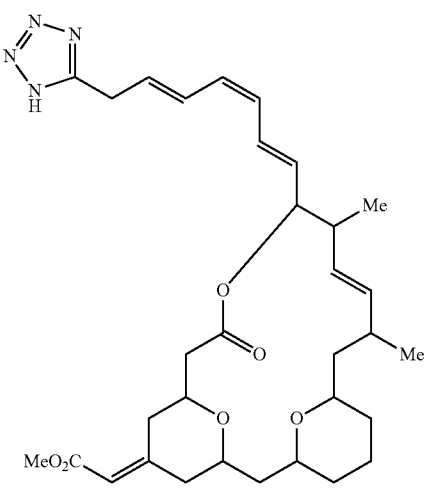

35
-continued
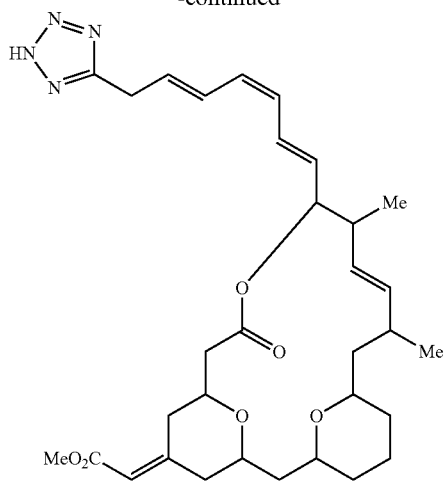
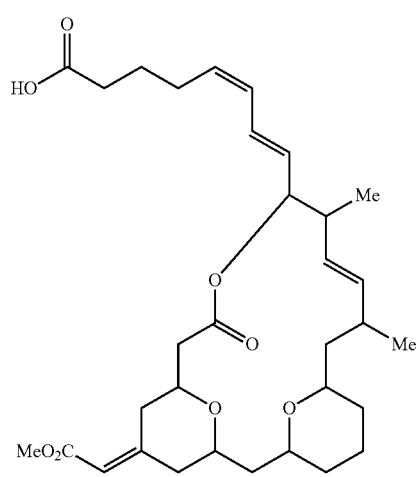
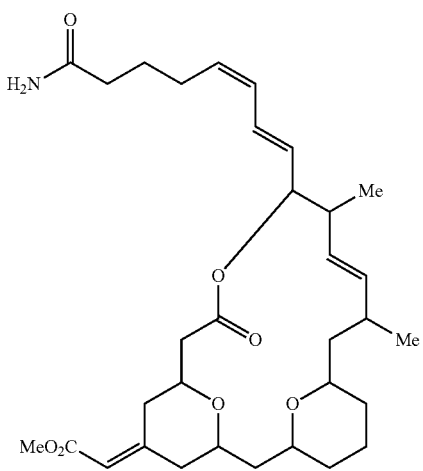
36
-continued
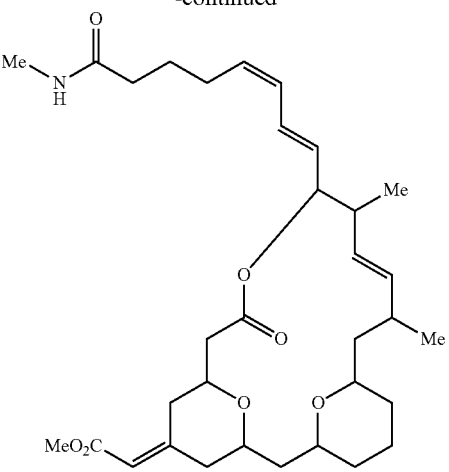
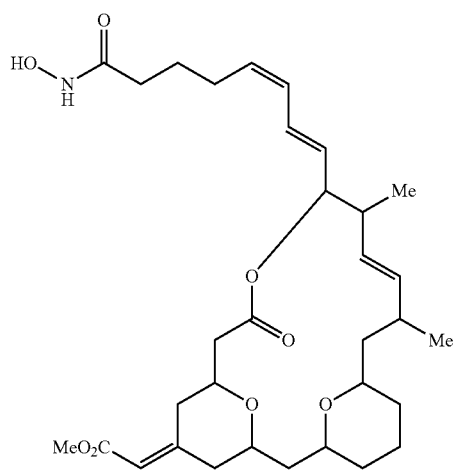
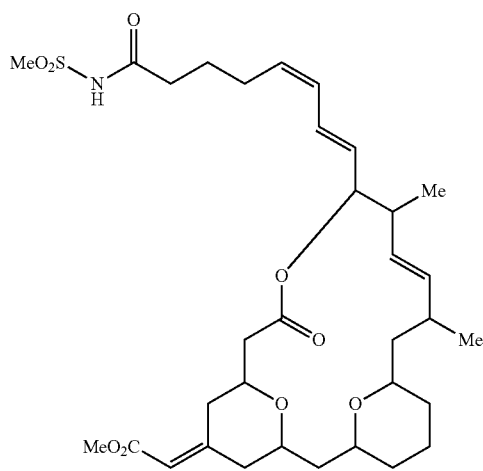

37
-continued
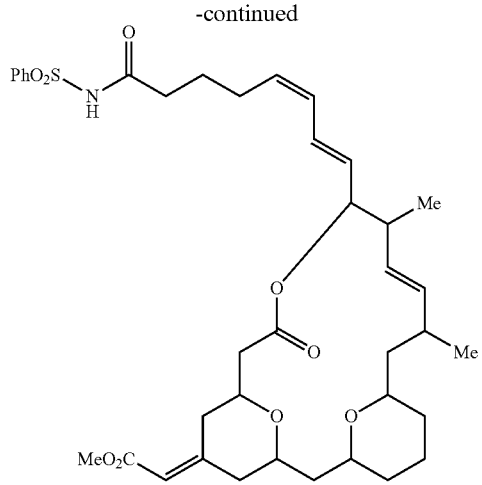
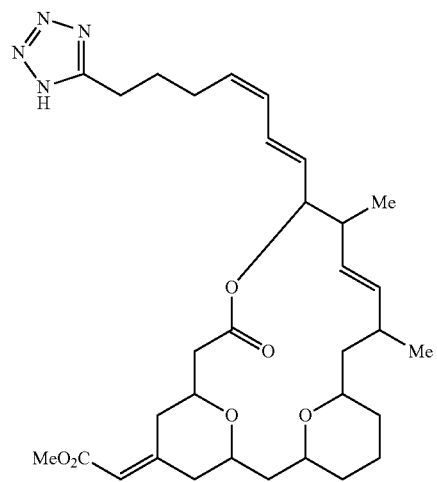
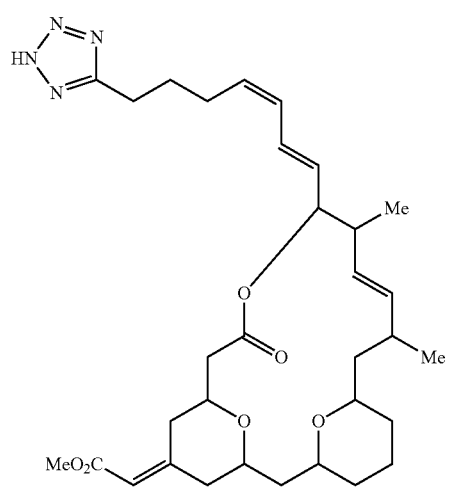 [SMILES: COC(=O)/C=C1\CC2CC(=O)OC(/C=C/CCCCCc3nn[nH]n3)C(C)/C=C/C(C)CC3CCCC(CC(C1)O2)O3]
38
-continued
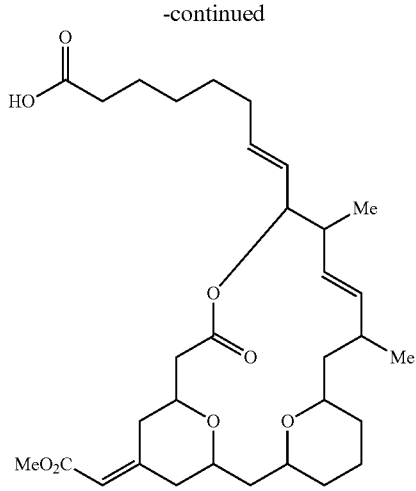
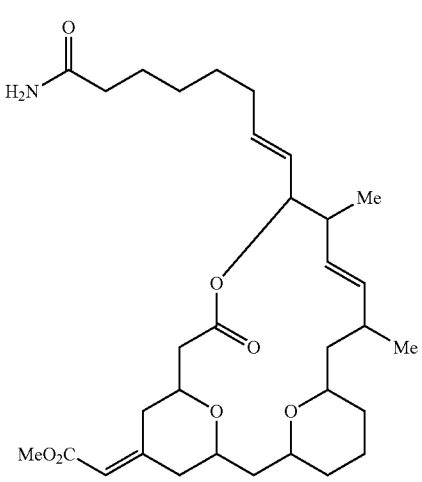
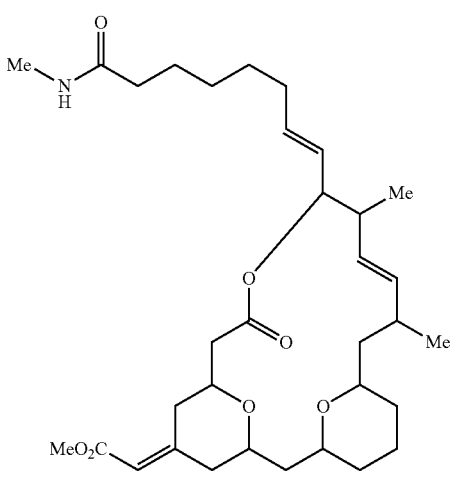

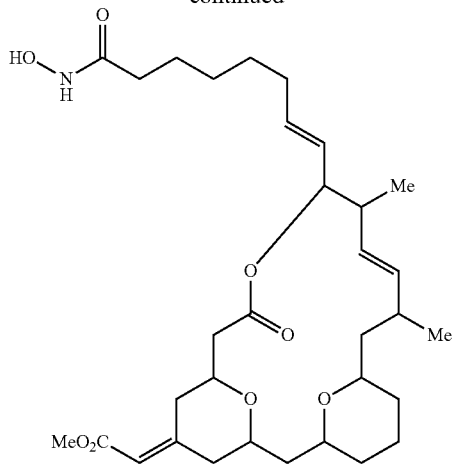

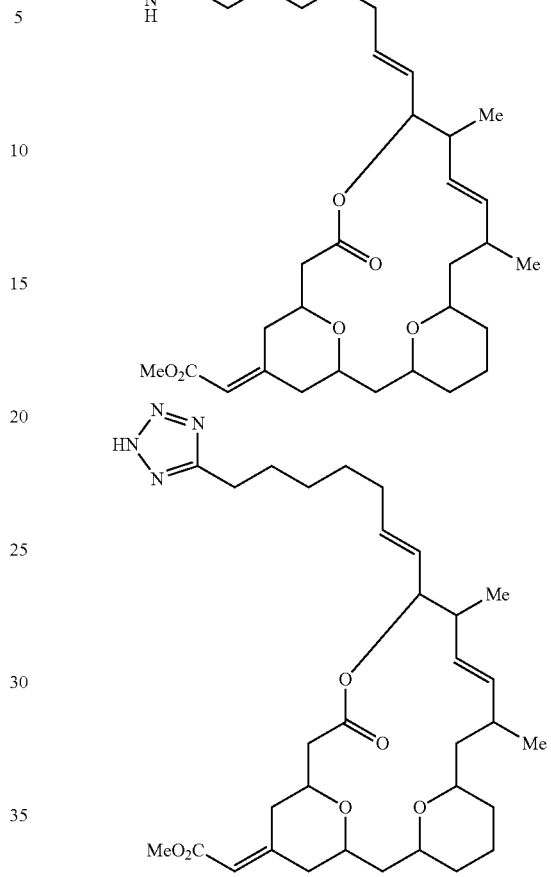

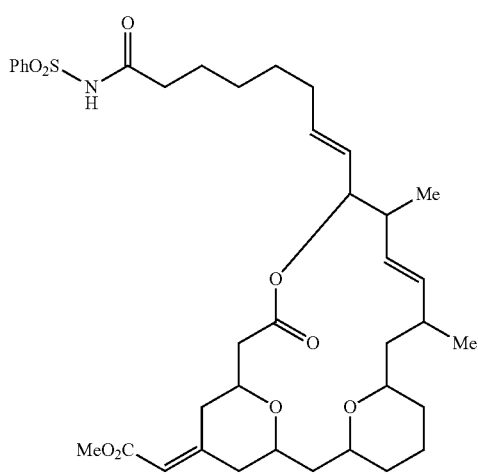

3. Synthesis of Macrolide Compound of the Present Invention

The macrolide compound of the present invention can be produced, for example, by synthesizing (−)exiguolide by the method established by the present inventors (Fuwa H. et al., Org. Lett., 12(3), 2010, pp. 584-587: Reference Example) and introducing a desired substituent to the (−)exiguolide by a known method in the art.

That is, (−)exiguolide can be synthesized by (i) constructing two tetrahydropyrane rings through an intramolecular conjugate addition reaction and a reductive etherification, (ii) forming a large-membered ring lactone skeleton through macrolactonization or ring-closing metathesis, and (iii) introducing a side chain through a Suzuki-Miyaura reaction.

Herein, the (i) stereoselective construction of the tetrahydropyrane rings by an intramolecular conjugate addition reaction and a reductive etherification corresponds to a series of steps of converting compound 10 in Scheme 4 of Reference Example described below into compound 9 and then into compound 4. The (ii) construction of a large-membered ring lactone structure by macrolactonization or ring-closing metathesis corresponds to a step of converting compound 25 in Scheme 6 of Reference Example into compound 22 and a step of converting compound 5 in Scheme 5 into compound 22. The (iii) stereoselective introduction of a side chain by a Suzuki-Miyaura reaction corresponds to a step of converting compound 3 in Scheme 6 into compound 1.

4. Cell Growth Inhibitor

Cells proliferate through a cell cycle. The cell cycle is a process composed of growth of a daughter cell generated by cell division to a mother cell and cell division of the mother cell to generate daughter cells. The cell cycle can be divided into a G0 phase, a G1 phase, an S phase, a G2 phase, and an M phase. The G0 phase is a resting phase of the cell where the cell is not actively preparing itself for growth; the G1 phase is a phase of starting preparation for cell growth; the S phase is a synthesis phase for replicating DNA; the G2 phase is a phase of cell growth from DNA synthesis till occurrence of mitosis; and the M phase is the mitotic phase. The cell cycle proceeds by cooperation with various molecules.

It is important to know in which stage of the cell cycle each drug acts, from the point of determining the effect of the drug on cell growth. In some carcinomas, a molecule that accelerates the cell cycle is abnormally enhanced. For example, if it is possible to specifically inhibit a molecule that accelerates the transition from the G1 phase to the S phase, the abnormally enhanced cell cycle can be stopped to inhibit cell growth.

As described above, the "cell growth inhibitor" of the present invention is a drug that inhibits growth of cells. The macrolide compound of the present invention has a possibility of inhibiting cell growth by stopping the cell cycle.

The "cell growth inhibitor" of the present invention contains an effective dose of a compound represented by Formula (I) or (II) or a pharmaceutically acceptable salt thereof.

Herein, the term "effective dose" means a sufficient amount for inhibiting the growth of target cells. In the case of using the cell growth inhibitor as a therapeutic agent, the term "effective dose" means a sufficient amount for inhibiting the growth of target cells only without significantly affecting normal cells. The term "effective dose" also includes a sufficient amount of the compound of the present invention for modulating (e.g., activating or inhibiting, preferably inhibiting) ligase activity either in vitro or in vivo.

Preferred examples of the target cell are cancer cells. The cancer may be any cancer, and examples thereof include pancreatic cancer, colon cancer, liver cancer, brain cancer, lung cancer, squamous cell carcinoma, bladder cancer, gastric cancer, pancreatic cancer, prostatic cancer, kidney cancer, colorectal cancer, breast cancer, head cancer, neck cancer, esophageal cancer, gynecological cancer, thyroid cancer, lymphoma, chronic leukemia, and acute leukemia.

It has been confirmed that the macrolide compound of the present invention shows a remarkable cell growth-inhibiting effect on specific cancer cells only and does not significantly affect normal cells. Such specific cancer cells are, for example, lung cancer cells.

The cell growth inhibitor of the present invention may be used in vitro or in vivo. In the case of using the inhibitor in vivo, the administration may be oral or parenteral. Parenteral administration is particularly preferred, and specific examples thereof include injection, transnasal administration, pulmonary administration, and transdermal administration. Examples of the injection include intravenous injection, intramuscular injection, intraperitoneal injection, and subcutaneous injection. The route of administration can be appropriately selected depending on the age and symptoms of a patient.

The dose of the cell growth inhibitor of the present invention is appropriately determined depending on the purpose, the route of administration, etc. In inhibition of cell growth in vitro, the dose is appropriately controlled depending on the culture scale. In administration to human, for example, the dose in each administration can be selected in the range of 0.0001 to 1000 mg per 1 kg of body weight. Alternatively, for example, a dose in each patient can be selected in the range of 0.001 to 100000 mg/body. However, the cell growth inhibitor of the present invention is not limited to these doses.

The cell growth inhibitor of the present invention may contain a pharmaceutically acceptable carrier and additive. Examples of the carrier and additive include, but not limited to, surfactants, fillers, coloring agents, flavoring agents, preservatives, stabilizers, buffers, suspending agents, isotonizing agents, binding agents, disintegrators, lubricants, fluidizing agents, and corrigents. Other conventional carriers can be also used appropriately, and specific examples thereof include light anhydrous silicic acid, lactose, crystalline cellulose, mannitol, starch, calcium carmellose, sodium carmellose, hydroxypropyl cellulose, hydroxypropylmethyl cellulose, polyvinylacetal diethylaminoacetate, polyvinylpyrrolidone, gelatin, middle-chain fatty acid triglyceride, polyoxyethylene hydrogenated castor oil 60, sucrose, carboxymethyl cellulose, corn starch, and inorganic salts.

5. Anticancer Drug

The present invention provides an anticancer drug containing a therapeutically effective dose of a compound represented by Formula (I) or (II) or a pharmaceutically acceptable salt thereof.

Here, the term "effective dose" means a sufficient amount of the compound of the present invention for destruction, remedy, inhibition, or removal of primary, local, or metastatic cancer cells or cancer tissue; delay or minimization of the progress of cancer; or provision of advantages for treating cancer. The term "effective dose" also includes a sufficient amount of the compound of the present invention for inducing death of cancer or neoplasm cells. In addition, the term "effective dose" includes a sufficient amount of the compound of the present invention for modulating (e.g., activating or inhibiting, preferably inhibiting) ligase activity either in vitro or in vivo.

The cancer to be treated may be any cancer, and examples thereof include pancreatic cancer, colon cancer, liver cancer, brain cancer, lung cancer, squamous cell carcinoma, bladder cancer, gastric cancer, pancreatic cancer, prostatic cancer, kidney cancer, colorectal cancer, breast cancer, head cancer, neck cancer, esophageal cancer, gynecological cancer, thyroid cancer, lymphoma, chronic leukemia, and acute leukemia.

The anticancer drug of the present invention is predicted to be particularly effective on lung cancer from the results of a drug sensitivity test.

The anticancer drug of the present invention can be administered either orally or parenterally. Parenteral administration is particularly preferred, and specific examples thereof include injection, transnasal administration, pulmonary administration, and transdermal administration. In injection administration, systemic or local administration can be performed by, for example, intravenous injection, intramuscular injection, intraperitoneal injection, or subcutaneous injection. The route of administration can be appropriately selected depending on the age and symptoms of a patient.

The dose in each administration can be selected in the range of 0.0001 to 1000 mg, preferably 0.001 to 100 mg, and more preferably 0.01 to 10 mg, per 1 kg of body weight. Alternatively, for example, a dose in each patient can be selected in the range of 0.001 to 100000 mg/body, preferably 0.01 to 1000 mg/body, and more preferably 0.1 to 100 mg/body. However, the anticancer drug of the present invention is not limited to these doses.

The anticancer drug of the present invention can be formulated in accordance with a common method (e.g., Remington's Pharmaceutical Science, latest edition, Mark Publishing Company, Easton, U.S.A.) and may contain a pharmaceutically acceptable carrier and additive. Examples of the carrier and additive include, but not limited to, surfactants, fillers, coloring agents, flavoring agents, preservatives, stabilizers, buffers, suspending agents, isotonizing agents, binding agents, disintegrators, lubricants, fluidizing agents, and corrigents. Other conventional carriers can be also used appropriately, and specific examples thereof include light anhydrous silicic acid, lactose, crystalline cellulose, mannitol, starch, calcium carmellose, sodium carmellose, hydroxypropyl cellulose, hydroxypropylmethyl cellulose, polyvinylacetal diethylaminoacetate, polyvinylpyrrolidone, gelatin, middle-chain fatty acid triglyceride, polyoxyethylene hydrogenated castor oil 60, sucrose, carboxymethyl cellulose, corn starch, and inorganic salts.

The mechanism and the phase of the activity of the anticancer drug of the present invention are likely different from those of known drugs. Specifically, a mechanism of stopping the cell cycle at the G1 phase is predicted. It is therefore expected to show advantageous effects in combination with other anticancer drugs or effects of overcoming multiple drug resistance.

EXAMPLES

The present invention will now be specifically described by Reference Examples, Examples, and Test Examples, but is not limited to these Examples and Test Examples.

Reference Example

Total Synthesis of Exiguolide (Compound I)

1. Synthesis Plan

The (E,Z,E)-triene side chain of compound 1 was stereoselectively introduced at the final stage of the total synthesis by a Suzuki-Miyaura reaction of vinylboric acid ester 2 and vinyl iodide 3 (Scheme 1). In construction of the macrolactone ring of compound 3, route A via ring-closing metathesis (RCM) using methylene bis(tetrahydropyran) 4 as a common synthetic intermediate and route B via macrolactonization were designed. That is, route A was expected that compound 3 can be prepared by RCM of triene 5 and that compound 5 can be induced from compound 4 through esterification. In route B, it was expected that compound 3 can be prepared through macrolactonization of hydroxycarboxylic acid 7 by a Yamaguchi method and that compound 7 can be synthesized from compound 4 through stereoselective formation of a C16-C17 double bond by a Julia-Kocienski reaction. It was believed that common intermediate 4 can be prepared by reductive etherification of silyloxyketone 9 and that silyloxyketone 9 can be synthesized by an intramolecular conjugate addition reaction of hydroxyenone 10. Compound 10 was synthesized by an olefin cross metathesis (CM) reaction of hydroxyolefin 11 and enone 12, which are non-cyclic segments that can be easily prepared.

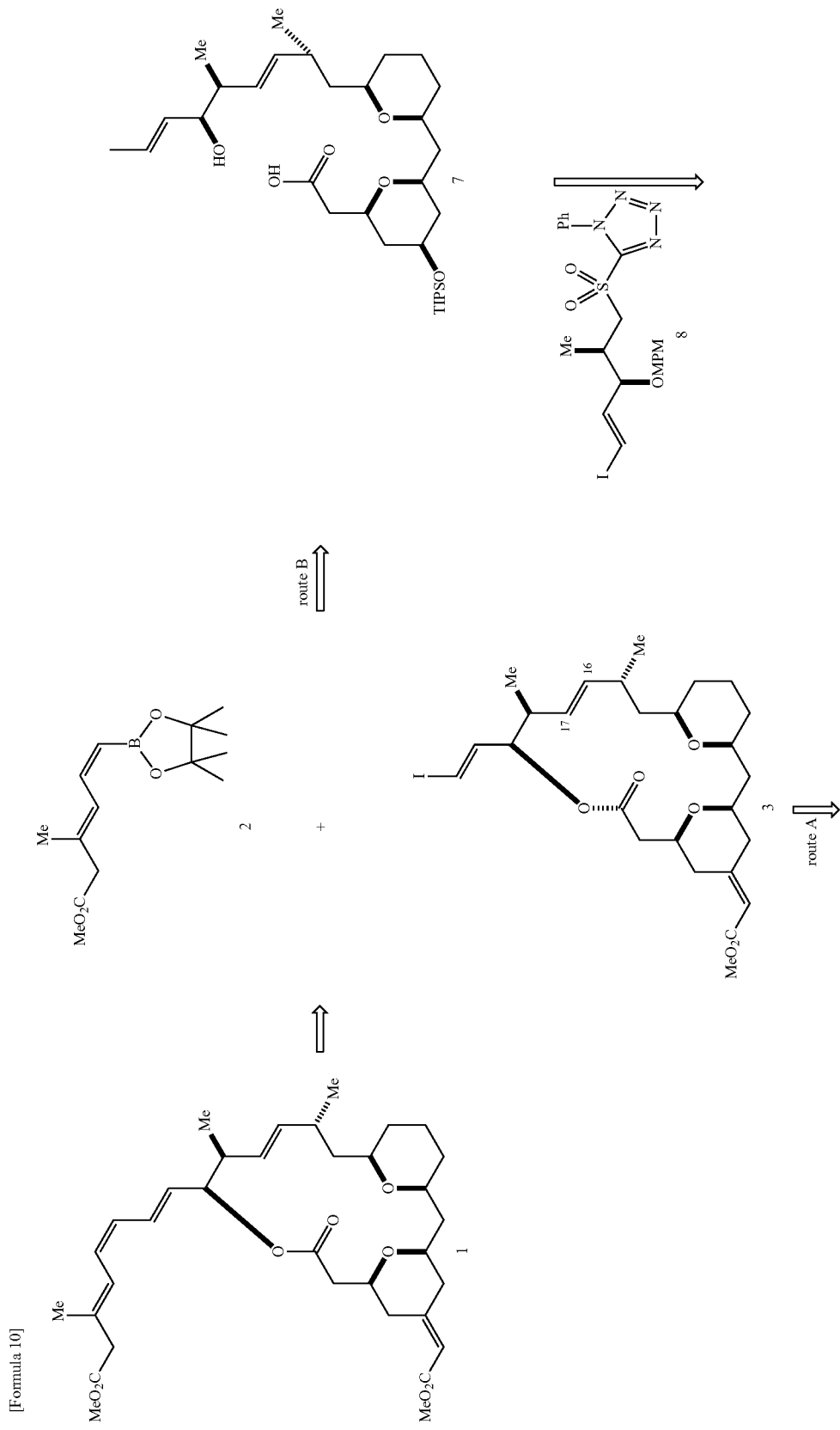

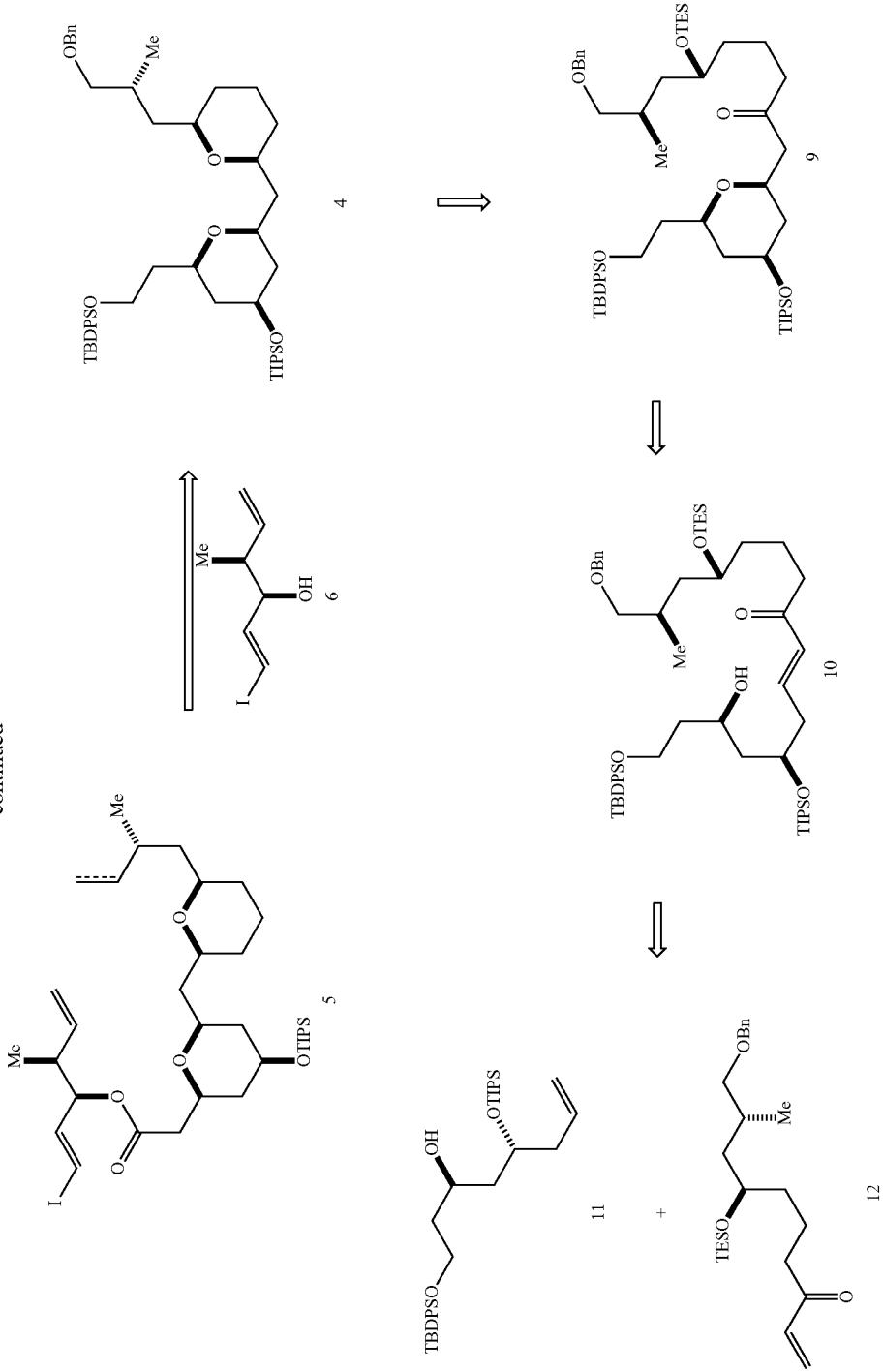

2. Synthesis of Hydroxyolefin 11

Compound 11 was synthesized using homoallylic alcohol 13 prepared by Keck asymmetric allylation as a starting material (Scheme 2). The hydroxy group of compound 13 was protected and was then induced into aldehyde 14 by oxidatively cleaving the double bond. Compound 14 was diastereoselectively allylated by allyltrimethylsilane in the presence of a magnesium bromide-diethyl ether complex to give homoallylic alcohol 15 having a desired stereochemistry as a single stereoisomer. Subsequent conversion of the protecting group gives hydroxyolefin 11.

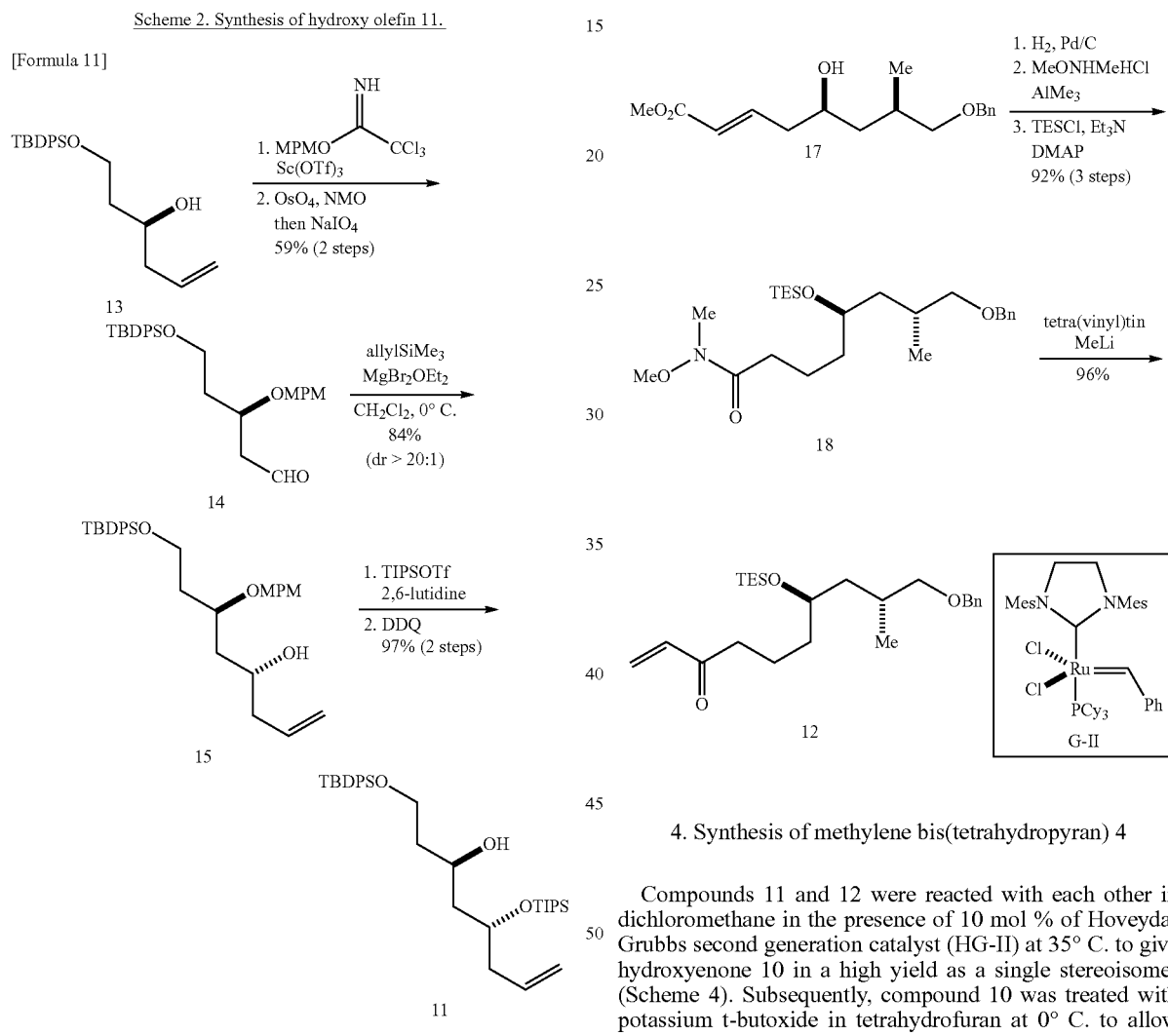

3. Synthesis of Enone 12

Compound 12 was synthesized using aldehyde 16, which is easily available from (S)-Roche ester through five stages, as a starting material (Scheme 3). Compound 16 was homologated by Brown asymmetric allylation and subsequent CM using a Grubbs second generation catalyst (G-II) to induce unsaturated ester 17. After catalytic reduction of compound 17, the resulting ester was converted into Weinreb amide, and the free hydroxy group was further silylated to give compound 18. Compound 18 was reacted with vinyl lithium to synthesize enone 12.

4. Synthesis of methylene bis(tetrahydropyran) 4

Compounds 11 and 12 were reacted with each other in dichloromethane in the presence of 10 mol % of Hoveyda-Grubbs second generation catalyst (HG-II) at 35° C. to give hydroxyenone 10 in a high yield as a single stereoisomer (Scheme 4). Subsequently, compound 10 was treated with potassium t-butoxide in tetrahydrofuran at 0° C. to allow smooth proceeding of the intramolecular conjugate addition reaction to give target silyloxyketone 9 in a yield of 95% as a single stereoisomer. Finally, compound 9 was reacted with a boron trifluoride-diethyl ether complex in dichloromethane in the presence of a large excess amount of triethylsilane, and compound 4 was isolated in a yield of 98% as a diastereomer mixture of about 10:1 with respect to the C9-position. Compound 4 was efficiently constructed with a considerably high convergence by appropriately arranging functional groups necessary for ring formation in Compounds 11 and 12 in advance and utilizing a high functional group acceptability and strong carbon-carbon bond forming ability of olefin metathesis. Actually, compound 4 could be readily synthesized in a gram scale.

Scheme 4. Synthesis of methylene bis(tetrahydropyran) 4.

[Formula 13]

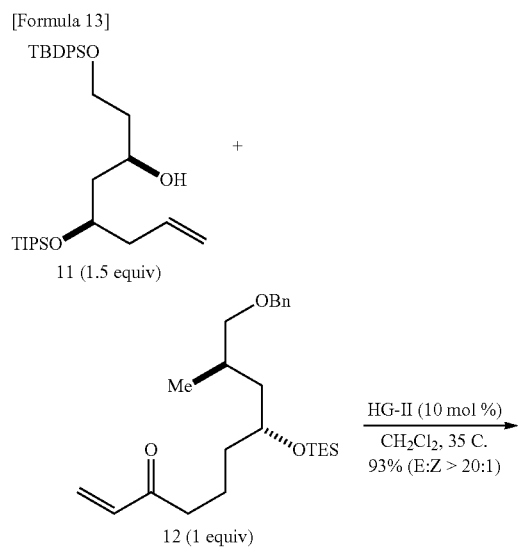

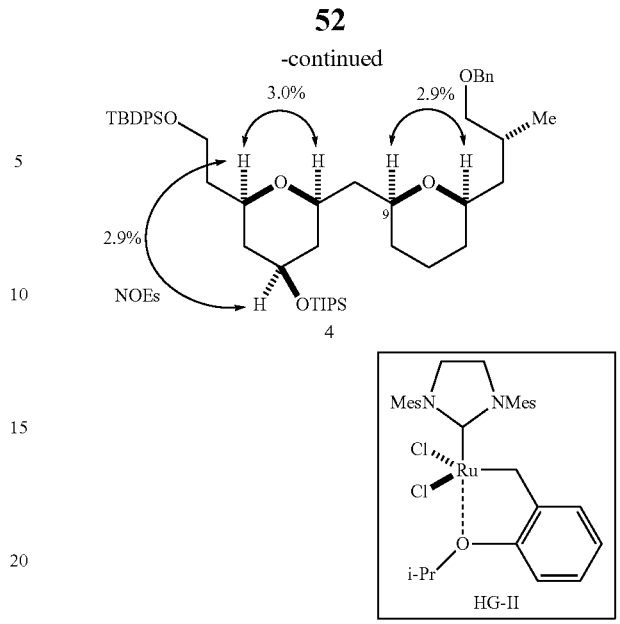

5. Trial of Construction of 20-Membered Ring by RCM

Alcohol generated by hydrogenolysis of Compound 4 was subjected to Dess-Martin oxidation to give aldehyde 19. The aldehyde 19 was converted into olefin 20 by methylenation (Scheme 5). The t-butyl diphenyl silyl group of compound 20 was selectively removed, and the resulting alcohol was oxidized into carboxylic acid 21. Compound 21 and alcohol 6 were condensed to induce triene 5, and its RCM was investigated under various conditions.

RCM was investigated using a G-II catalyst in dichloromethane at reflux or in toluene at 70° C. As a result, only a trace amount of target compound 22 was generated, and the catalyst was decomposed in the initial stage of the reaction. Accordingly, the reaction was performed using an HG-II catalyst in toluene at 80° C. for 1 day. As a result, compound 22 was given in a yield of 30%, and 18% of raw material 5 was recovered. A reaction for a longer time or at a higher temperature, however, did not increase the yield of compound 22, but generated the compound 22' at the same degree as a by-product. This is believed that an active species of RCM, a ruthenium methylidene complex, reacted with iodinated vinyl moieties to generate the by-product. On the other hand, target compound 22 could be prepared in a yield of 52% (raw material recovery: 24%) by performing this reaction in 1,2-dichloroethane at 75° C. with only a trace amount of compound 22' generated. In addition, titanium tetraisopropoxide and 2,6-dichloro-1,4-benzoquinone were investigated as additives, but were not useful in this reaction.

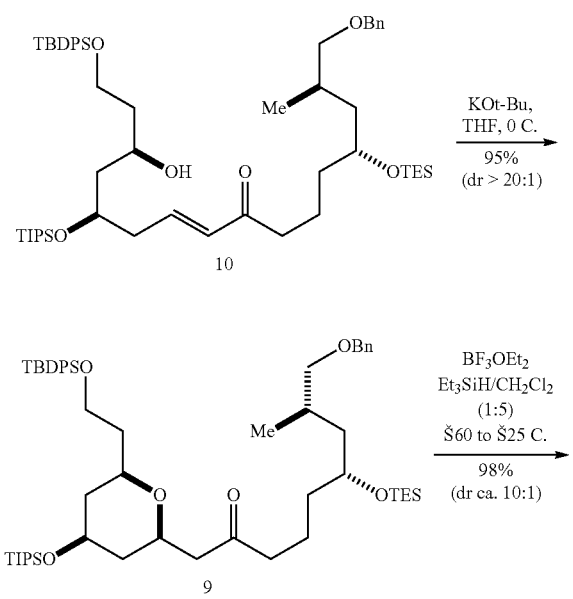

Scheme 5. Synthesis and RCM of triene 5.

[Formula 14]

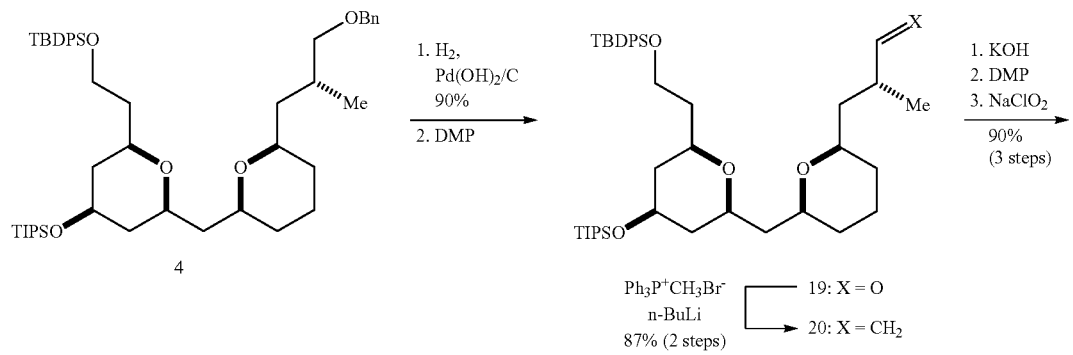

-continued

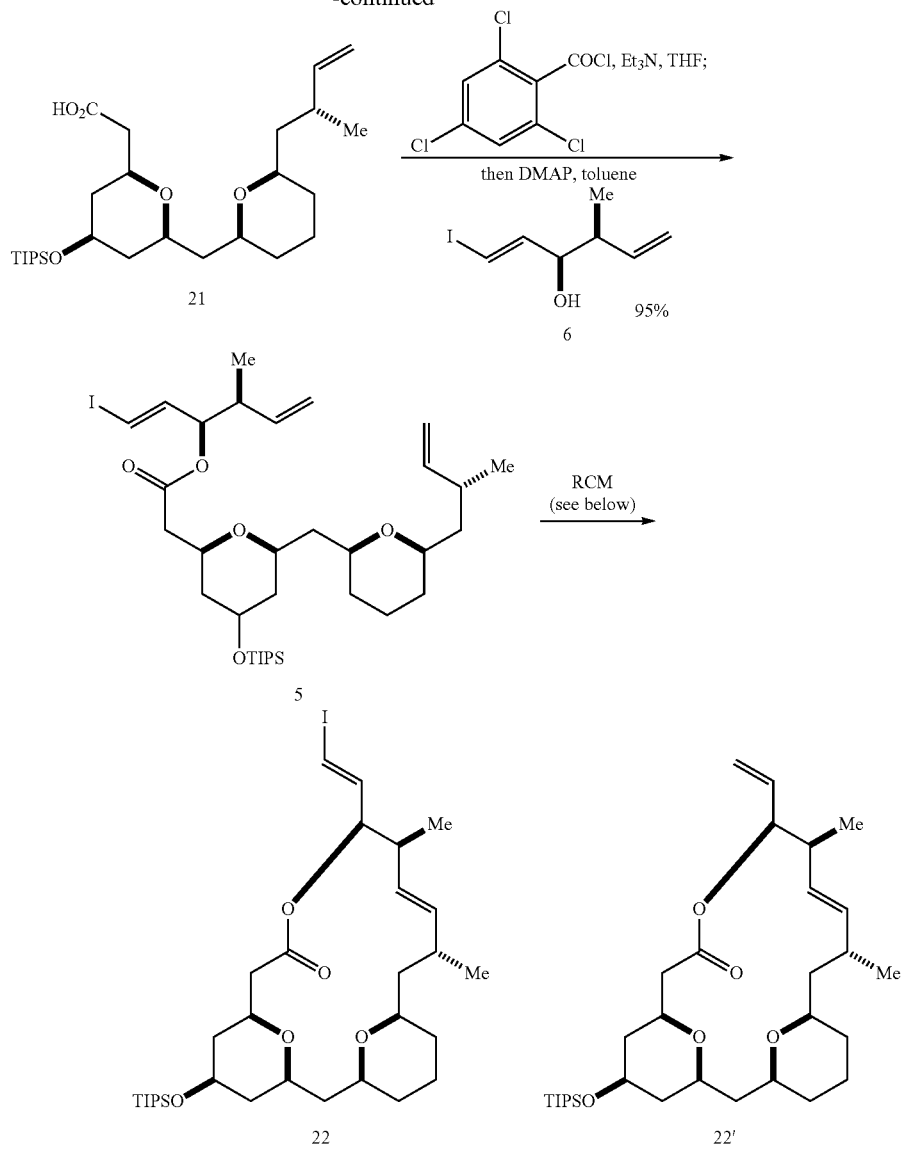

| Reagents and Conditions | 22 | 22' |
|---|---|---|
| G-II (30~60 mol %) CH$_2$Cl$_2$, reflux or toluene, 70° C., 1 d | trace | n.d. |
| HG-II (60 mol %) toluene, 80° C., 1 d | 30% (rsm: 18%) | trace |
| HG-II (60 mol %) ClCH$_2$CH$_2$Cl (5 mM), 75° C., 2 d | 28-52% (rsm: 24-27%) | trace |

6. Completion of Construction and Total Synthesis of 20-Membered Ring Through Macrolactonization Construction of a 20-membered ring by a Yamaguchi method was investigated (Scheme 6). A Julia-Kocienski reaction between aldehyde 19 and separately prepared sulfone 8 was investigated. As a result, target (E)-olefin 23 was isolated in a yield of 63% (raw material recovery: 23%) by treating compound 8 with lithium bis(trimethylsilyl)amide in tetrahydrofuran/hexamethyl phosphoamide (4:1) at −78° C. to generate a corresponding anion, then adding compound 20 thereto, and gradually warming the reaction solution to room temperature. The t-butyl diphenylsilyl group of compound 23 was selectively removed, and the resulting alcohol was converted into ester 24 by two-stage oxidation and methylesterification. It was found that deprotection was most efficiently achieved by treating the p-methoxybenzyl group of compound 24 with a boron trifluoride-diethyl ether complex in the presence of triethylsilane, and alcohol 25 was prepared in a yield of 89%. Compound 25 was hydrolyzed, and the resulting hydroxycarboxylic acid was macrolactonized by a Yamaguchi method. As a result, a 20-membered ring lactone 22 was isolated in a yield of 94% (the sum of two stages). The alcohol prepared by removing the triisopropylsilyl group of compound 22 was oxidized to quantitatively give ketone 26. Compound 26 was subjected to a Horner-Wadsworth-Emmons reaction using chiral phosphonate 27 and sodium bis(trimethylsilyl)amide to give compound 3 as a mixture of E/Z isomers (E/Z=ca. 1:5) in a yield of 94%. These isomers could be separated by silica gel column chromatography. Lastly, stereoselective introduction of a (E,Z,E)-triene side chain was performed. That is, the Suzuki-Miyaura reaction of compound 3 and vinylboric acid ester 2 smoothly proceeded in tetrahydrofuran at room temperature by using tris(dibenzylideneacetone)dipalladium complex/triphenyl arsenic catalyst and silver oxide to successively give compound (−)-1 as a single isomer in a yield of 73%. The various spectral data ($^1$H and $^{13}$C NMR spectra and high-resolution mass spectrometry spectra) of the synthetic product, compound (−)-1, completely agreed with those of the natural product. The specific rotation ($[\alpha]^{24}_D$−121.5 (c=0.22, chloroform)) of the synthetic product also well agreed with that ($[\alpha]^{25}_D$−92.5 (c=0.069, chloroform)) of the natural product.

Scheme 6. Completion of the total synthesis.

[Formula 15]

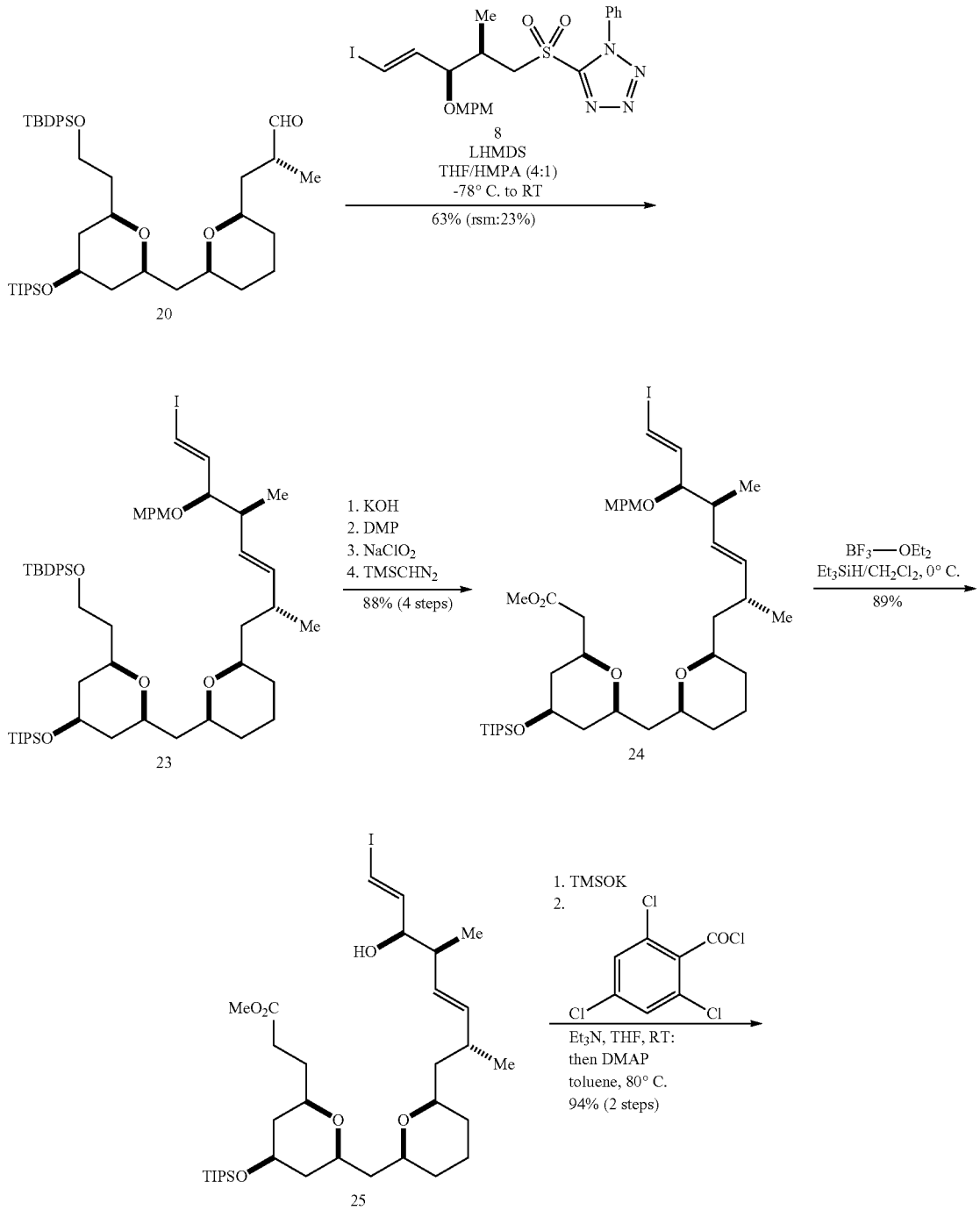

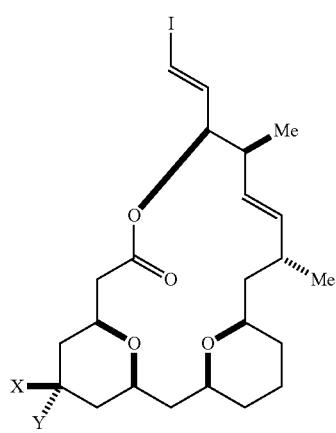
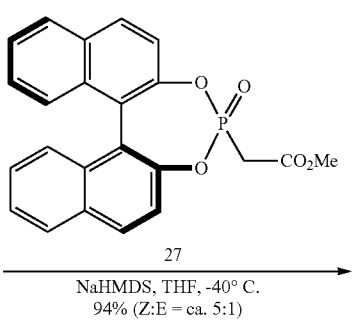
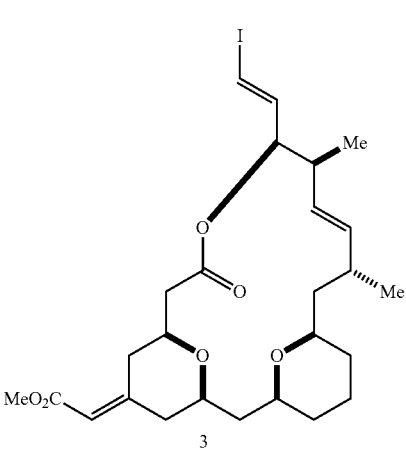
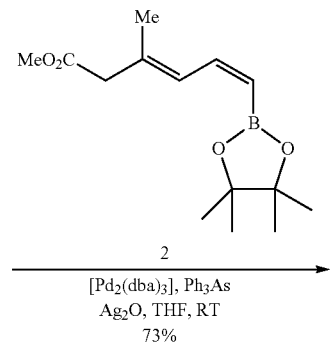
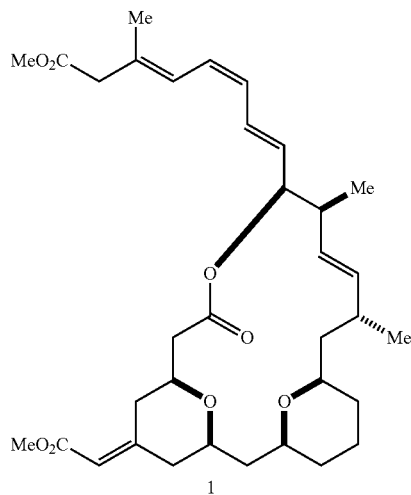

SYNTHESIS EXAMPLES (1) The formulae of analogs 1 and 2 are those representing compounds III and IV, respectively. Compound III was synthesized by a Suzuki-Miyaura reaction of compound I described in a publication (H. Fuwa and M. Sasaki, Organic Letters, 12, 574-577 (2010)) and (Z)-vinylboric acid pinacol ester II described in a publication (H. Fuwa and M. Sasaki, Organic Letters, 12, 574-577 (2010)). Compound IV was prepared by acetylation of compound III with acetic anhydride and pyridine.

[Formula 16]

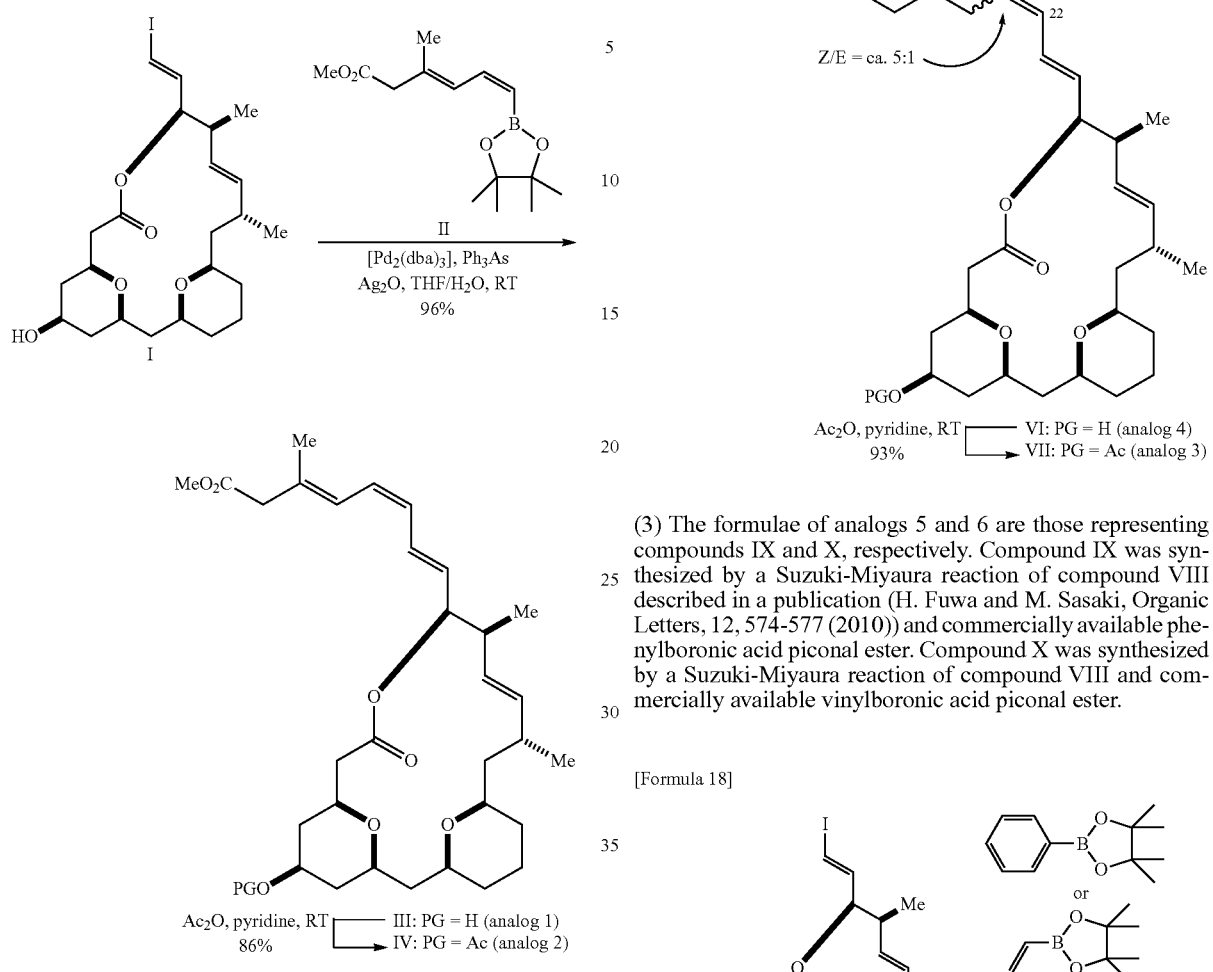

Ac₂O, pyridine, RT  — III: PG = H (analog 1)
86%  → IV: PG = Ac (analog 2)

Ac₂O, pyridine, RT  — VI: PG = H (analog 4)
93%  → VII: PG = Ac (analog 3)

(2) The formulae of analogs 3 and 4 are those representing compounds VII and VI, respectively. Compound VI was synthesized by a Stille reaction of compound I and vinyl tin V described in a publication (T. Hosoya, K. Sumi, H. Doi, M. Wakao, and M. Suzuki, Org. Biomol. Chem., 4, 410-415 (2006)). Compound VII was prepared by acetylation of compound VI with acetic anhydride and pyridine.

[Formula 17]

(3) The formulae of analogs 5 and 6 are those representing compounds IX and X, respectively. Compound IX was synthesized by a Suzuki-Miyaura reaction of compound VIII described in a publication (H. Fuwa and M. Sasaki, Organic Letters, 12, 574-577 (2010)) and commercially available phenylboronic acid piconal ester. Compound X was synthesized by a Suzuki-Miyaura reaction of compound VIII and commercially available vinylboronic acid piconal ester.

[Formula 18]

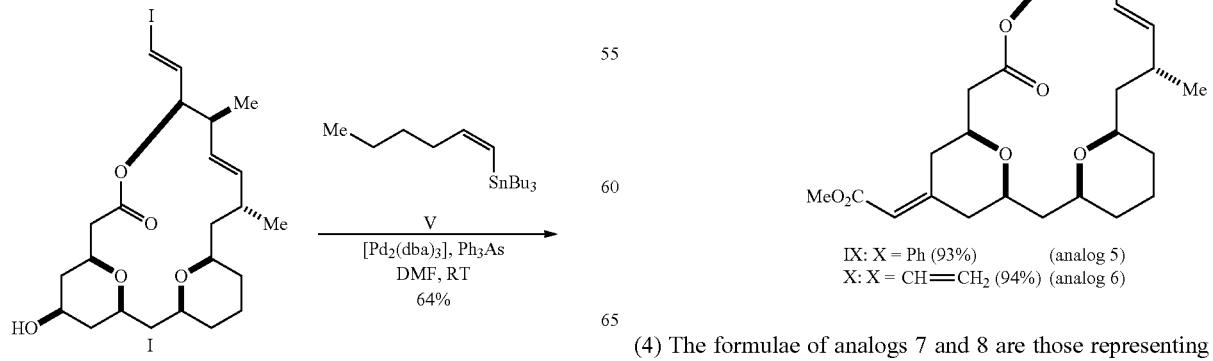

IX: X = Ph (93%)  (analog 5)
X: X = CH=CH₂ (94%)  (analog 6)

(4) The formulae of analogs 7 and 8 are those representing compounds XII and XIV, respectively. Compound XII was synthesized by a Suzuki-Miyaura reaction of compound XI described in a publication (H. Fuwa and M. Sasaki, Organic Letters, 12, 574-577 (2010)) and compound II. Compound XIV was synthesized by a Suzuki-Miyaura reaction of compound XIII and compound II, where compound XIII was prepared by methylenation of compound XI by a Julia-Kocienski reaction (C. Aissa, The Journal of Organic Chemistry, 2006, 71, 360-363).

[Formula 19]

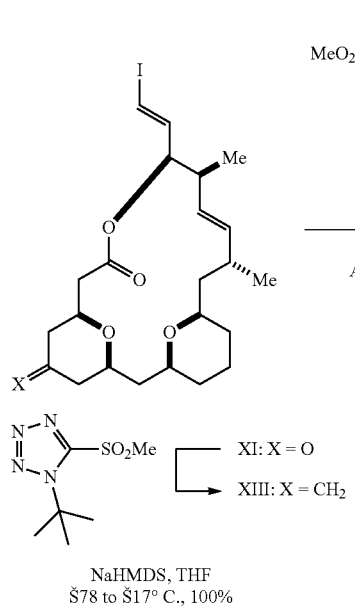

NaHMDS, THF
−78 to −17° C., 100%

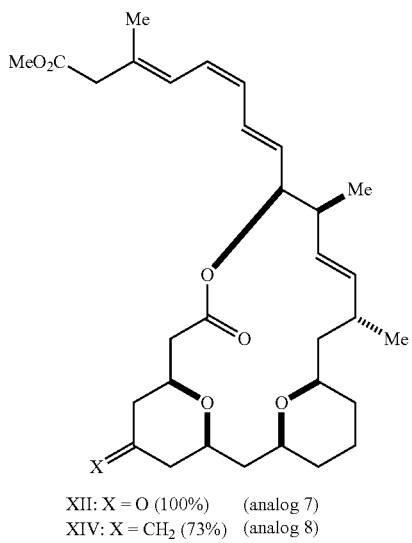

XII: X = O (100%)    (analog 7)
XIV: X = CH$_2$ (73%)    (analog 8)

Example 1

Synthesis of Compound III (Analog 1)

[Formula 20]

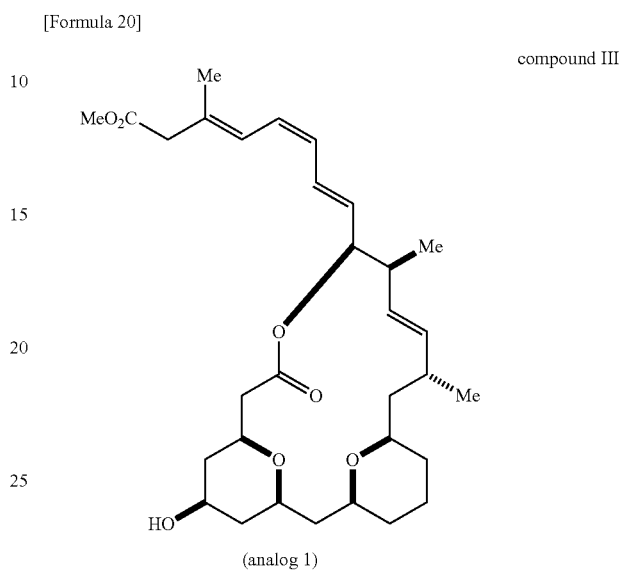

Silver oxide (22.8 mg, 0.0984 mmol), trisdibenzylideneacetone dipalladium (2.7 mg, 0.0029 mmol), and triphenyl arsenic (7.2 mg, 0.024 mmol) were added to 1.1 mL of a mixture solution of alcohol I (10.2 mg, 0.0197 mmol) and (Z)-vinylboric acid pinacol ester II (29.2 mg, 0.110 mmol) in tetrahydrofuran/water (volume ratio: 10:1) at room temperature. The reaction mixture was stirred at room temperature for 20 minutes, and then insolubles were removed by filtration through Celite. The filtrate was concentrated under reduced pressure. The crude product was purified by silica gel column chromatography (Fuji Silysia BW-300 silica gel; eluent: 40 to 60% ethyl acetate/hexane) to give compound III (10.0 mg, yield: 96%) as a light-yellow liquid.

$[\alpha]^{25}_D$=−121.4 (c=0.14, benzene); IR (thin film) 3454, 2928, 1737, 1436, 1372, 1326, 1263, 1183, 1157, 1090, 1039, 975, 903, 680 cm$^{-1}$; $^1$H-NMR (600 MHz, deuterated chloroform): δ=6.66 (dd, J=15.1, 11.3 Hz, 1H), 6.37 (d, J=11.3 Hz, 1H), 6.18 (dd, J=11.3, 11.3 Hz, 1H), 5.96 (dd, J=11.3, 11.3 Hz, 1H), 5.66 (dd, J=15.1, 6.9 Hz, 1H), 5.53 (dd, J=15.1, 9.6 Hz, 1H), 5.23 (m, 1H), 5.06 (dd, J=15.1, 9.6 Hz, 1H), 3.85-3.74 (m, 2H), 3.68 (s, 3H), 3.27 (m, 1H), 3.20 (m, 1H), 3.12 (m, 1H), 3.10 (s, 2H), 2.56 (m, 1H), 2.53 (dd, J=14.1, 11.0 Hz, 1H), 2.43 (dd, J=14.1, 2.8 Hz, 1H), 2.32 (m, 1H), 1.96 (m, 1H), 1.84 (m, 1H), 1.83 (s, 3H), 1.77-1.72 (m, 2H), 1.62 (m, 1H), 1.54-1.01 (m, 13H), 0.92 ppm (d, J=6.5 Hz, 3H); $^{13}$C-NMR (150 MHz, deuterated benzene): δ=170.7, 170.3, 135.8, 133.2, 133.1, 132.2, 128.5, 126.1, 124.3, 78.0, 75.7, 75.3, 72.9, 72.1, 67.7, 50.9, 44.9, 44.4, 43.5, 42.4, 41.3, 41.2, 40.2, 33.1, 32.7, 32.0, 24.3, 21.9, 16.4, 14.5 ppm; HRMS (ESI): m/z Calcd.: 553.3136 [(M+Na)$^+$]. Found: 553.3148.

Example 2

Synthesis of Compound IV (Analog 2)

[Formula 21]

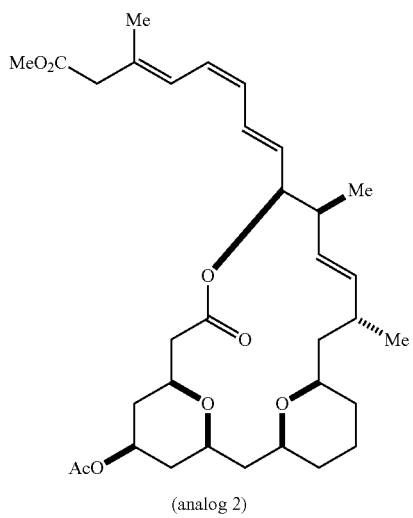

(analog 2)

Acetic anhydride (0.5 mL) was added to 0.5 mL of a solution of compound III (2.6 mg, 0.0049 mmol) in pyridine, and the reaction solution was stirred overnight at room temperature. The reaction solution was concentrated under reduced pressure, followed by purification by silica gel column chromatography (Fuji Silysia BW-300 silica gel; eluent: 10 to 30% ethyl acetate/hexane) to give compound IV (2.4 mg, yield: 86%) as a colorless liquid.

$[\alpha]^{23}_D$=−111.8 (c=0.12, benzene); $^1$H NMR (600 MHz, deuterated benzene): δ=6.95 (dd, J=15.1, 11.3 Hz, 1H), 6.38 (d, J=11.7 Hz, 1H), 6.16 (dd, J=11.7, 11.0 Hz, 1H), 5.98 (dd, J=11.3, 11.0 Hz, 1H), 5.82 (dd, J=14.8, 9.6 Hz, 1H), 5.73 (dd, J=15.1, 6.8 Hz, 1H), 5.65 (m, 1H), 5.12 (dd, J=15.1, 9.6 Hz, 1H), 4.83 (m, 1H), 3.71 (m, 1H), 3.50 (m, 1H), 3.40 (m, 1H), 3.26 (s, 3H), 2.97 (m, 1H), 2.87 (m, 1H), 2.80 (s, 2H), 2.38-2.30 (m, 2H), 2.03 (dd, J=14.4, 2.8 Hz, 1H), 1.95 (dd, J=12.7, 11.3 Hz, 1H), 1.72-1.44 (m, 12H), 1.38 (m, 1H), 1.32-1.01 (m, 9H), 0.99 ppm (d, J=6.9 Hz, 3H); $^{13}$C NMR (150 MHz, deuterated benzene): δ=170.9, 170.2, 169.4, 135.9, 133.2, 133.1, 132.1, 128.5, 126.1, 124.3, 78.3, 75.9, 75.4, 73.0, 72.1, 70.3, 51.2, 45.2, 44.5, 43.8, 42.7, 41.3, 37.6, 36.6, 33.4, 32.9, 32.2, 24.5, 22.1, 20.8, 16.6, 14.7 ppm; HRMS (ESI): m/z Calcd.: 595.3241 [(M+Na)$^+$]. Found: 595.3260.

Example 3

Synthesis of Compound VII (Analog 3)

[Formula 22]

(analog 3)

Acetic anhydride (0.5 mL) was added to 0.5 mL of a solution of compound VI (5.6 mg, 0.012 mmol) in pyridine, and the reaction solution was stirred overnight at room temperature. The reaction solution was concentrated under reduced pressure. The crude product was purified by silica gel column chromatography (Fuji Silysia BW-300 silica gel; eluent: 10 to 20% ethyl acetate/hexane) to give compound VII (5.7 mg, yield: 93%) as a mixture of unseparated geometric isomers with a ratio of 5:1 (the ratio of isomers was estimated based on the $^1$H-NMR spectrum; and the double bond at the C22-position of the main product exhibited Z geometric isomerism).

$[\alpha]^{23}_D$=−49.3 (c=0.57, chloroform); IR (thin film): 2927, 2862, 1740, 1453, 1373, 1325, 1239, 1188, 1160, 1090, 1031, 975, 905, 677 cm$^{-1}$; $^1$H-NMR (600 MHz, deuterated chloroform, signal of the major product): δ=6.49 (dd, J=15.1, 11.0 Hz, 1H), 5.94 (dd, J=11.3, 11.0 Hz, 1H), 5.58 (dd, J=15.1, 6.8 Hz, 1H), 5.52 (dd, J=15.1, 9.3 Hz, 1H), 5.45 (m, 1H), 5.21 (m, 1H), 5.06 (m, 1H), 4.90 (m, 1H), 3.85 (dddd, J=11.3, 11.3, 2.4, 2.4 Hz, 1H), 3.26 (m, 1H), 3.20-3.13 (m, 2H), 2.53 (m, 1H), 2.50 (dd, J=14.0, 10.6 Hz, 1H), 2.40 (dd, J=14.0, 3.1 Hz, 1H), 2.34 (m, 1H), 2.18-2.13 (m, 2H), 2.06 (m, 1H), 2.01 (s, 3H), 1.98 (m, 1H), 1.89 (m, 1H), 1.77-1.70 (m, 2H), 1.62 (m, 1H), 1.54-1.00 (m, 15H), 0.92 (d, J=6.9 Hz, 3H), 0.89 ppm (t, J=7.2 Hz, 3H); $^{13}$C-NMR (150 MHz, deuterated chloroform, signal of the major product): δ=170.8, 170.5, 135.3, 133.5, 132.6, 129.7, 128.0, 127.6, 78.7, 76.0, 75.2, 72.7, 72.0, 70.2, 44.1, 43.1, 42.0, 41.4, 37.2, 36.3, 33.0, 32.4, 31.7, 31.6, 27.5, 23.9, 22.3, 21.8, 21.2, 14.3, 13.9 ppm; HRMS (ESI): m/z Calcd.: 539.3343 [(M+Na)$^+$]. Found: 539.3340.

Example 4

Synthesis of compound VI (Analog 4)

[Formula 23]

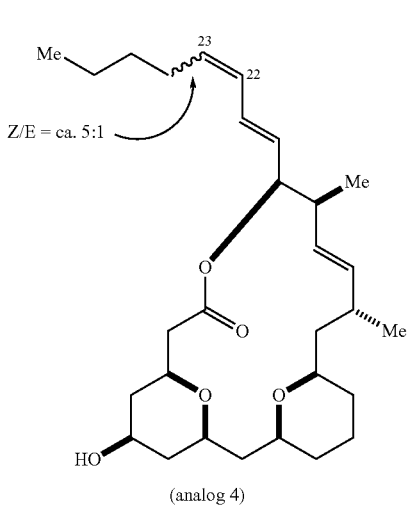

(analog 4)

Trisdibenzylideneacetone dipalladium (2.5 mg, 0.0027 mmol) and triphenyl arsenic (6.8 mg, 0.022 mmol) were added to 1 mL of a solution of alcohol I (9.6 mg, 0.019 mmol) and (Z)-vinyl tin V (34.6 mg, 0.0925 mmol) in N,N-dimethylformamide at room temperature. The reaction solution was stirred at room temperature for 6.5 hours, and the reaction was terminated with a saturated aqueous sodium bicarbonate solution while cooling with ice. The reaction mixture was extracted with ethyl acetate, and the organic layer was washed with a saturated saline solution. The organic layer was dried over anhydrous sodium sulfate, the desiccant was removed by filtration, and the filtrate was concentrated under reduced pressure. The crude product was purified by silica gel column chromatography (Fuji Silysia BW-300 silica gel; eluent: 30 to 45% ethyl acetate/hexane) to give compound VI (5.6 mg, yield: 64%) as a mixture of unseparated geometric isomers with a ratio of 5:1 (the ratio of isomers was estimated based on the $^1$H-NMR spectrum; and the double bond at the C22-position of the main product exhibited Z geometric isomerism).

$[\alpha]^{24}_D$=−43.4 (c=0.50, chloroform); IR (thin film): 3443, 2927, 2862, 1738, 1461, 1372, 1322, 1183, 1122, 1090, 1040, 975, 900, 678 cm$^{-1}$; $^1$H-NMR (600 MHz, deuterated chloroform, signal of the major product): δ=6.49 (dd, J=15.4, 11.3 Hz, 1H), 5.95 (dd, J=11.3, 11.0 Hz, 1H), 5.58 (dd, J=15.1, 6.8 Hz, 1H), 5.52 (dd, J=15.1, 9.7 Hz, 1H), 5.45 (m, 1H), 5.21 (m, 1H), 5.06 (m, 1H), 3.84 (m, 1H), 3.79 (dddd, J=11.3, 11.0, 2.5, 2.0 Hz, 1H), 3.27 (m, 1H), 3.19 (m, 1H), 3.11 (m, 1H), 2.54 (m, 1H), 2.52 (dd, J=14.4, 11.0 Hz, 1H), 2.41 (dd, J=14.4, 2.8 Hz, 1H), 2.34 (m, 1H), 2.18-2.14 (m, 2H), 1.96 (m, 1H), 1.84 (m, 1H), 1.77-1.71 (m, 2H), 1.62 (m, 1H), 1.54-1.00 (m, 17H), 0.92 (d, J=6.9 Hz, 3H), 0.89 ppm (t, J=7.2 Hz, 3H); $^{13}$C-NMR (150 MHz, deuterated chloroform, signal of the major product): δ=171.0, 135.3, 133.4, 132.6, 129.8, 127.8, 127.6, 78.6, 76.0, 75.3, 72.8, 72.2, 68.1, 44.2, 43.1, 42.0, 41.4, 41.1, 40.2, 33.0, 32.4, 31.7, 31.6, 27.5, 23.9, 22.3, 21.8, 14.3, 13.9 ppm; HRMS (ESI): m/z Calcd.: 497.3237 [(M+Na)$^+$]. Found: 497.3233.

Example 5

Synthesis of Compound IX (Analog 5)

[Formula 24]

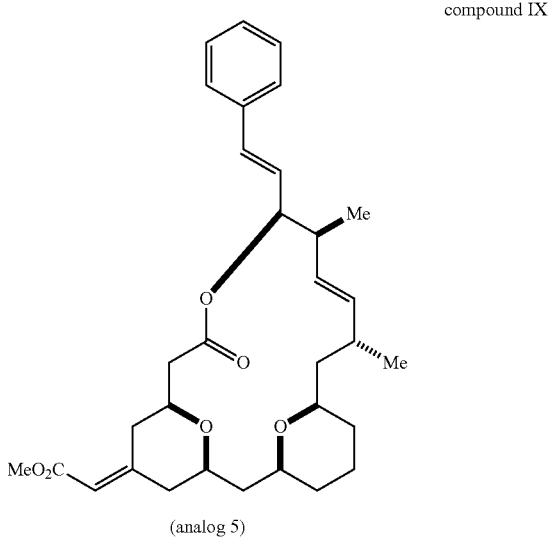

(analog 5)

Silver oxide (7.1 mg, 0.031 mmol), trisdibenzylideneacetone dipalladium (0.8 mg, 0.0009 mmol), and triphenyl arsenic (2.2 mg, 0.0072 mmol) were added to 0.55 mL of a mixture solution of vinyl iodide VIII (3.5 mg, 0.0061 mmol) and phenylboronic acid piconal ester (10.0 mg, 0.0376 mmol) in tetrahydrofuran/water (volume ratio: 10:1) at room temperature. The reaction mixture was stirred at room temperature for 30 minutes. Insolubles were removed by filtration through Celite, and the filtrate was concentrated under reduced pressure. The crude purified product was purified by silica gel column chromatography (Fuji Silysia BW-300 silica gel; eluent: 7.5% ethyl acetate/hexane) to give compound IX (3.0 mg, 93%) as a colorless liquid.

$[\alpha]^{23}_D$=−61.7 (c=0.30, chloroform); IR (thin film): 2928, 1718, 1651, 1435, 1373, 1236, 1154, 1090, 969, 748, 678 cm$^{-1}$; $^1$H-NMR (600 MHz, deuterated chloroform): δ=7.36 (d, J=7.6 Hz, 2H), 7.29 (dd, J=7.9, 7.6 Hz, 2H), 7.22 (dd, J=7.9, 7.9 Hz, 1H), 6.56 (d, J=15.8 Hz, 1H), 6.16 (dd, J=15.8, 6.5 Hz, 1H), 5.68 (s, 1H), 5.56 (dd, J=15.1, 9.2 Hz, 1H), 5.35 (m, 1H), 5.10 (dd, J=15.1, 9.6 Hz, 1H), 3.87 (app. d, J=13.4 Hz, 1H), 3.81 (m, 1H), 3.67 (s, 3H), 3.31 (m, 1H), 3.23-3.16 (m, 2H), 2.61-2.49 (m, 3H), 2.43 (m, 1H), 2.22 (dd, J=12.4, 12.4 Hz, 1H), 2.12 (app. d, J=13.4 Hz, 1H), 1.97 (dd, J=12.7, 12.4 Hz, 1H), 1.80-1.73 (m, 2H), 1.63-1.47 (m, 2H), 1.45 (ddd, J=14.1, 11.3, 2.8 Hz, 1H), 1.40 (m, 1H), 1.25-1.04 (m, 7H), 0.93 ppm (d, J=6.5 Hz, 3H); $^{13}$C-NMR (150 MHz, deuterated chloroform): δ=170.7, 166.8, 156.7, 136.5, 135.5, 132.5, 132.0, 128.5 (2C), 127.7, 126.7, 126.5 (2C), 115.0, 78.7, 76.0, 75.4, 74.9, 74.1, 51.0, 44.1, 43.1, 42.5, 42.1, 41.6, 34.8, 33.1, 32.5, 31.6, 23.9, 21.8, 14.4 ppm; HRMS (ESI): m/z Calcd.: 545.2874 [(M+Na)$^+$].

Found: 545.2881.

Example 6

Synthesis of Compound X (Analog 6)

[Formula 25]

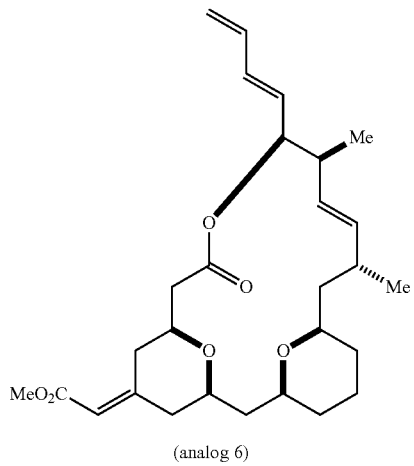

(analog 6)

Silver oxide (8.3 mg, 0.036 mmol), trisdibenzylideneacetone dipalladium (1.0 mg, 0.0011 mmol), and triphenyl arsenic (2.6 mg, 0.0085 mmol) were added to 1.1 mL of a mixture solvent of vinyl iodide VIII (4.1 mg, 0.0072 mmol) and vinylboronic acid piconal ester (5.0 mg, 0.032 mmol) in tetrahydrofuran/water (volume ratio: 10:1) at room temperature. The reaction mixture was stirred at room temperature for 1 hour. Insolubles were removed by filtration through Celite, and the filtrate was concentrated under reduced pressure. The crude purified product was purified by silica gel column chromatography (Fuji Silysia BW-300 silica gel; eluent: 7 to 10% ethyl acetate/hexane) to give compound X (3.2 mg, 94%) as a colorless liquid.

$[\alpha]^{23}_D$=−75.9 (c=0.32, chloroform); IR (thin film): 2929, 1738, 1652, 1435, 1373, 1236, 1090, 1045, 1008, 975, 903, 858, 679 cm$^{-1}$; $^1$H-NMR (600 MHz, deuterated chloroform): δ=6.33 (ddd, J=16.8, 10.4, 10.3 Hz, 1H), 6.19 (dd, J=15.1, 10.3 Hz, 1H), 5.68 (s, 1H), 5.64 (dd, J=15.1, 6.2 Hz, 1H), 5.52 (dd, J=15.1, 9.6 Hz, 1H), 5.23-5.17 (m, 2H), 5.10 (app. d, J=10.0 Hz, 1H), 5.06 (dd, J=15.1, 9.6 Hz, 1H), 3.86 (app. d, J=13.4 Hz, 1H), 3.79 (m, 1H), 3.67 (s, 3H), 3.29 (m, 1H), 3.20-3.14 (m, 2H), 2.56-2.46 (m, 3H), 2.32 (dddd, J=16.1, 7.3, 6.9, 2.1 Hz, 1H), 2.20 (dd, J=12.7, 12.0 Hz, 1H), 2.11 (app. d, J=13.4 Hz, 1H), 1.95 (dd, J=12.7, 12.7 Hz, 1H), 1.78-1.71 (m, 2H), 1.61-1.47 (m, 2H), 1.43 (ddd, J=14.1, 11.3, 2.8 Hz, 1H), 1.38 (m, 1H), 1.25-1.03 (m, 4H), 1.03 (d, J=6.8 Hz, 3H), 0.92 ppm (d, J=6.9 Hz, 3H); $^{13}$C-NMR (150 MHz, deuterated chloroform): δ=170.7, 166.8, 156.7, 135.4, 132.6, 132.5, 130.8, 117.9, 115.0, 78.2, 76.0, 75.3, 74.9, 74.1, 51.0, 44.0, 43.1, 42.5, 41.9, 41.5, 34.8, 33.0, 32.4, 31.6, 23.9, 21.8, 14.3 ppm; HRMS (ESI): m/z Calcd.: 495.2717[(M+Na)$^+$]. Found: 495.2698.

Example 7

Synthesis of Compound XII (Analog 7)

[Formula 26]

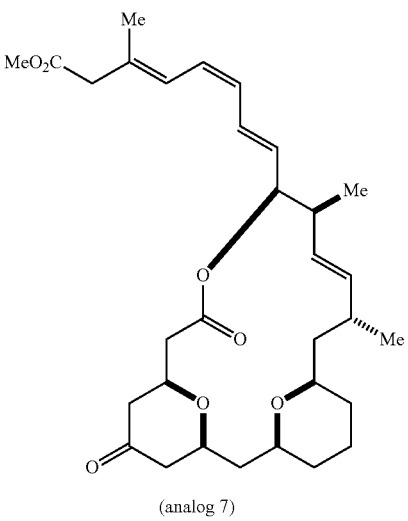

(analog 7)

Silver oxide (16.0 mg, 0.0690 mmol), trisdibenzylideneacetone dipalladium (1.9 mg, 0.0021 mmol), and triphenyl arsenic (5.1 mg, 0.017 mmol) were added to 1.1 mL of a mixture solution of ketone XI (7.1 mg, 0.014 mmol) and (Z)-vinylboric acid pinacol ester II (15.2 mg, 0.0571 mmol) in tetrahydrofuran/water (volume ratio: 10:1) at room temperature. The reaction mixture was stirred at room temperature for 20 minutes. Insolubles were removed by filtration through Celite, and the filtrate was concentrated under reduced pressure. The crude product was purified by silica gel column chromatography (Fuji Silysia BW-300 silica gel; eluent: 20 to 30% ethyl acetate/hexane) to give compound XII (7.4 mg, yield: 100%) as a colorless liquid.

$[\alpha]^{23}_D$=−84.2 (c=0.74, benzene); IR (thin film): 2928, 1737, 1433, 1370, 1329, 1257, 1214, 1156, 1091, 973, 949, 680 cm$^{-1}$; $^1$H-NMR (600 MHz, deuterated benzene): δ=6.93 (dd, J=14.8, 11.7 Hz, 1H), 6.37 (d, J=11.7 Hz, 1H), 6.17 (dd, J=11.3, 11.3 Hz, 1H), 5.98 (dd, J=11.0, 11.0 Hz, 1H), 5.77-5.65 (m, 3H), 5.13 (dd, J=15.1, 9.6 Hz, 1H), 3.78 (m, 1H), 3.47 (m, 1H), 3.39 (m, 1H), 3.27 (s, 3H), 3.06 (m, 1H), 2.83 (m, 1H), 2.80 (s, 2H), 2.36 (dddd, J=16.1, 7.2, 7.2, 1.7 Hz, 1H), 2.22 (dd, J=14.4, 10.7 Hz, 1H), 1.99-1.81 (m, 5H), 1.78 (dd, J=14.4, 12.0 Hz, 1H), 1.69 (s, 3H), 1.65 (m, 1H), 1.56 (m, 1H), 1.49 (m, 1H), 1.41 (m, 1H), 1.28-1.20 (m, 3H), 1.18 (d, J=6.9 Hz, 3H), 1.07-1.00 (m, 2H), 0.99 (d, J=6.8 Hz, 3H); $^{13}$C-NMR (150 MHz, deuterated benzene): δ=204.0, 170.9, 169.7, 136.0, 133.3, 133.0, 131.8, 128.5, 127.9, 126.3, 124.2, 78.3, 75.9, 75.2, 74.5, 73.2, 51.2, 47.7, 46.4, 45.2, 44.4, 43.8, 42.6, 41.3, 33.5, 32.8, 32.1, 24.9, 24.4, 22.1, 16.7, 14.6 ppm; HRMS (ESI): m/z Calcd.: 551.2979 [(M+Na)$^+$]. Found: 551.2974.

Example 8

Synthesis of Compound XIV (Analog 8)

[Formula 27]

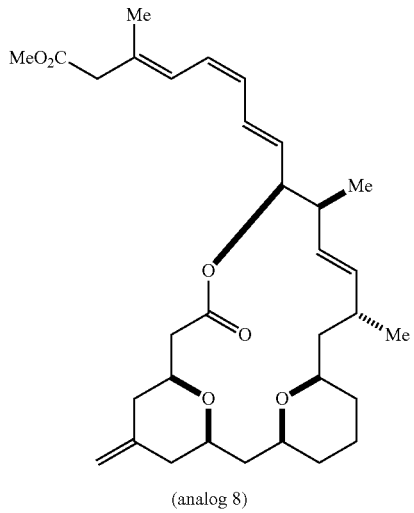

compound XIV (analog 8)

Silver oxide (9.0 mg, 0.039 mmol), trisdibenzylideneacetone dipalladium (1.1 mg, 0.0012 mmol), and triphenyl arsenic (2.9 mg, 0.0095 mmol) were added to 1.1 mL of a mixture solvent of olefin XIII (4.0 mg, 0.0078 mmol) and (Z)-vinylboric acid pinacol ester II (9.6 mg, 0.036 mmol) in tetrahydrofuran/water (volume ratio: 10:1) at room temperature. The reaction mixture was stirred at room temperature for 20 minutes. Insolubles were removed by filtration through Celite, and the filtrate was concentrated under reduced pressure. The crude purified product was purified by silica gel column chromatography (Fuji Silysia BW-300 silica gel; eluent: 7% ethyl acetate/hexane) and then by thin-layer chromatography (E. Merck silica gel 60 F$_{254}$ plates (0.25-mm thickness), 25 mm×25 mm, eluted with 8% ethyl acetate/hexane twice and then with 12% ethyl acetate/hexane) to give compound XIV (3.0 mg, yield: 73%) as a colorless liquid.

$[\alpha]^{24}_D$=−69.2 (c=0.23, chloroform); IR (thin film): 2930, 1739, 1434, 1368, 1328, 1255, 1214, 1156, 1092, 1045, 976 cm$^{-1}$; $^1$H-NMR (600 MHz, deuterated benzene): δ=6.95 (dd, J=15.1, 11.3 Hz, 1H), 6.38 (d, J=9.6 Hz, 1H), 6.16 (dd, J=11.3, 11.3 Hz, 1H), 5.98 (dd, J=11.3, 11.3 Hz, 1H), 5.86 (dd, J=15.1, 9.6 Hz, 1H), 5.75 (dd, J=14.8, 6.8 Hz, 1H), 5.69 (m, 1H), 5.13 (dd, J=14.8, 9.6 Hz, 1H), 4.66 (s, 1H), 4.65 (s, 1H), 3.77 (dddd, J=11.0, 10.6, 3.1, 2.8 Hz, 1H), 3.56 (m, 1H), 3.43 (m, 1H), 3.26 (s, 3H), 3.08 (m, 1H), 2.90 (m, 1H), 2.80 (s, 2H), 2.40-2.34 (m, 2H), 2.13 (dd, J=14.8, 2.8 Hz, 1H), 2.01 (m, 1H), 1.89-1.71 (m, 4H), 1.69 (s, 3H), 1.65 (m, 1H), 1.59-1.42 (m, 4H), 1.32-1.21 (m, 2H), 1.20 (d, J=6.9 Hz, 3H), 1.14 (m, 1H), 1.06 (m, 1H), 0.99 ppm (d, J=6.5 Hz, 3H); $^{13}$C-NMR (150 MHz, deuterated benzene): δ=170.9, 170.4, 144.5, 135.9, 133.2, 133.1, 132.2, 128.5, 126.1, 124.3, 109.3, 78.2, 76.0, 75.9, 75.5, 75.0, 51.2, 45.2, 44.8, 43.8, 42.7, 41.6, 40.9, 39.9, 33.4, 32.9, 32.2, 24.5, 22.1, 16.6, 14.7 ppm; HRMS (ESI): m/z Calcd.: 549.3187 [(M+Na)$^+$]. Found: 549.3187.

Example 9

Synthesis of Compound XIII

[Formula 28]

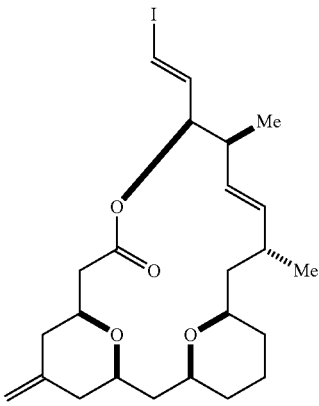

compound XIII

A solution (1 mL) of ketone XI (7.3 mg, 0.014 mmol) and 1-tert-butyl-5-methanesulfonyl-1H-tetrazole (28.6 mg, 0.140 mmol) in tetrahydrofuran was cooled to −78° C., and to this solution was slowly dropwise added sodium bis(trimethylsilyl)amide (1.0 M tetrahydrofuran solution, 0.140 mL, 0.14 mmol). The reaction solution was slowly warmed to −17° C. over 85 minutes, and then a saturated aqueous ammonium chloride solution was added thereto to terminate the reaction. The reaction mixture was extracted with ethyl acetate, and the organic layer was washed with a saturated saline solution. The organic layer was dried over anhydrous sodium sulfate, the desiccant was removed by filtration, and the filtrate was concentrated under reduced pressure. The crude product was purified by silica gel column chromatography (Fuji Silysia BW-300 silica gel; eluent: 5% ethyl acetate/hexane) to give compound XIII (7.3 mg, yield: 100%) as a colorless liquid.

$[\alpha]^{25}_D$=−22.4 (c=0.36, chloroform); IR (thin film): 2929, 1740, 1431, 1368, 1326, 1254, 1214, 1179, 1154, 1091, 1045, 975, 946, 894, 680 cm$^{-1}$; $^1$H-NMR (600 MHz, deuterated chloroform): δ=6.49 (dd, J=14.5, 6.2 Hz, 1H), 6.33 (dd, J=14.5, 1.1 Hz, 1H), 5.48 (dd, J=15.1, 9.6 Hz, 1H), 5.12 (m, 1H), 5.07 (dd, J=15.1, 9.6 Hz, 1H), 4.729 (s, 1H), 4.726 (s, 1H), 3.74 (m, 1H), 3.23 (m, 1H), 3.15 (m, 1H), 3.07 (m, 1H), 2.53 (m, 1H), 2.51 (dd, J=14.1, 10.3 Hz, 1H), 2.46 (dd, J=14.1, 3.4 Hz, 1H), 2.31 (dddd, J=16.2, 7.2, 6.9, 1.7 Hz, 1H), 2.22 (app. d, J=12.7 Hz, 1H), 2.11 (app. d, J=13.1 Hz, 1H), 2.04 (app. d, J=12.7 Hz, 1H), 1.99 (app. d, J=13.1 Hz, 1H), 1.77-1.70 (m, 2H), 1.62 (m, 1H), 1.50-1.40 (m, 3H), 1.37 (m, 1H), 1.25-1.01 (m, 6H), 0.91 ppm (d, J=6.8 Hz, 3H); $^{13}$C-NMR (150 MHz, deuterated chloroform): δ=170.8, 143.8, 142.9, 136.0, 131.7, 109.5, 79.5, 79.3, 76.0, 75.7, 75.2, 74.7, 44.2, 43.0, 41.4, 41.1, 40.6, 39.8, 32.9, 32.4, 31.6, 23.9, 21.7, 14.3 ppm; HRMS (ESI): m/z Calcd.: 537.1472 [(M+Na)$^+$]. Found: 538.1499.

Test Example 1

Drug Sensitivity Test for Exiguolide Using a Panel of Human Cultured Cancer Cell Lines Method The anticancer activity of exiguolide was examined by an in vitro drug sensitivity test using a panel of 39 human cultured cancer cell lines, by Professor Yamori, Molecular Pharmacology, Cancer Chemotherapy Center of Japanese Foundation for Cancer Research upon request.

The test was performed by seeding seven lung cancer cell lines, six gastric cancer cell lines, five colon cancer cell lines, five ovarian cancer cell lines, six brain cancer cell lines, five breast cancer cell lines, two kidney cancer cell lines, two prostatic cancer cell lines, and one melanoma cell line, 39 cell lines in total, in a 96-well plate, adding a sample solution containing a predetermined concentration of exiguolide to each well on the following day, culturing the cell lines for two days, and measuring the cell growth by colorimetry with sulforhodamine B. The measurement results were input into a computer, and the sensitivity patterns (growth rate and finger print, described below) of each cell line on exiguolide were analyzed using three parameters, $GI_{50}$, TGI, and $LC_{50}$, as indices. The data were also subjected to analysis comparing with sensitivities on known compounds showing cell growth-inhibiting activities.

The growth rate percentages were plotted with respect to drug concentrations (logarithm) for each cell line, and the growth rates (%) were summarized on each organ cancer (FIG. 3: dose-response curves). In each curve, the concentrations at the points at which the growth rates 50%, 0%, and -50% intersect horizontal lines correspond to log $GI_{50}$, log TGI, and log $LC_{50}$, respectively.

Figure 4:
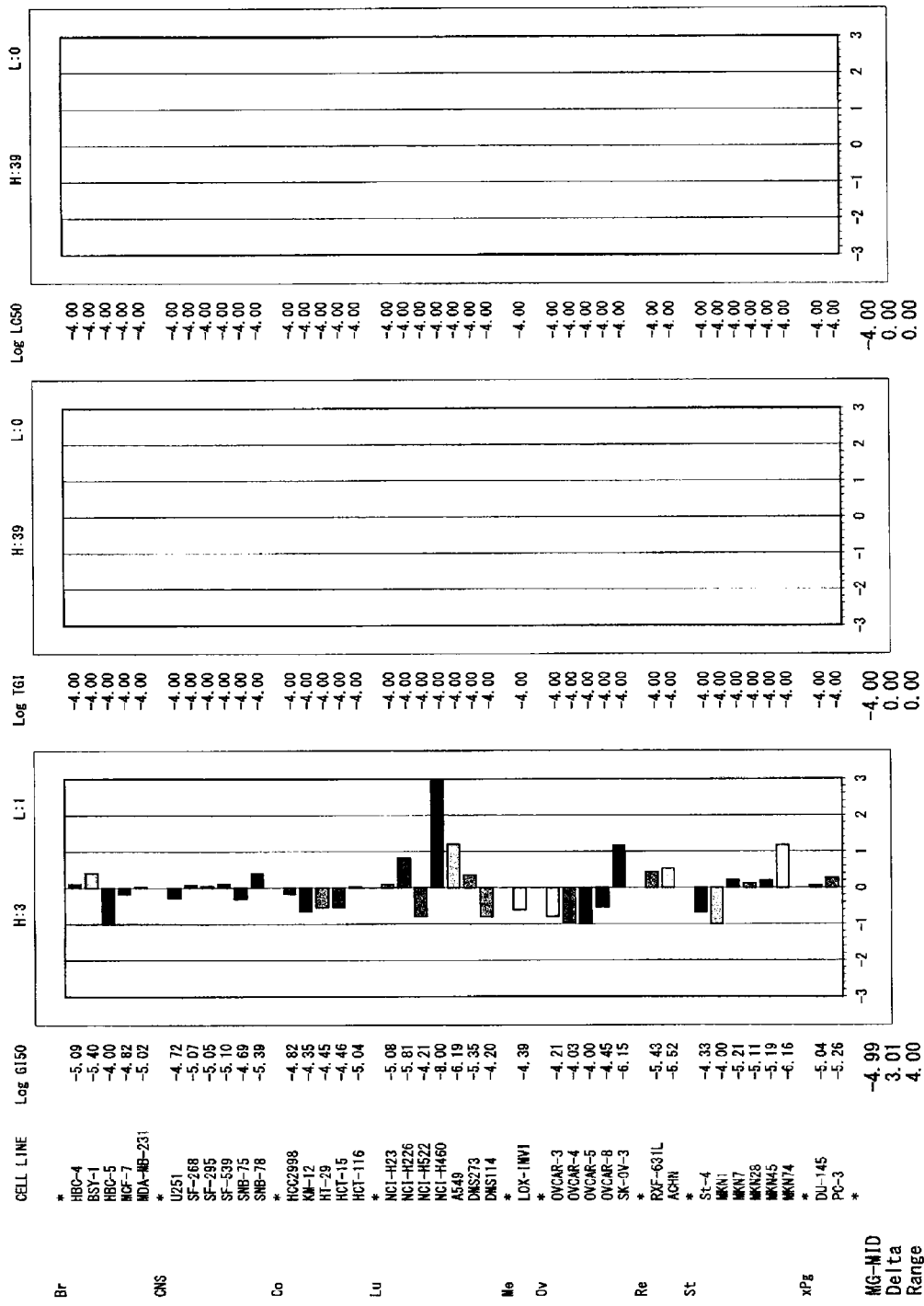
FIG. 4 shows the results (finger print) of a drug sensitivity test of (−)exiguolide using a panel of human cultured cancer cell lines.

The average of log $GI_{50}$ values of all cell lines tested was determined. The difference between this average and log $GI_{50}$ value of each cell line (e.g., how much the $GI_{50}$ of each cell line is high or low relative to the average is shown as logarithmic value) was determined, and the results were drawn as a bar graph extending left or right from the center showing the average log $GI_{50}$ value (scale: 0) to form finger prints (FIG. 4). A cell line having higher sensitivity is drawn as a longer bar extending to the right side.

Results

The results are shown in FIGS. 2 to 4. Tables 1 and 2 show extracts from the results. As shown in Table 1, remarkable sensitivities to exiguolide were recognized in human lung cancer cell lines NCI-H460 (human lung large cell carcinoma) and A549 (human lung adenocarcinoma), a human ovarian cancer cell line SK-OV-3 (human ovarian carcinoma), and a human gastric cancer cell line MKN-74 (human gastric carcinoma).

TABLE 1

| Cell line | Log $GI_{50}$[b] | $GI_{50}$[b] [µM] | $LC_{50}$[c] [µM] |
|---|---|---|---|
| NCI-H460 | −8.00 | 0.01 | >100 |
| A549 | −6.19 | 0.65 | >100 |
| SK-OV-3 | −6.15 | 0.70 | >100 |
| MKN74 | −6.16 | 0.69 | >100 |

[b]$GI_{50}$ = 50% Concentration inducing 50% growth inhibition
[c]$LC_{50}$ = 50% Concentration inducing 50% cell death Exiguolide inhibited the growth of NCI-H460, A549, and SK-OV-3 cell lines at a $GI_{50}$ value of less than a micromole. The antiproliferative activities of bryostatin 1, which has a similar structure, against NCI-H460, A549, and SK-OV-3 cell lines are known to be −5.6, −5.4, and −5.3, respectively (National Cancer Institute database: http://dtp.nci.nih.gov/branches/btb/ivclsp.html), and it was confirmed that exiguolide shows a human cancer cell growth-inhibiting activity 10 to 1000 times higher than that of bryostatin 1.

Exiguolide showed slight correlations with three drugs: pirarubicin, mitomycin C, and SM-5887, shown in Table 2, but no correlation was recognized with other 100 or more drugs. This suggests a possibility that exiguolide inhibits growth of cells through a mechanism of action different from those of known anticancer drugs.

TABLE 2

Correlation with known drugs

| Rank | Compound | r[a] | Molecular targets/Drug type |
|---|---|---|---|
| 1 | Pirarubicin | 0.561 | DNA intercalater |
| 2 | Mitomycin C | 0.556 | DNA alkylating drugs |
| 3 | SM-5887 | 0.537 | DNA topoisomerase II inhibitors |

[a]r = Correlation coefficient

Test Example 2

Antiproliferative Activity Test of Novel Macrolide Compound

Method

Antiproliferative activities of exiguolide and its analogs shown in Examples were examined using A549 and H460 cell lines derived from lung cancer and an A172 cell line derived from human glioblastoma cells. Each cell line was maintained in an RPMI 1640 medium supplemented with 10% fetal bovine serum (in the cases of the H460 cell line and the A172 cell line) or in a DMEM medium supplemented with 10% fetal bovine serum (in the case of the A549 cell line). Cells in the proliferative phase were seeded in a 96-well plate in triplicate and were cultured for 72 hours in the presence of the compound at various concentrations. At the completion of the culture period, an Alamar Blue solution (Invitrogen Corporation) was added to each culture in an amount of 1/10 of that of the medium, followed by leaving to stand for 3 hours. The fluorescence intensity was measured with Fluoroskan Ascent (Thermo Fisher Scientific K.K.). Human umbilical vein endothelial cells (HUVECs) were used as a normal cell control group. The fluorescence intensities of experimental groups were determined as relative intensities to that of the control group and were plotted. The concentration of a compound for achieving the 50% growth inhibition ($IC_{50}$) of each cancer cell line was calculated by a non-linear regression model of standard slope using the GraphPad Prism software.

Results

Figure 5A:
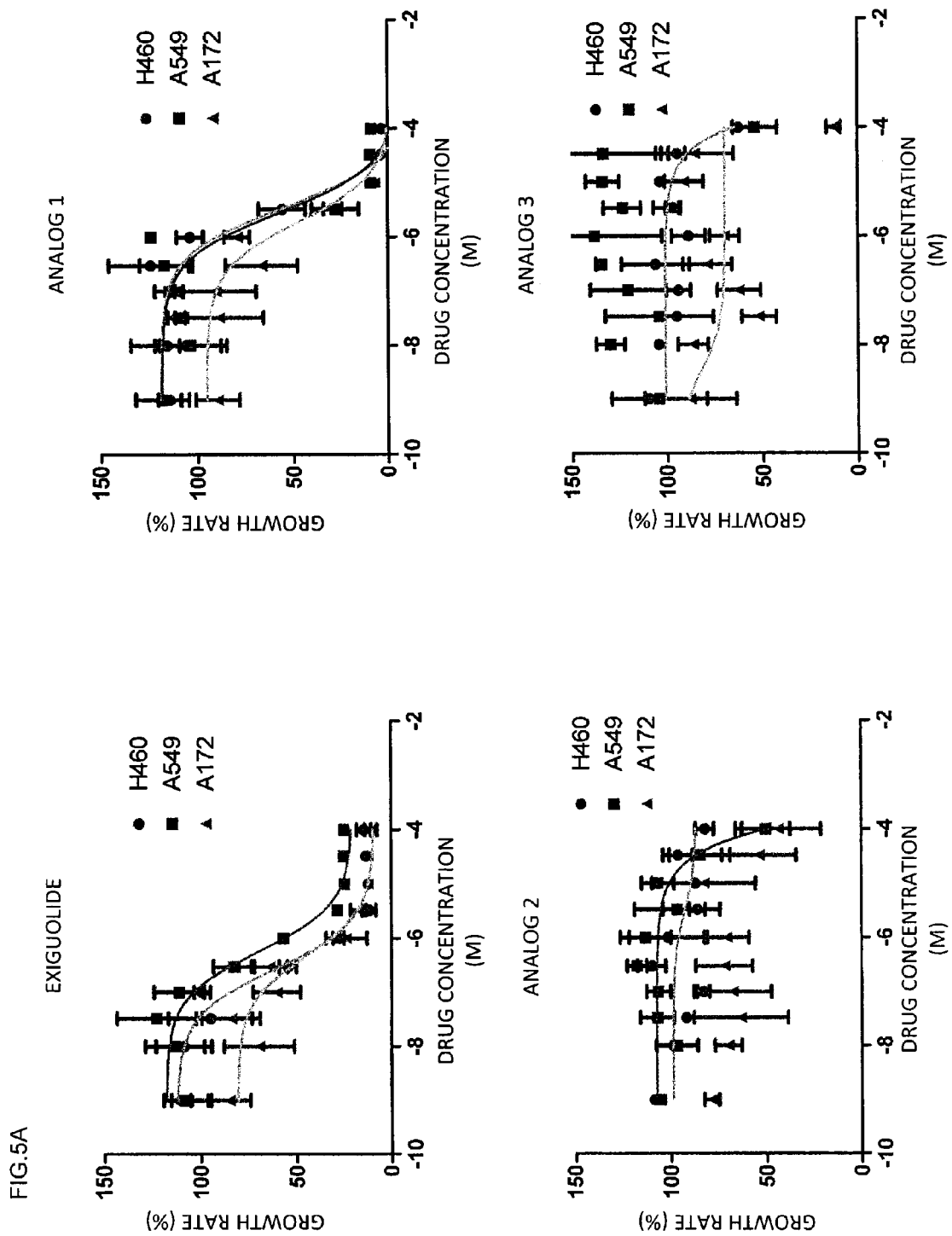
FIG. 5A shows antiproliferative activities of (−)exiguolide and its analogs 1 to 3 on A549, H460, and A172 cell lines, where in each graph, the vertical axis represents the cell growth rate (%); and the horizontal axis represents the drug concentration (M).
Figure 5B:
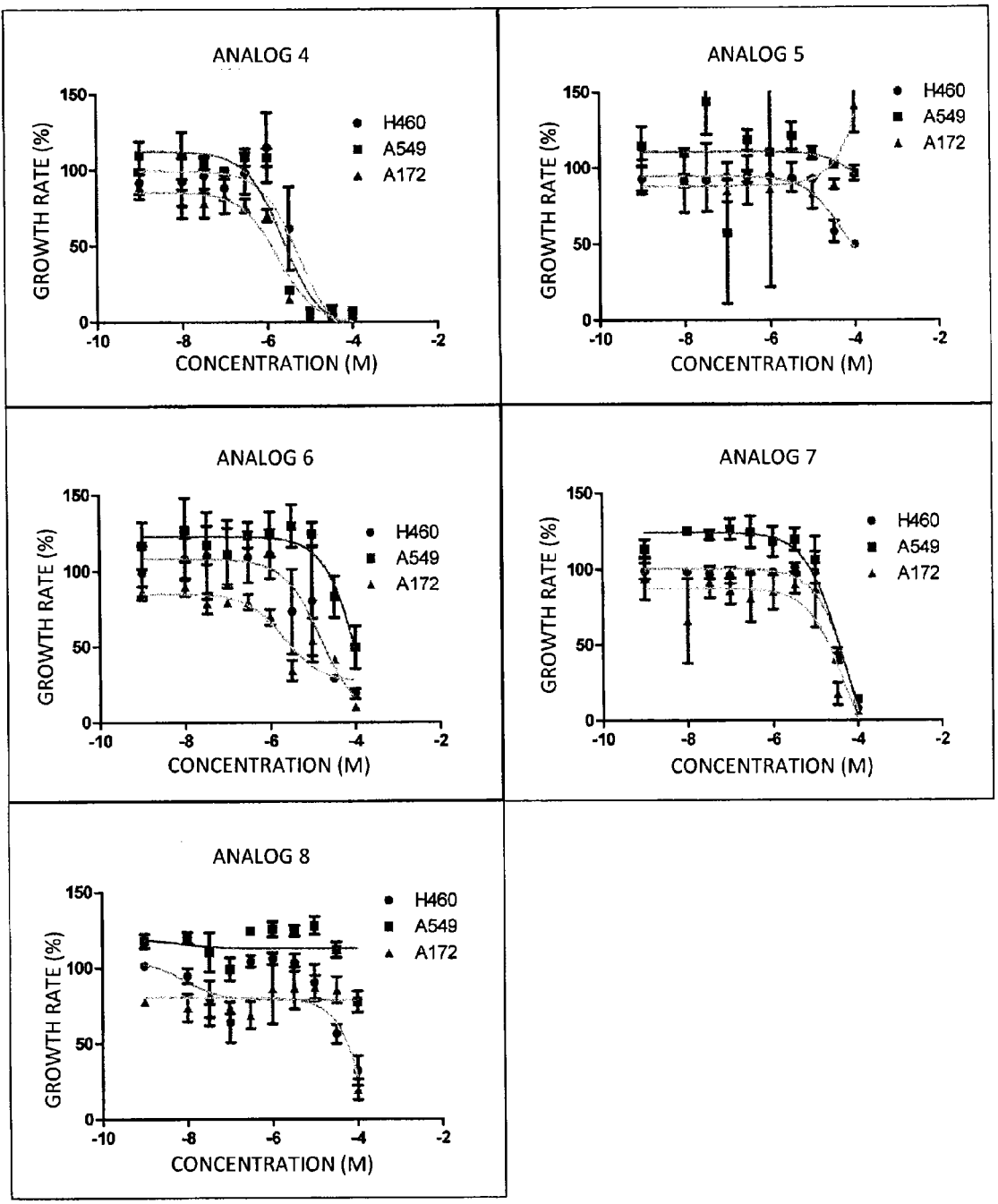
FIG. 5B shows antiproliferative activities of (−)exiguolide and its analogs 4 to 8 on A549, H460, and A172 cell lines, where in each graph, the vertical axis represents the cell growth rate (%); and the horizontal axis represents the drug concentration (M).

The results are shown in FIGS. 5A and 5B and FIG. 6. The $IC_{50}$ of (−)exiguolide was 0.28 µM for H460, 0.59 µM for A549, and 0.46 µM for A172. In other analogs (analogs 1 to 8), $IC_{50}$ was in the range of 2 to 100 µM. In contrast, the $IC_{50}$ for HUVECs was about 10 times higher than that for cancer cells.

Among the analogs, analogs 1, 4, and 7 showed remarkable cell growth-inhibiting effects. The growth-inhibiting effects of the analogs are comparable to that of (−)exiguolide, and active induction of cell death was observed (no data are shown). An analog that shows not only growth inhibition but also induction of cell death has high possibility of utility as an anticancer drug.

Test Example 3

Cell-Cycle Arrest Activity of Novel Macrolide Compound

The cell-cycle arrest activity of exiguolide was investigated. The H460 cell line was exposed to 1 µM of exiguolide, and the ratio of cells at each cell cycle phase was measured with a flow cytometer. The DNA staining reagent used was propidium iodide. The A549 cell line was exposed to exiguolide (0.01 to 5 μM) for 72 hours, and then the activity of a cell cycle regulator, Rb, was measured by Wester blotting.

Figure 7:
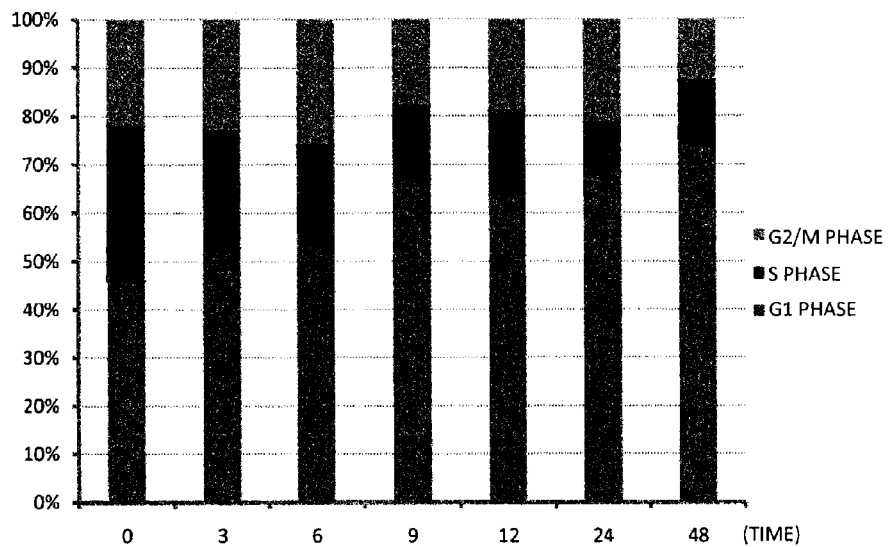
FIG. 7 shows the results of investigation for cell-cycle arrest activity of exiguolide, where the upper is a graph showing ratios of phases of each cell cycle; and the lower shows the results of observation of phosphorylation state of G1 phase regulatory protein Rb by Western blotting.

The results are shown in FIG. 7. The exposure to exiguolide consistently increased the ratio of the G1 phase in cell cycle. This suggests that the cell cycle was arrested at the G1 phase. It was believed that the phosphorylation by a G1-regulating protein, Rb, decreased with an increase in concentration of exiguolide to decrease the activity of Rb. It was believed from these results that exiguolide arrests the cell cycle at G1 phase by controlling the Rb protein to exhibit the cell growth-inhibiting effect.

Test Example 4

In Vivo Antitumor Activity Test of Novel Macrolide Compound

Immunodeficient mice (BALB/cAJcl-nu/nu) were subcutaneously inoculated with human lung cancer cells (H460, A549, etc.). When the subcutaneous tumor volume reached approximately 200 mm$^3$, the mice were divided into an exiguolide administration group (n=2) and a control group (n=4) at random. The administration group was intraperitoneally administered with 0.2 mg/kg of exiguolide, and the control group with PBS (200 μL) and DMSO (5 to 10 μL), every day (once a day). The mice inoculated with the H460 cell line and the A549 cell line were observed for 15 days and 25 days, respectively. The subcutaneous tumors were recognized from the body surface, and the change in tumor diameter was measured with a vernier caliper. Tumor growth of the A549 cell line is slower than that of the H460 cell line, and therefore the mice inoculated with the A549 cell line were observed for a longer period than the mice inoculates with the H460 cell line. After completion of the observation, the mice were euthanized with halothane. The tumors were extracted and were subjected to observation of the size, weight, and pathological findings.

Figure 8:
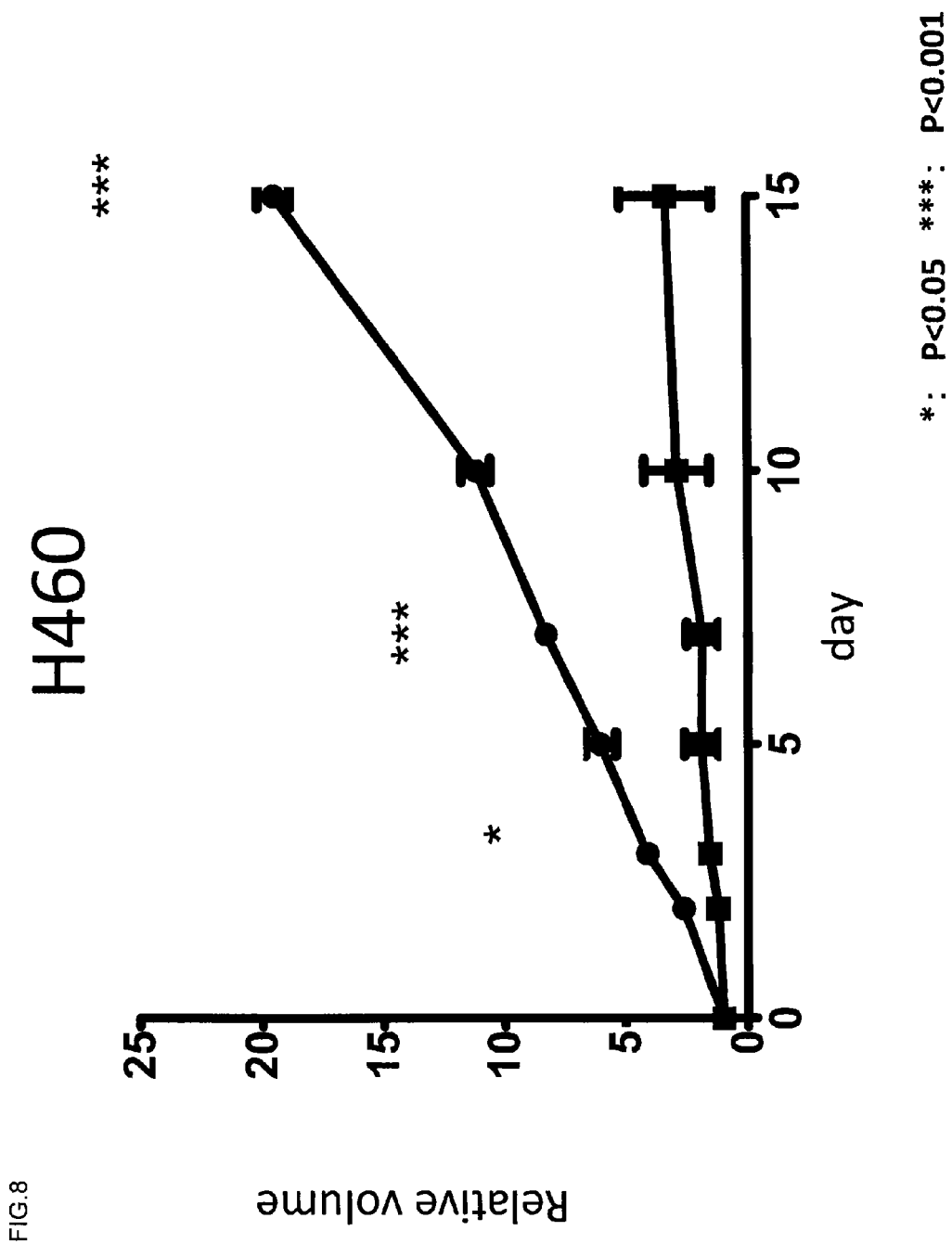
FIG. 8 shows the results of an in vivo antitumor activity test of exiguolide in immunodeficient mice bearing tumors induced by human lung cancer cell line H460, where in the graph, the vertical axis (relative volume) represents the relative values when the estimated tumor volume on the day 0 is defined as 1; and the horizontal axis (day) represents the number of days from the start of administration.
Figure 9:
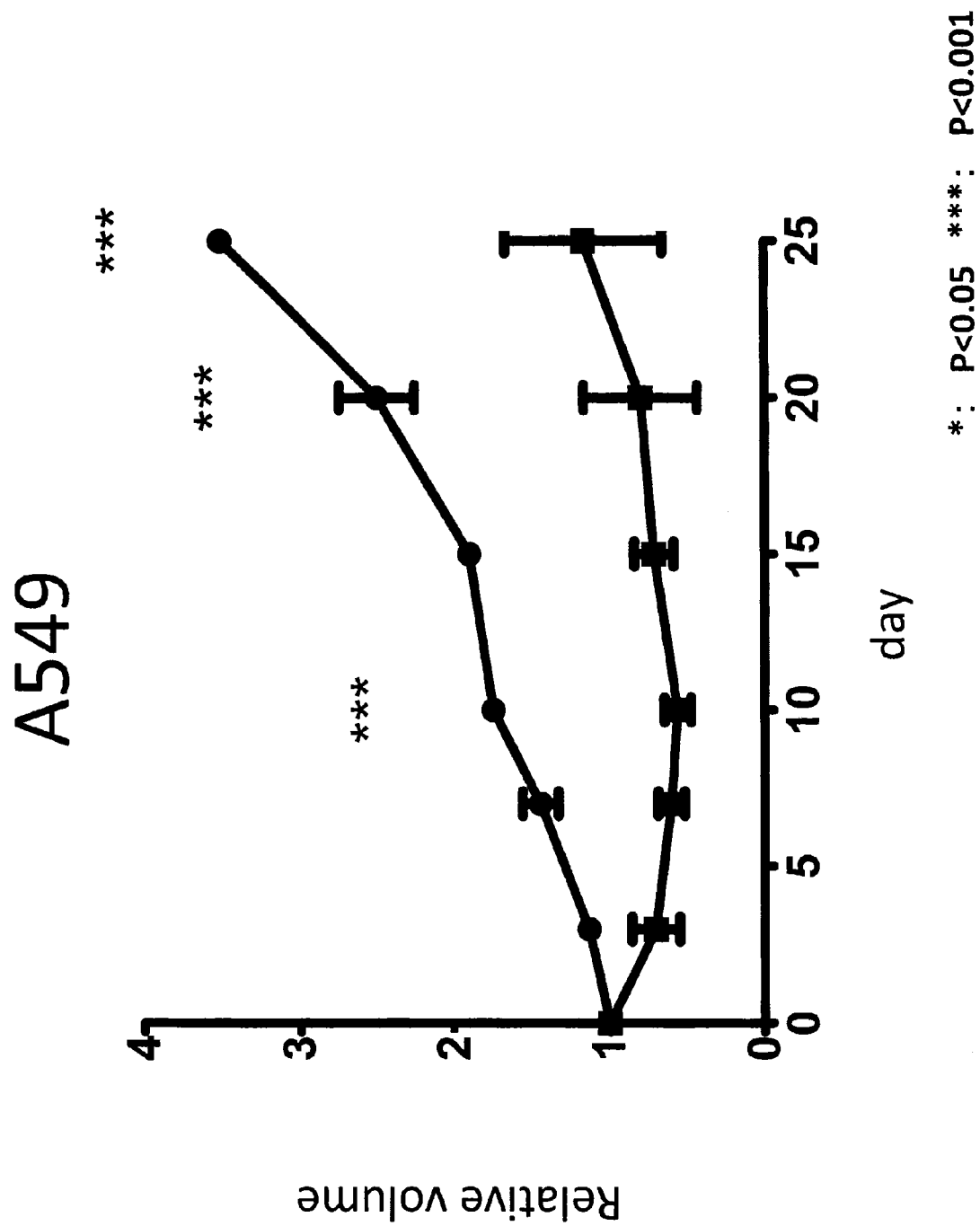
FIG. 9 shows the results of an in vivo antitumor activity test of exiguolide in immunodeficient mice bearing tumors induced by human lung cancer cell line A549, where in the graph, the vertical axis (relative volume) represents the relative values when the estimated tumor volume on the day 0 is defined as 1; and the horizontal axis (day) represents the number of days from the start of administration.

The results are shown in FIG. 8 (H460) and FIG. 9 (A549). In each graph, the vertical axis (relative volume) represents the relative values of the estimated tumor volume of each group to that on the day 0, where the estimated tumor volume is expressed using a major axis "a" and a minor axis "b" by (a×b$^2$)/2.

The relative tumor weight ratios (administration group/control group) at the end of the experiment were 3.35/19.52=0.17 (17%) and 1.17/3.52=0.33 (33%) in the H460 cell line. In general, a relative tumor weight ratio of less than 50% is recognized to have an antitumor effect. It was confirmed from the results shown above that exiguolide has a remarkable antitumor effect on specific cancer cell lines.

All publications, patents, and patent applications cited in this description are herein incorporated by reference in their entirety.

INDUSTRIAL APPLICABILITY

The present invention provides a novel macrolide compound having cell growth-inhibiting activity. The macrolide compound of the present invention exhibits a remarkable cell growth-inhibiting effect on specific cancer cells, compared to that on normal cells. The macrolide compound has high possibility of acting on the cell cycle at a phase different from that in conventionally known anticancer drugs and is therefore expected to show advantageous effects in combination with other anticancer drugs or effects of overcoming multiple drug resistance.

The invention claimed is:
1. A compound represented by Formula (I) or (II):

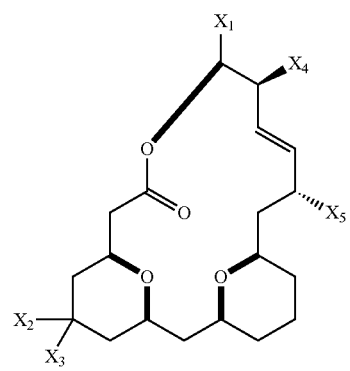

wherein, $X^1$ represents the following formula:

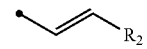

wherein, $R_2$ represents H, $C_1$-$C_{10}$ alkyl, optionally substituted $C_2$-$C_{10}$ alkenyl, optionally substituted $C_5$-$C_{10}$ aryl or —CH=CH—CH=CCH$_3$CH$_2$COOCH$_3$;
$X^2$ and $X^3$ each independently represent H, —OH, or —OC(O)CH$_3$; and
$X^4$ and $X^5$ represent CH$_3$

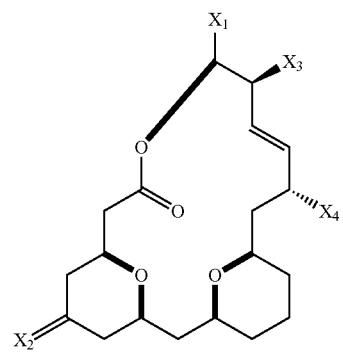

wherein, $X^1$ represents the following formula:

wherein,
$R_2$ represents H, $C_1$-$C_{10}$ alkyl, optionally substituted $C_2$-$C_{10}$ alkenyl, or —CH=CH—CH=CCH$_3$CH$_2$COOCH$_3$;
$X^2$ represents =O, =CHCOOCH$_3$, =CH$_2$; and
$X^3$ and $X^4$ represent CH$_3$
with the proviso that when said compound is of formula (II) and $X^2$ is =CHCOOCH$_3$, $R_2$ represents $C_1$-$C_{10}$ alkyl, optionally substituted $C_2$-$C_{10}$ alkenyl, or —CH=CH—CH=CCH$_3$CH$_2$COOCH$_3$
or a pharmaceutically acceptable salt of the compound, wherein the compound is not exiguolide.

2. A compound selected from the following compounds or a pharmaceutically acceptable salt of the compound:
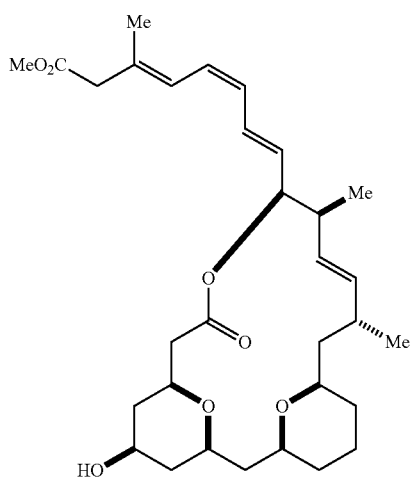
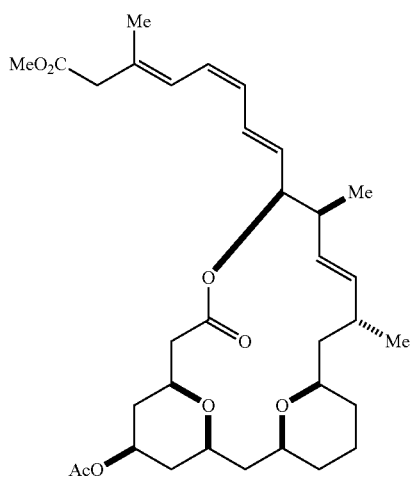
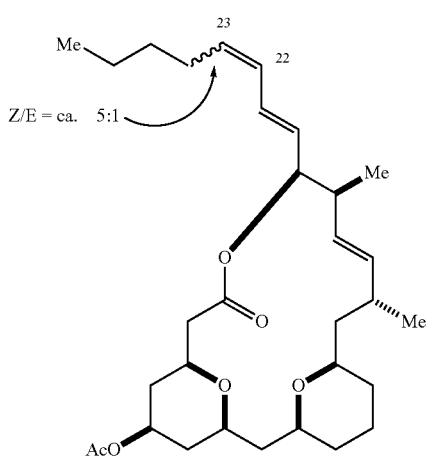
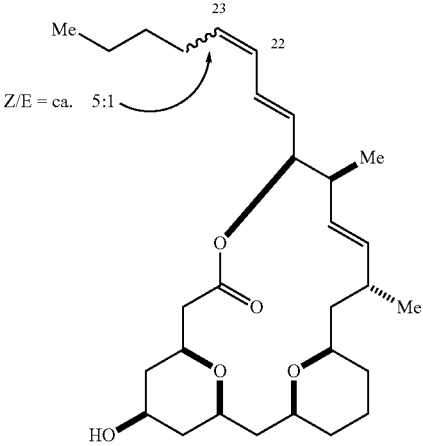
-continued
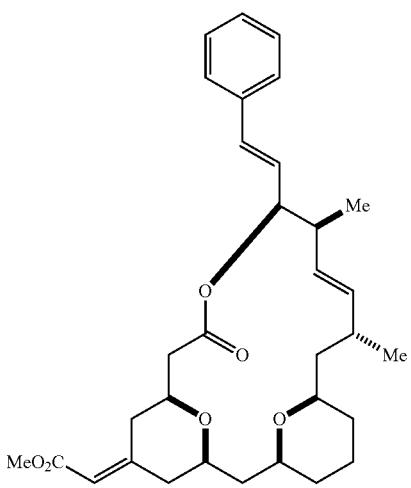
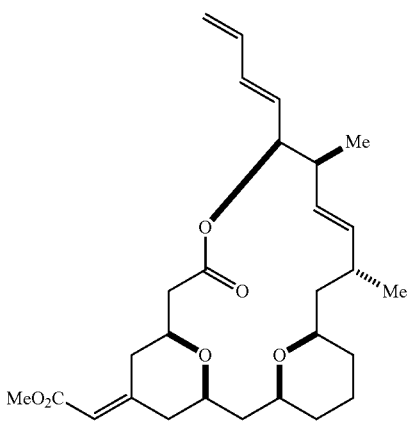

77
-continued
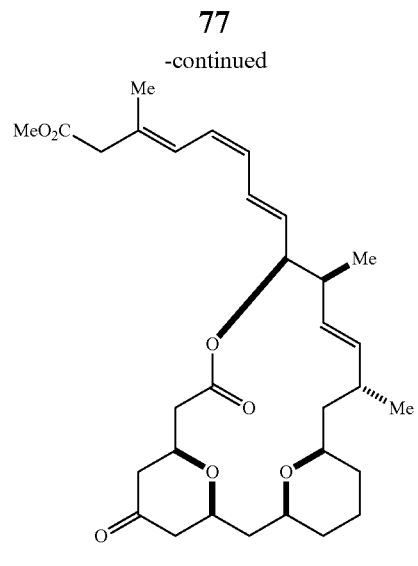
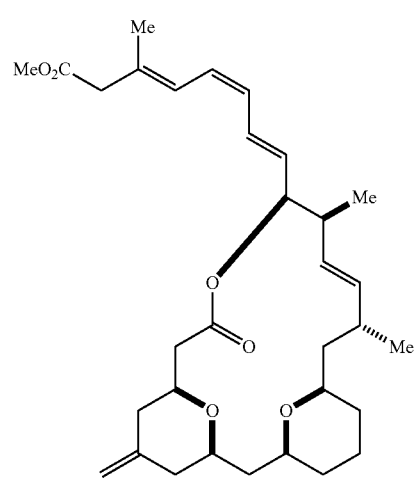
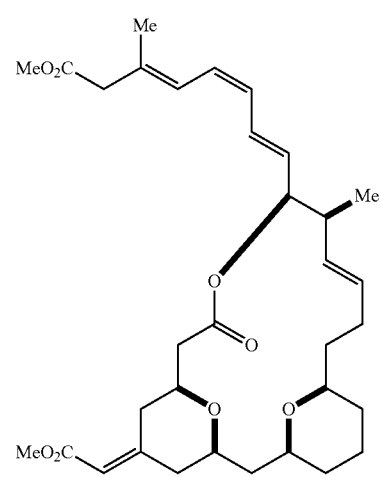
78
-continued
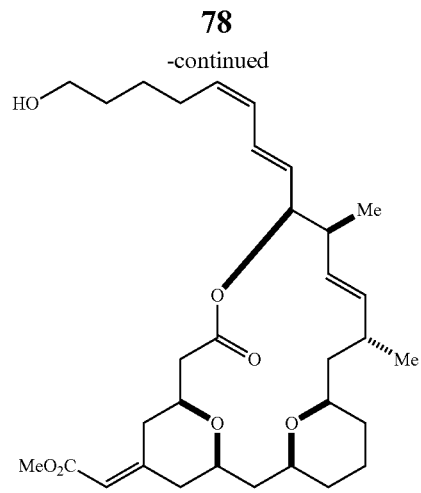
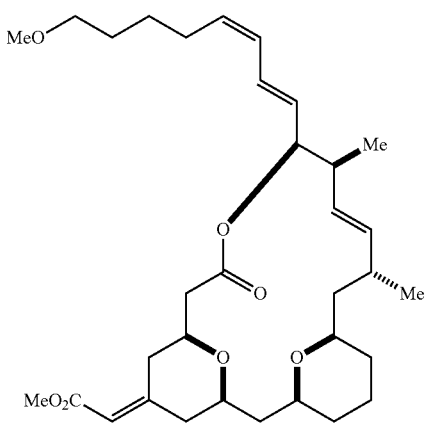
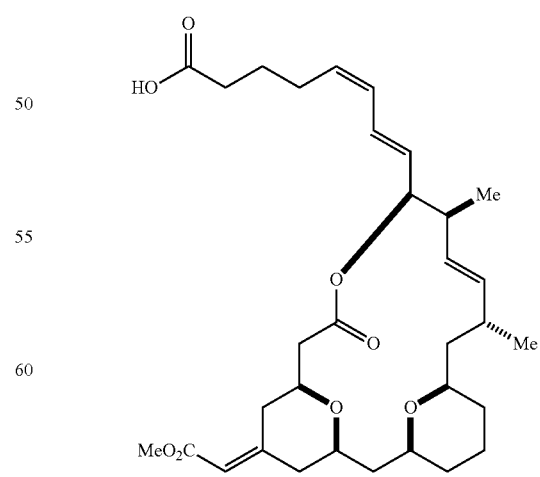

79
-continued
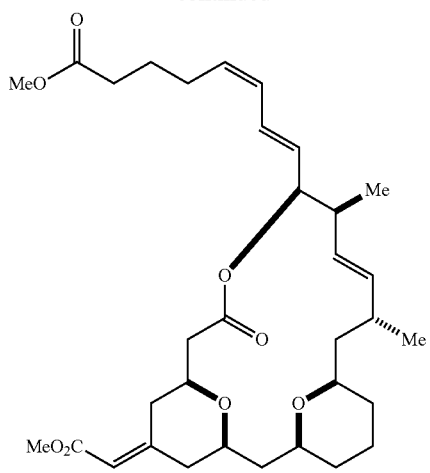
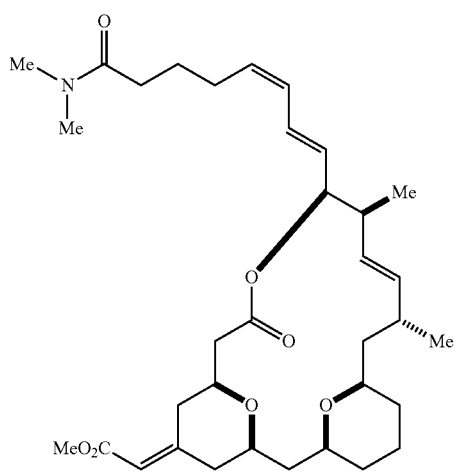
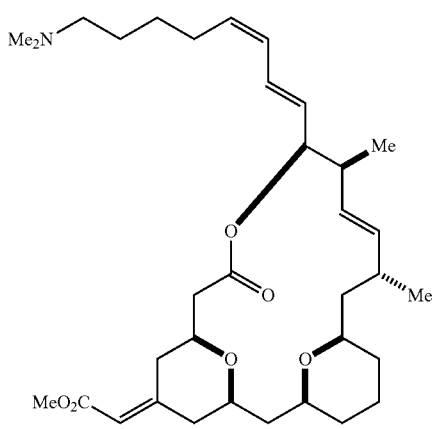
80
-continued
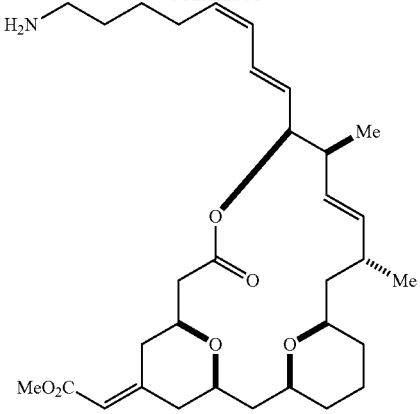
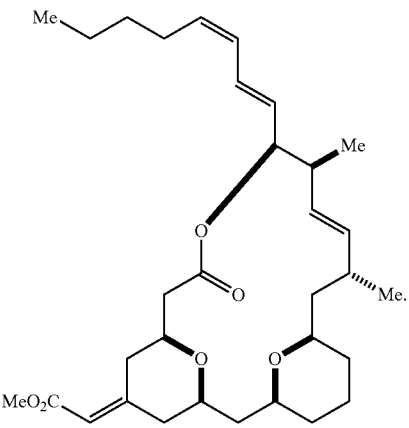
3. A compound selected from the following compounds or a pharmaceutically acceptable salt of the compound:
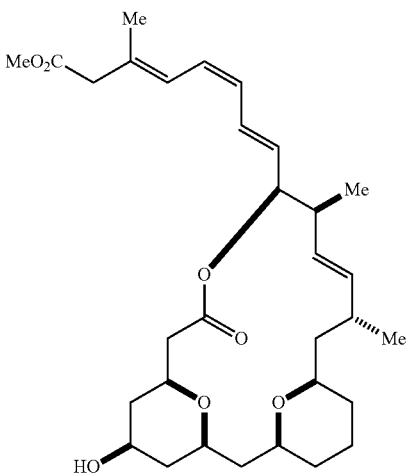

81
-continued
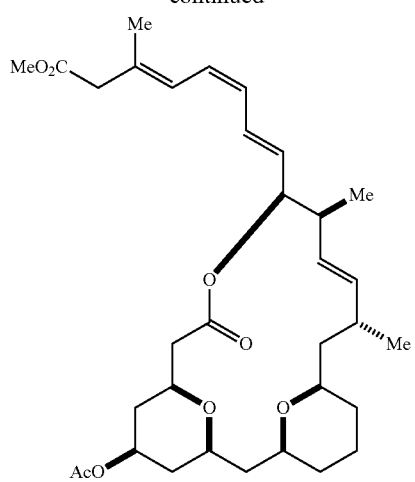
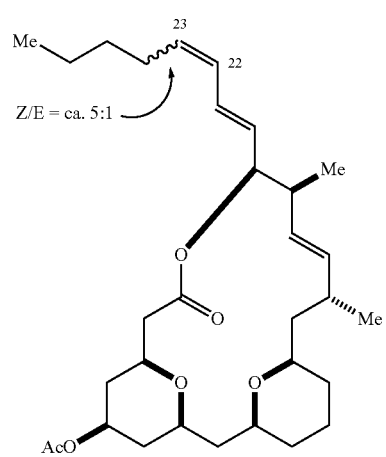
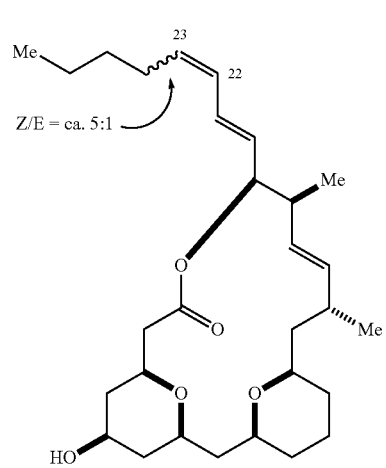
82
-continued
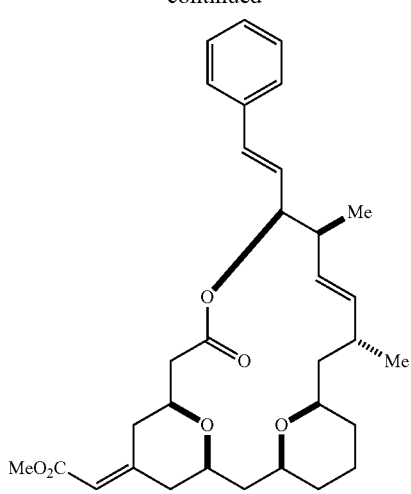
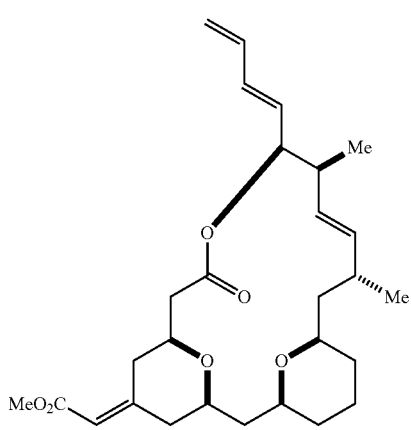
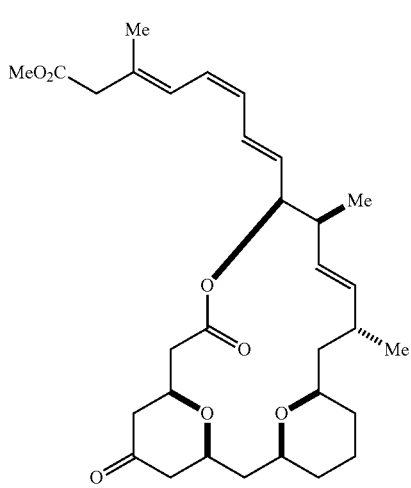

-continued
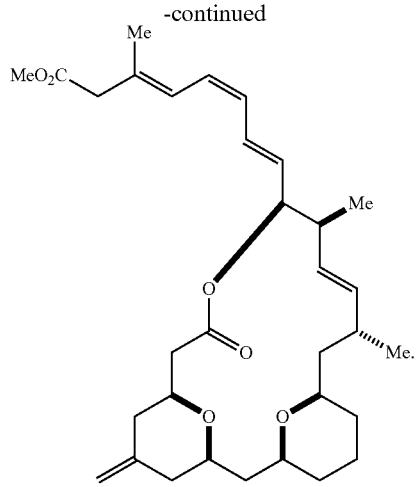
* * * * *